United States Patent
Nishide et al.

(10) Patent No.: US 9,755,165 B2
(45) Date of Patent: Sep. 5, 2017

(54) SILSESQUIOXANE COMPOUND, ORGANIC LIGHT EMITTING ELEMENT, DISPLAY APPARATUS, IMAGE INFORMATION PROCESSING APPARATUS, AND IMAGE FORMING APPARATUS

(71) Applicant: CANON KABUSHIKI KAISHA, Tokyo (JP)

(72) Inventors: Yosuke Nishide, Kawasaki (JP); Naoki Yamada, Inagi (JP); Jun Kamatani, Tokyo (JP); Ryuji Ishii, Yokohama (JP); Norifumi Kajimoto, Tokyo (JP); Takayuki Ito, Kawasaki (JP); Nobutaka Mizuno, Tokyo (JP); Koichi Ishige, Yokohama (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/779,185

(22) PCT Filed: Mar. 25, 2014

(86) PCT No.: PCT/JP2014/059389
§ 371 (c)(1),
(2) Date: Sep. 22, 2015

(87) PCT Pub. No.: WO2014/163028
PCT Pub. Date: Oct. 9, 2014

(65) Prior Publication Data
US 2016/0118607 A1 Apr. 28, 2016

(30) Foreign Application Priority Data
Apr. 3, 2013 (JP) ................................ 2013-077440

(51) Int. Cl.
| C07F 7/00 | (2006.01) |
| H01L 51/00 | (2006.01) |
| C07F 7/21 | (2006.01) |
| G03G 15/04 | (2006.01) |
| G06T 1/00 | (2006.01) |
| H01L 27/32 | (2006.01) |
| H05B 33/08 | (2006.01) |
| H01L 51/50 | (2006.01) |
| H05B 33/22 | (2006.01) |

(52) U.S. Cl.
CPC ............ *H01L 51/0094* (2013.01); *C07F 7/21* (2013.01); *G03G 15/04036* (2013.01); *G06T 1/00* (2013.01); *H01L 27/3225* (2013.01); *H01L 51/006* (2013.01); *H01L 51/0059* (2013.01); *H05B 33/0896* (2013.01); *H01L 51/0058* (2013.01); *H01L 51/5056* (2013.01); *H01L 2251/558* (2013.01); *H05B 33/22* (2013.01)

(58) Field of Classification Search
CPC ........ H01L 51/50; H01L 27/32; C07C 211/60; C07F 7/21; C09K 11/06; G09F 9/30
USPC ......................................................... 556/424
See application file for complete search history.

(56) References Cited

U.S. PATENT DOCUMENTS

| 6,517,958 B1 * | 2/2003 | Sellinger ............. H01L 51/0039 252/301.35 |
| 8,188,500 B2 | 5/2012 | Hasegawa et al. |
| 2003/0204038 A1 | 10/2003 | Xiao et al. |
| 2007/0045619 A1 | 3/2007 | Park et al. |
| 2010/0155711 A1 | 6/2010 | Hasegawa et al. |

FOREIGN PATENT DOCUMENTS

| CN | 101397308 A | 4/2009 |
| JP | 2000-306669 A | 11/2000 |
| JP | 2002-25780 A | 1/2002 |
| JP | 2005-104026 A | 4/2005 |
| JP | 2006-108458 A | 4/2006 |
| JP | 3880518 B2 | 11/2006 |
| JP | 3880518 B2 | 2/2007 |
| JP | 2012-177061 A | 9/2012 |
| JP | 2012-195303 A | 10/2012 |
| JP | 2013-38062 A | 2/2013 |
| WO | 2010/063612 A1 | 6/2010 |

OTHER PUBLICATIONS

H. Araki et al., "Syntheses and properties of star- and dumbbell-shaped POSS derivatives containing isobutyl groups", Polymer Journal, vol. 44, pp. 340-346 (2012).
S. Fan et al., "Efficient white-light-emitting diodes based on polyfluorene doped with fluorescent chromophores", Appl. Phys. Lett., vol. 91, pp. 213502-1-213502-3 (2007).
I. Venegoni et al., "A novel electroluminescent PPV copolymer and silsesquioxane nanocomposite film for the preparation of efficient PLED devices", Nanotechonology, vol. 23, 435702 (6 pp) (2012).
W. Zhu, et al., "Field-effect mobilities of polyhedral oligomeric silsesquioxanes anchored semiconducting polymers", Applied Surface Science, vol. 221, pp. 358-363 (2004).
European Search Report issued for corresponding application No. 14779480.4 dated Nov. 7, 2016—7 pages.
Extended European Search Report dated Mar. 1, 2017, issued for counterpart application No. 14779480.4—13 pages.
Japanese Office Action dated Mar. 27, 2017, issued for counterpart application No. JP 2013-077440—6 pages.

\* cited by examiner

*Primary Examiner* — Sudhakar Katakam
*Assistant Examiner* — Kofi Adzamli
(74) *Attorney, Agent, or Firm* — Fitzpatrick, Cella, Harper & Scinto

(57) ABSTRACT

Provided is an organic light emitting element having high light emitting efficiency. The organic light emitting element includes: an anode; a cathode; an emission layer placed between the anode and the cathode; and a hole transport layer formed between the anode and the emission layer, in which the hole transport layer contains a siloxane compound and a compound having a tertiary arylamine structure; and number of $SP^2$ carbon atoms in the hole transport layer is ten times or less number of silicon atoms in the hole transport layer.

15 Claims, 1 Drawing Sheet

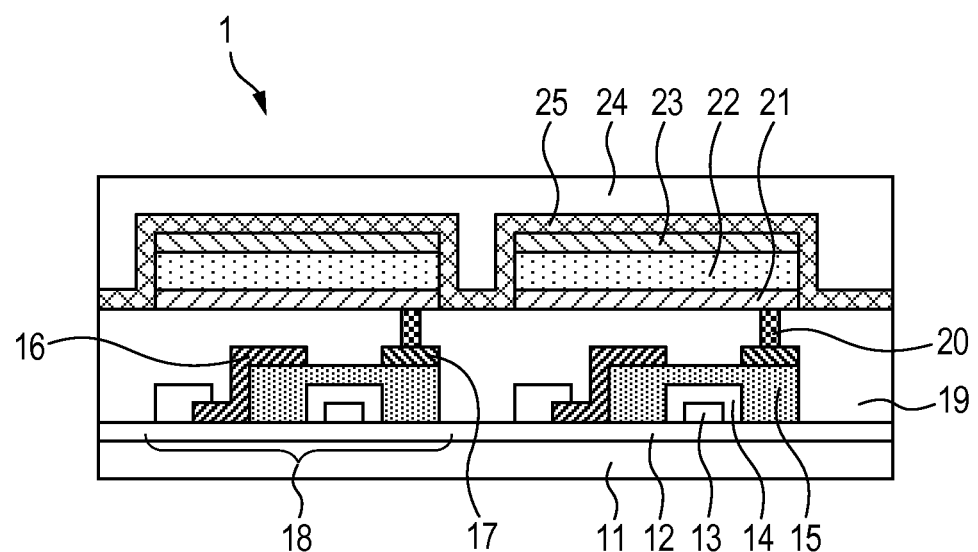

SILSESQUIOXANE COMPOUND, ORGANIC LIGHT EMITTING ELEMENT, DISPLAY APPARATUS, IMAGE INFORMATION PROCESSING APPARATUS, AND IMAGE FORMING APPARATUS

TECHNICAL FIELD

The present invention relates to a silsesquioxane compound, and an organic light emitting element, a display apparatus, an image information processing apparatus, and an image forming apparatus each using the compound.

BACKGROUND ART

An organic light emitting element (organic electroluminescence element or organic EL element) is an electronic element including a pair of electrodes and an organic compound layer placed between the pair of electrodes. An electron and a hole are injected from the pair of electrodes, and then the electron and the hole recombine in the organic compound layer to produce an exciton of a luminous organic compound. The organic light emitting element emits light upon return of the exciton to its ground state.

A method of improving the light emitting efficiency of the organic EL element is, for example, a method involving utilizing a triplet excited state. Several specific methods each involving utilizing the triplet excited state have been currently proposed. At present, however, it is difficult to keep an exciton produced in the organic EL element trapped in a layer responsible for light emission. Accordingly, various kinds of research and development have been performed to overcome the difficulty.

PTL 1 proposes, as a compound for trapping an exciton in a specific layer (such as an emission layer), a compound having a silsesquioxane structure, specifically, Compounds a-1 and b-1 shown below.

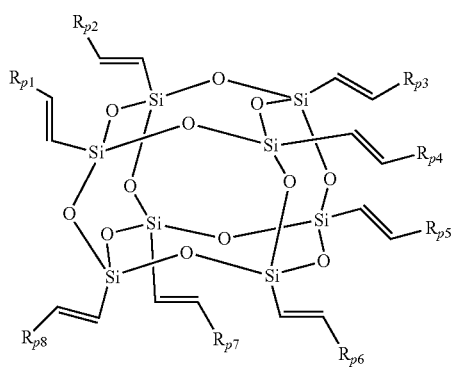

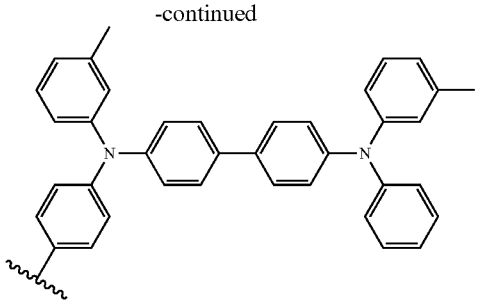

a-1

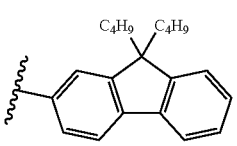

$R_{p1}\text{-}R_{p5}=$ $R_{p6}\text{-}R_{p8}=H$ b-1

Here, the silsesquioxane compounds (Compound a-1 and Compound b-1) proposed in PTL 1 are each a compound that has a high ratio of an aryl group to a silsesquioxane unit, has a high absorbance, and can easily stack between its molecules.

CITATION LIST

Patent Literature

PTL 1: Japanese Patent No. 3880518

SUMMARY OF INVENTION

Technical Problem

The present invention has been made to solve the problems and an object of the present invention is to provide an organic light emitting element having high light emitting efficiency.

The organic light emitting element of the present invention includes: an anode; a cathode; an emission layer placed between the anode and the cathode; and a hole transport layer formed between the anode and the emission layer, in which: the hole transport layer contains a siloxane compound and a compound having a tertiary arylamine structure; and number of $SP^2$ carbon atoms in the hole transport layer is ten times or less number of silicon atoms in the hole transport layer.

Further features of the present invention will become apparent from the following description of exemplary embodiments (with reference to the attached drawings).

BRIEF DESCRIPTION OF DRAWINGS

FIG. 1 is a schematic sectional view illustrating a display apparatus having an organic light emitting element and an active element connected to the organic light emitting element.

DESCRIPTION OF EMBODIMENTS

An organic light emitting element of the present invention includes an anode, a cathode, an emission layer placed between the anode and the cathode, and a hole transport layer formed between the anode and the emission layer, provided that in the present invention, at least the emission layer and the hole transport layer have only to be present in an organic compound layer placed between the anode and the cathode, and an intervention layer may be formed between the emission layer and the cathode, between the emission layer and the hole transport layer, or between the hole transport layer and the anode. Examples of the intervention layer as used herein include a hole injection layer, a hole transport layer, an electron blocking layer, a hole blocking layer, an electron transport layer, an electron injection layer, and an exciton blocking layer. One kind selected from the layers may be used as the intervention layer, or an appropriate combination of two or more kinds selected from the layers may be used as the intervention layer.

In addition, a method of providing the intervention layer is specifically, for example, a method involving providing an insulating layer, an adhesion layer, or an interference layer at an interface between an electrode and the organic compound layer. In addition, various layer constructions can be adopted; for example, the electron transport layer or the hole transport layer is a laminate formed of two layers different from each other in ionization potential.

In the present invention, the light extraction construction of the organic light emitting element may be a bottom emission system in which light is extracted from an electrode on a side closer to a substrate, or may be a top emission system in which light is extracted from a side opposite to the substrate. A construction in which light is extracted from each of both the side closer to the substrate and the side opposite to the substrate is also permitted.

In the present invention, the hole transport layer contains a siloxane compound and a compound having a tertiary arylamine structure. Further, in the present invention, number of $SP^2$ carbon atoms in the hole transport layer is ten times or less number of silicon atoms in the hole transport layer. It should be noted that the present invention also comprehends the case where the number of the $SP^2$ carbon atoms in the hole transport layer is zero. By the way, the term "ten times" as used herein means that the magnification equals 10 when rounded off to the nearest integer. More specifically, the term is a concept indicating that the magnification is 9.5 or more and less than 10.5.

In the present invention, the siloxane compound is a compound whose main skeleton is formed of silicon and oxygen, and is specifically a compound having a bonding form represented by Si—O—Si (siloxane bond). More specifically, the compound refers to, for example, a compound represented by any one of the following general formulae [16] to [26]. It should be noted that the siloxane compound to be used in the present invention is not limited to the compounds represented by the following general formulae [16] to [26] as long as the compound satisfies the requirement that the number of the $SP^2$ carbon atoms in the hole transport layer should be ten times or less the number of the silicon atoms in the hole transport layer. In addition, a particularly preferred compound out of the siloxane compounds to be used in the present invention is described later.

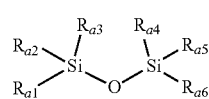

[16]

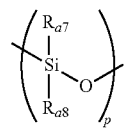

[17]

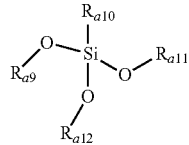

[18]

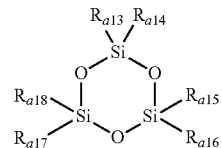

[19]

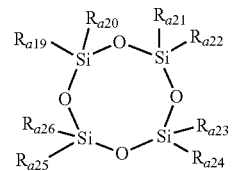

[20]

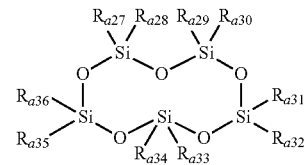

[21]

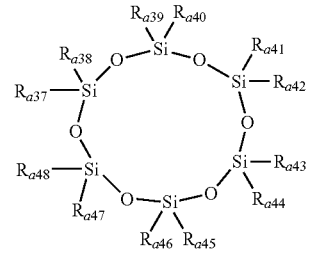

[22]

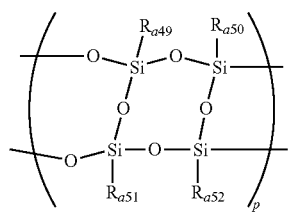

[23]

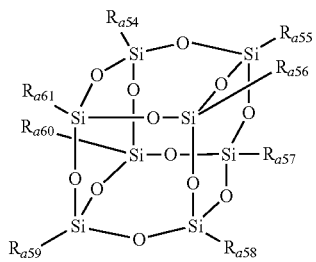

[24]

-continued

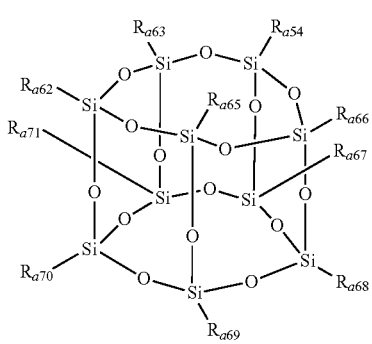
[25]

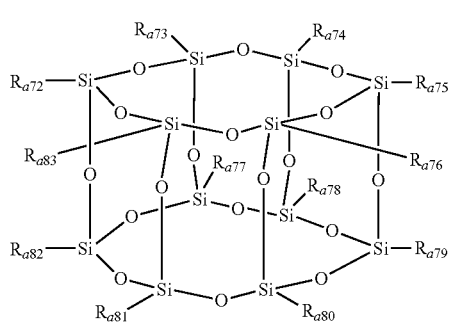
[26]

In the general formulae [16] to [26], $R_{a1}$ to $R_{a83}$ each represent an alkyl group, an aryl group, an alkoxy group, a phenoxy group, an arylamino group, or a halogen atom. It should be noted that the aryl group or the arylamino group represented by any one of $R_{a1}$ to $R_{a83}$ may further have a substituent.

Examples of the alkyl group represented by any one of $R_{a1}$ to $R_{a83}$ include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, and a cyclooctyl group.

Examples of the aryl group represented by any one of $R_{a1}$ to $R_{a83}$ include a phenyl group, a biphenyl group, a terphenyl group, a naphthyl group, a phenanthrenyl group, a fluorenyl group, a triphenylenyl group, a chrysenyl group, and a pyrenyl group.

Examples of the alkoxy group represented by any one of $R_{a1}$ to $R_{a83}$ include a methoxy group, an ethoxy group, a propoxy group, a butoxy group, a t-butoxy group, a hexyloxy group, an ethylhexyloxy group, and an octyloxy group.

The arylamino group represented by any one of $R_{a1}$ to $R_{a83}$ refers to a substituent in which an aryl group is bonded to a nitrogen atom (N atom). Examples of the aryl group bonded to a nitrogen atom (N atom) include a phenyl group, a biphenyl group, a terphenyl group, a naphthyl group, a phenanthrenyl group, a fluorenyl group, a triphenylenyl group, a chrysenyl group, and a pyrenyl group.

Examples of the halogen atom represented by any one of $R_{a1}$ to $R_{a83}$ include chlorine, bromine, and fluorine. The halogen atom is preferably fluorine.

As a substituent that the aryl group or arylamino group may further have, there may be given, for example: an alkyl group such as a methyl group, a t-butyl group, or a cyclopentyl group; an aryl group such as a phenyl group or a biphenyl group; a dimethylamino group; an alkoxyl group such as a methoxy group; a phenoxy group; an arylamino group; a cyano group; and a halogen atom such as fluorine, chlorine, bromine, or iodine. It should be noted that the number of substituents which the aryl group and the arylamino group may each further have is not particularly limited as long as the requirement that the number of the $SP^2$ carbon atoms in the hole transport layer should be ten times or less the number of the silicon atoms in the hole transport layer is satisfied.

In the present invention, examples of the compound having a tertiary arylamine structure as one of the compounds in the hole transport layer include, but not limited to, compounds represented by the following general formulae [27] to [33].

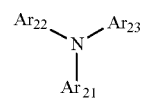
[27]

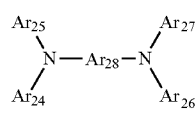
[28]

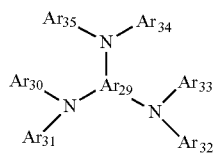
[29]

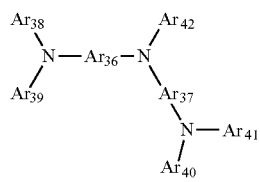
[30]

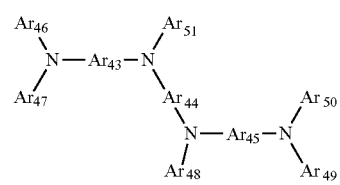
[31]

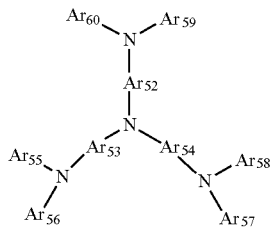
[32]

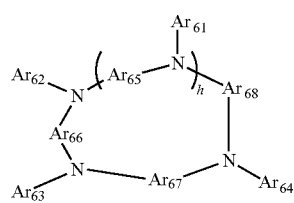
[33]

It should be noted that the compounds represented by the general formulae [27] to [33] each serving as the compound having a tertiary arylamine structure each have at least one tertiary arylamine structure as shown in Table 1 below.

TABLE 1

| | Number of tertiary arylamine structures in compound |
|---|---|
| General Formula [27] | 1 |
| General Formula [28] | 2 |
| General Formula [29] | 3 |
| General Formula [30] | 3 |
| General Formula [31] | 4 |
| General Formula [32] | 4 |
| General Formula [33] | 4-6 (Note 1) |

(Note 1) The number changes depending on h (h represents an integer of 1 to 3).

In the general formulae [27] to [33], $Ar_{21}$ to $Ar_{68}$ each represent an aryl group, a heterocyclic group, a halogen group, an amino group, an alkyl group, or an alkoxy group. It should be noted that of the substituents $Ar_{21}$ to $Ar_{68}$ in the general formulae [27] to [33], $Ar_{21}$ to $Ar_{23}$, $Ar_{24}$ to $Ar_{27}$, $Ar_{30}$ to $Ar_{35}$, $Ar_{38}$ to $Ar_{42}$, $Ar_{46}$ to $Ar_{51}$, $Ar_{55}$ to $Ar_{60}$ and $Ar_{61}$ to $Ar_{64}$ each represent a monovalent substituent. In addition, of the substituents $Ar_{21}$ to $Ar_{68}$ in the general formulae [27] to [33], $Ar_{28}$, $Ar_{36}$, $Ar_{37}$, $Ar_{43}$ to $Ar_{45}$, $Ar_{52}$ to $Ar_{54}$, and $Ar_{65}$ to $Ar_{68}$ each represent a divalent substituent. In addition, of the substituents $Ar_{21}$ to $Ar_{68}$ in the general formulae [27] to [33], $Ar_{29}$ represents a trivalent substituent.

In the general formulae [27] to [33], the aryl group represented by any one of $Ar_{21}$ to $Ar_{68}$ may further have a substituent.

Examples of the aryl group represented by any one of $Ar_{21}$ to $Ar_{68}$ include a phenyl group, a naphthyl group, a pentalenyl group, an indenyl group, an azulenyl group, an anthryl group, a pyrenyl group, an indacenyl group, an acenaphthenyl group, a phenanthryl group, a phenarenyl group, a fluoranthenyl group, an acephenanthryl group, an aceanthryl group, a triphenylenyl group, a chrysenyl group, a naphthacenyl group, a perylenyl group, a pantacenyl group, a biphenyl group, a terphenyl group, and a fluorenyl group.

Examples of the heterocyclic group represented by any one of $Ar_{21}$ to $Ar_{68}$ include a thienyl group, a pyrrolyl group, a pyridyl group, an oxazolyl group, an oxadiazolyl group, a thiazolyl group, a thiadiazolyl group, a terthienyl group, a dibenzothiophenyl group, a dibenzofuryl group, and a phenanthrolyl group.

Examples of the halogen atom represented by any one of $Ar_{21}$ to $Ar_{68}$ include chlorine, bromine, and fluorine. The halogen atom is preferably fluorine.

Examples of the amino group represented by any one of $Ar_{21}$ to $Ar_{68}$ include a dimethyl amino group, a diethyl amino group, dibenzyl amino group, a diphenyl amino group, a ditolyl amino group, and a dianisolyl amino group.

Examples of the alkyl group represented by any one of $Ar_{21}$ to $Ar_{68}$ include a methyl group, an ethyl group, an n-propyl group, an isopropyl group, an n-butyl group, a t-butyl group, an s-butyl group, an ethylhexyl group, an octyl group, a 1-adamantyl group, and a 2-adamantyl group. Of those, the following alkyl group having 8 or less carbon atoms is preferred: a methyl group, an ethyl group, an n-propyl group, an isopropyl group, an n-butyl group, a t-butyl group, an s-butyl group, an ethylhexyl group, or an octyl group.

Examples of the alkoxy group represented by any one of $Ar_{21}$ to $Ar_{68}$ include a methoxy group, an ethoxy group, a propoxy group, a butoxy group, a t-butoxy group, a hexyloxy group, an ethylhexyloxy group, and an octyloxy group.

Examples of the above-mentioned substituent that the aryl group may further have include: an alkyl group such as a methyl group, an ethyl group, or a propyl group; an aryl group such as a phenyl group or a biphenyl group; a heterocyclic group such as a thyenyl group, a pyrrolyl group, or a pyridyl group; an amino group such as a dimethylamino group, a diethylamino group, a dibenzylamino group, a diphenylamino group, a ditolylamino group, or a dianisolylamino group; an alkoxyl group such as a methoxyl group, an ethoxyl group, a propoxyl group, a phenoxyl group; cyano group; and a halogen atom such as fluorine, chlorine, bromine, or iodine.

In the general formula [27], $Ar_{21}$ to $Ar_{23}$ may be identical to or different from one another. In addition, adjacent substituents may be bonded to each other to form a heterocycle containing a nitrogen atom such as carbazole.

In the general formula [28], $Ar_{22}$ to $Ar_{28}$ may be identical to or different from one another. In addition, adjacent substituents ($Ar_{24}$ and $Ar_{25}$, $Ar_{26}$ and $Ar_{27}$) may be bonded to each other to form a heterocycle containing a nitrogen atom such as carbazole.

In the general formula [29], $Ar_{29}$ to $Ar_{35}$ may be identical to or different from one another. In addition, adjacent substituents ($Ar_{30}$ and $Ar_{31}$, $Ar_{32}$ and $Ar_{33}$, $Ar_{34}$ and $Ar_{35}$) may be bonded to each other to form a heterocycle containing a nitrogen atom such as carbazole.

In the general formula [30], $Ar_{36}$ to $Ar_{42}$ may be identical to or different from one another. In addition, adjacent substituents ($Ar_{38}$ and $Ar_{39}$, $Ar_{40}$ and $Ar_{41}$) may be bonded to each other to form a heterocycle containing a nitrogen atom such as carbazole.

In the general formula [31], $Ar_{43}$ to $Ar_{51}$ may be identical to or different from one another. In addition, adjacent substituents ($Ar_{46}$ and $Ar_{47}$, $Ar_{49}$ and $Ar_{50}$) may be bonded to each other to form a heterocycle containing a nitrogen atom such as carbazole.

In the general formula [32], $Ar_{43}$ to $Ar_{51}$ may be identical to or different from one another. In addition, adjacent substituents ($Ar_{46}$ and $Ar_{47}$, $Ar_{49}$ and $Ar_{50}$) may be bonded to each other to form a heterocycle containing a nitrogen atom such as carbazole.

In the general formula [33], $Ar_{43}$ to $Ar_{51}$ may be identical to or different from one another. In addition, adjacent substituents ($Ar_{46}$ and $Ar_{47}$, $Ar_{49}$ and $Ar_{50}$) may be bonded to each other to form a heterocycle containing a nitrogen atom such as carbazole. Further, in the general formula [33], h represents an integer of 1 to 3.

A polymer compound having any one of the general formulae [27] to [32] as a repeating unit is also included in the category of the compound having a tertiary arylamine structure in the hole transport layer.

The number of the silicon atoms in the hole transport layer in the present invention means the total number of the silicon atoms of the siloxane compound in the hole transport layer. In addition, the siloxane compound is a compound having, as its main skeleton, a siloxane unit formed of silicon and oxygen. Accordingly, the siloxane compound is a compound that does not have absorption in a visible region and has a wider band gap than that of an aromatic compound.

Meanwhile, the number of the $SP^2$ carbon atoms in the present invention means the total number of the $SP^2$ carbon atoms serving as a basis for the formation of an unsaturated double bond (C=C) in the compounds in the hole transport layer. An aromatic compound having an aromatic ring obtained by appropriately combining unsaturated double bonds (C=C) generally has absorption in the visible region, and its absorption band shifts to longer wavelengths as the linking number of its aromatic rings increases or the number of its condensed rings increases. In addition, when the aromatic compound is in a thin-film state, a large amount of electrons delocalized by π-electron systems on a solid planar structure and $SP^2$ hybrid orbital of the compound itself are present. Accordingly, a stacking interaction strengthens and hence its band gap narrows as compared with that in a dilute solution state. The effect strengthens as the number of π-electrons increases.

By the way, an aromatic compound having many $SP^2$ carbon atoms has functions of facilitating the exchange of carriers in the organic light emitting element and promoting the hopping movement of the carriers. Further, the aromatic compound, i.e., a tertiary arylamine compound having an aryl group is a compound having a high hole transport ability.

The hole transport layer having the siloxane compound and the compound having a tertiary arylamine structure in the organic light emitting element of the present invention has a function of transporting a carrier (hole), and has the following features (1-1) and (1-2): (1-1) the layer has a low absorbance (particularly in the visible region); and (1-2) the layer has a wide band gap.

First, the feature (1-1) is described. The phrase "low absorbance" as used in the present invention means that the absorbance is low in the wavelength range of from 250 nm to 600 nm. In addition, even the case where an absorption peak appears at a specific wavelength (maximum absorption wavelength) in the wavelength range of from 250 nm to 600 nm corresponds to the "low absorbance" as long as the absorbance of the peak is small. In addition, in the present invention, the absorbance is particularly preferably low in the visible region, i.e., the wavelength range of from 360 nm to 600 nm.

In order that the hole transport layer may be in a state of having a low absorbance in the wavelength range of from 250 nm to 600 nm (preferably the wavelength range of from 360 nm to 600 nm) as described above, the abundance ratio of a siloxane unit having no absorption in the visible region in the hole transport layer is increased. Even when a compound having an aryl group or a tertiary arylamine structure is present in the hole transport layer, increasing the molar ratio of the siloxane unit having no absorption in the visible region in the hole transport layer reduces the molar concentration of the compound. Accordingly, even when an absorption peak appears at a specific wavelength (maximum absorption wavelength) in the wavelength range of from 250 nm to 600 nm in the hole transport layer, the absorbance of the peak reduces. Thus, the broadening of an absorption spectrum toward the visible region caused by the occurrence of a stacking interaction between aromatic rings can be suppressed, and hence the reabsorption of light, which has been generated in the organic light emitting element, in the hole transport layer can be suppressed.

Next, the feature (1-2) is described. In the present invention, for example, methods described in the following items (1-2a) and (1-2b) are each available as a method of widening a band gap in a layer (such as the hole transport layer): (1-2a) a method involving adopting a compound having a small linking number of aromatic rings or a compound having a small number of condensed rings as a compound that is to be incorporated into the layer and has an aromatic ring; and (1-2b) a method involving increasing the molar ratio of a siloxane unit in the layer.

Irrespective of which of the methods (1-2a) and (1-2b) is adopted, upon formation of a thin film serving as the hole transport layer, a stacking interaction is suppressed for the thin film, and hence the shift of the absorption spectrum to shorter wavelengths and the sharpening of its waveform are realized. Accordingly, a wide band gap can be maintained.

In view of the foregoing, in the present invention, the number of the $SP^2$ carbon atoms in the hole transport layer is set to be ten times or less the number of the silicon atoms in the hole transport layer. It should be noted that the requirement is identical in meaning to the following: the relative ratio of the silicon atoms to the $SP^2$ carbon atoms in the hole transport layer is 10% or more.

Here, additionally increasing the relative ratio of the silicon atoms to the $SP^2$ carbon atoms in the hole transport layer makes the features (1-1) and (1-2) additionally conspicuous. Thus, the light emitting efficiency of the organic light emitting element additionally improves. Here, the improving effect on the light emitting efficiency is an effect exerted by the features (1-1) and (1-2). That is, the light emitting efficiency is improved by: an effect exerted by the feature (1-1) by which the probability that light emission caused in the emission layer is reabsorbed in, for example, the hole transport layer can be reduced; and an effect exerted by the feature (1-2) by which the trapping of an electron or exciton in the emission layer is enabled.

Therefore, the organic light emitting element of the present invention into which the following hole transport layer has been introduced has high light emitting efficiency: the siloxane compound and the compound having a tertiary arylamine structure are incorporated into the layer, and the number of the $SP^2$ carbon atoms in the layer is ten times or less the number of the silicon atoms in the hole transport layer. It should be noted that in the present invention, the number of the $SP^2$ carbon atoms in the hole transport layer is preferably set to be 6.67 times or less, i.e., twenty-third times or less the number of the silicon atoms in the hole transport layer.

Specific examples of the siloxane compound in the hole transport layer are shown below. However, the present invention is not limited to these specific examples.

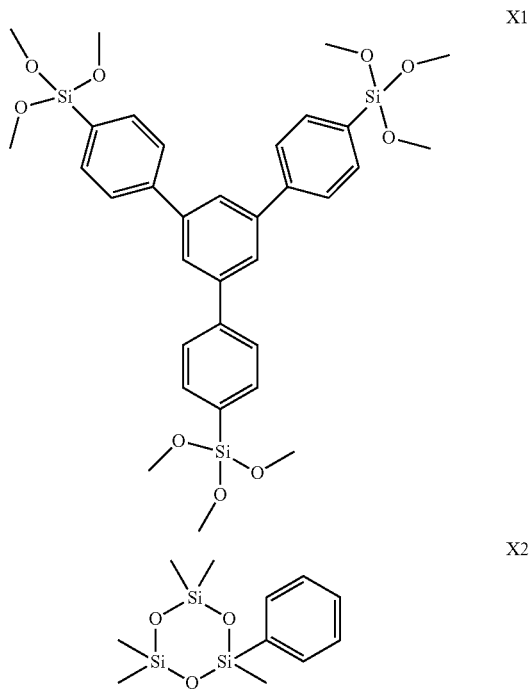

-continued
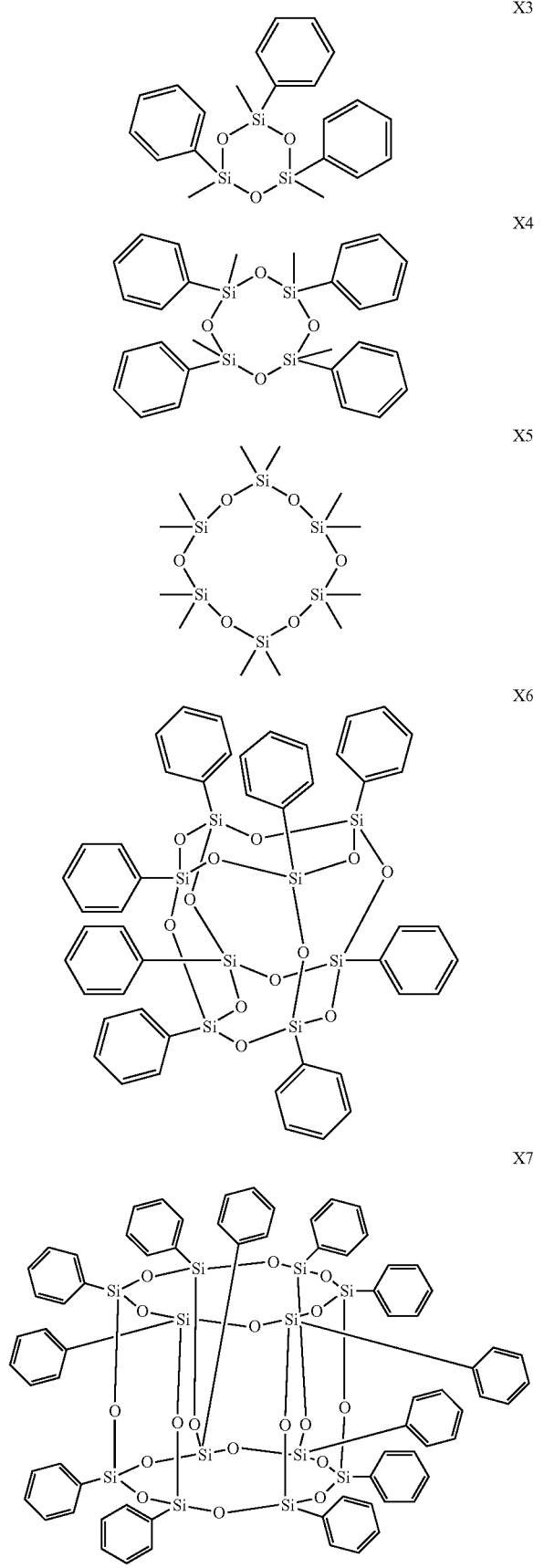
Next, specific examples of the tertiary arylamine compound in the hole transport layer are shown below, provided that the present invention is not limited to these specific examples.
[Specific Examples of the General Formula [27]]
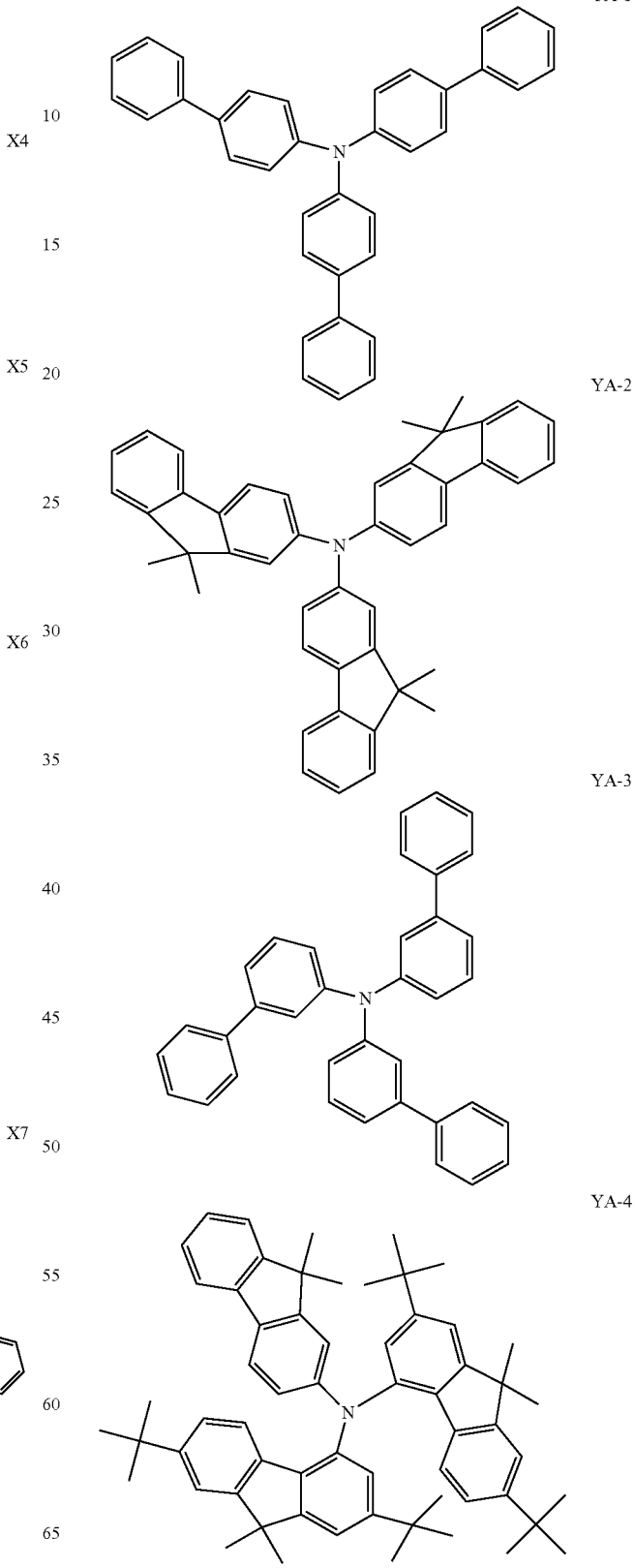

YA-5
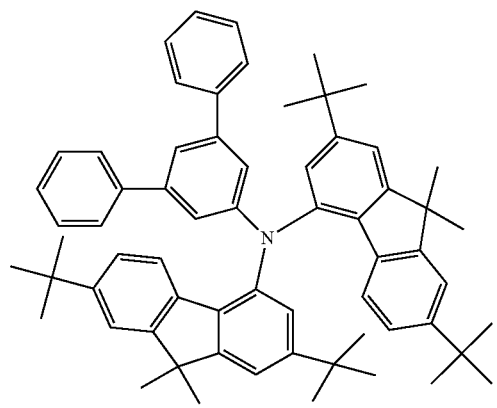
YA-7
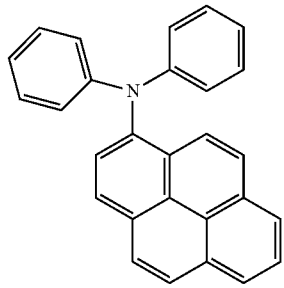
YA-6
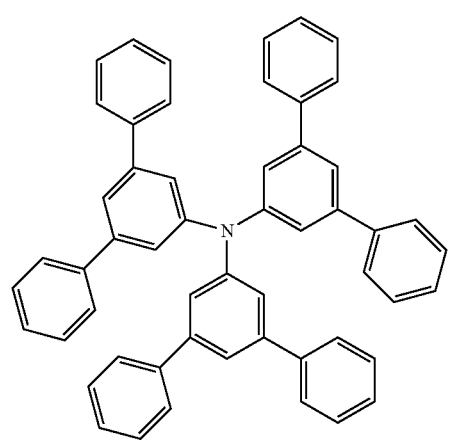
YA-8
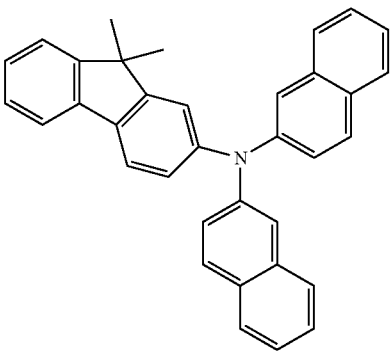
[Specific Examples of the General Formula [28]]
YB-1
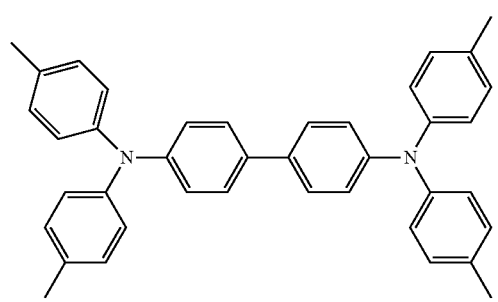
YB-2
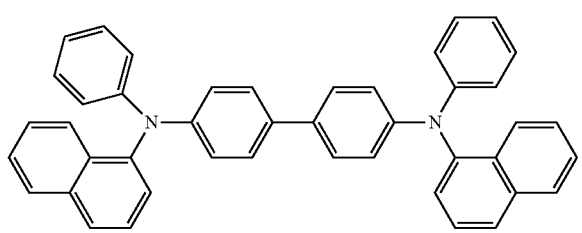
YB-3
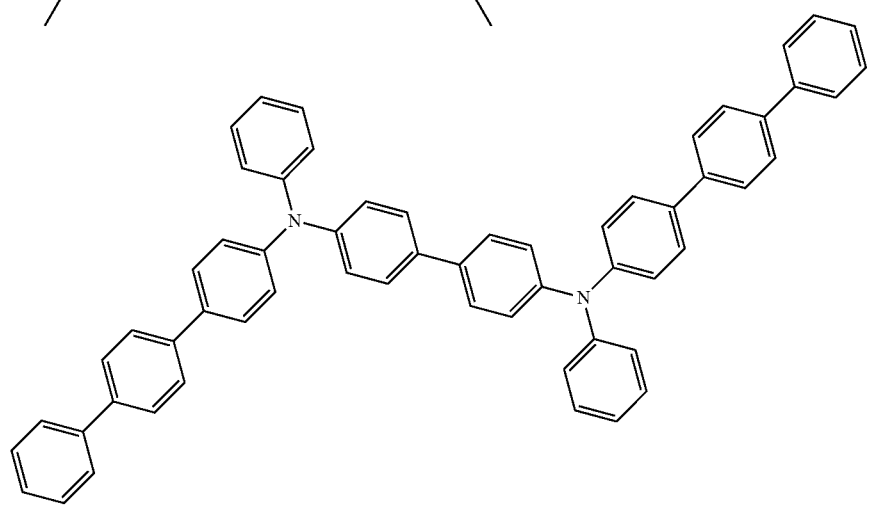

-continued
YB-4    YB-5
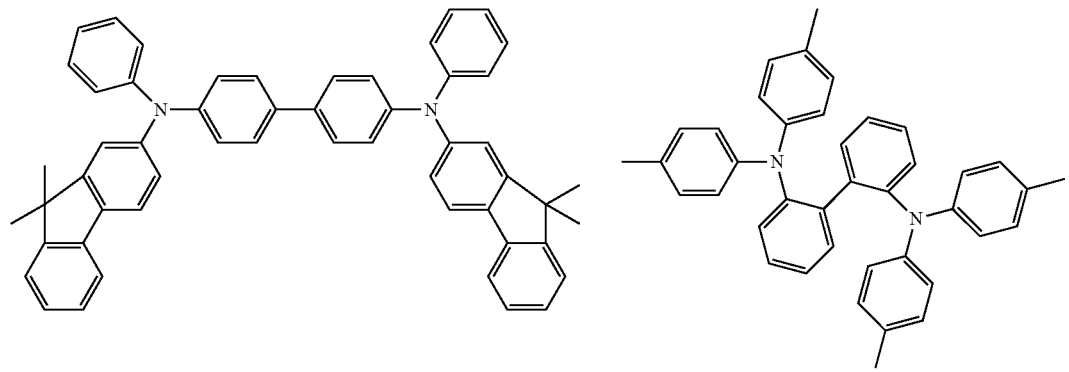
YB-6
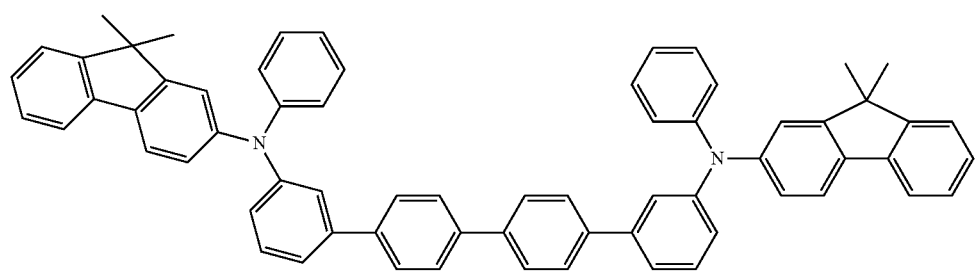
YB-7    YB-8
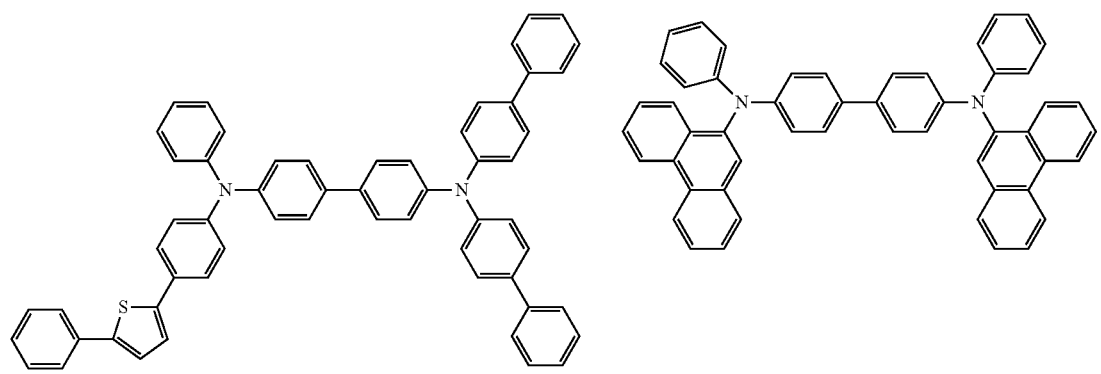
YB-9    YC-1
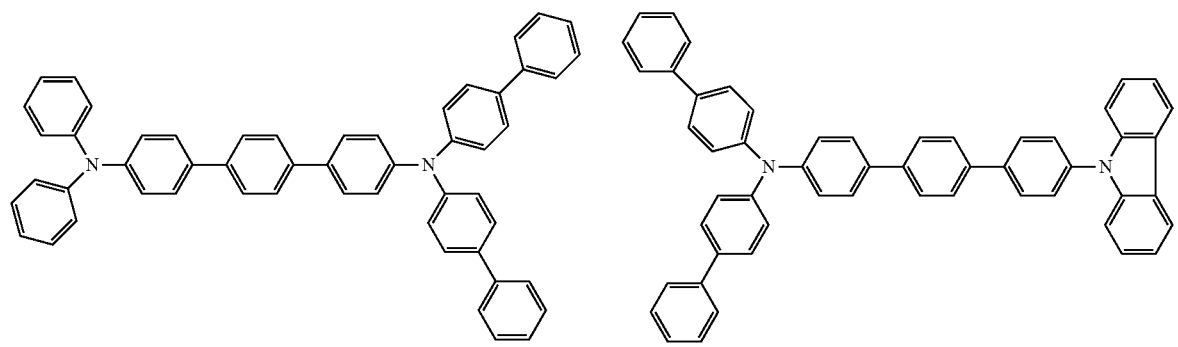

-continued
YC-2
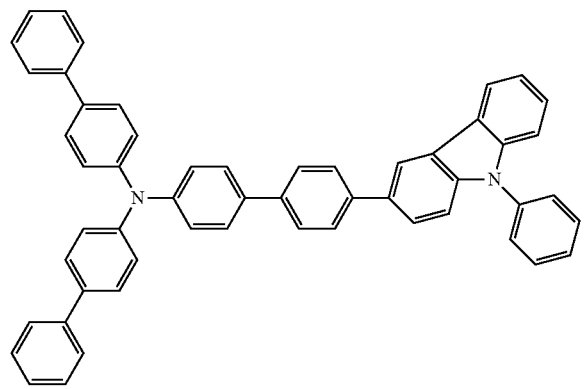
YC-3
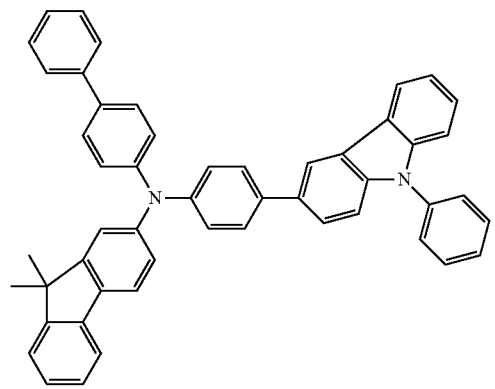
YC-4
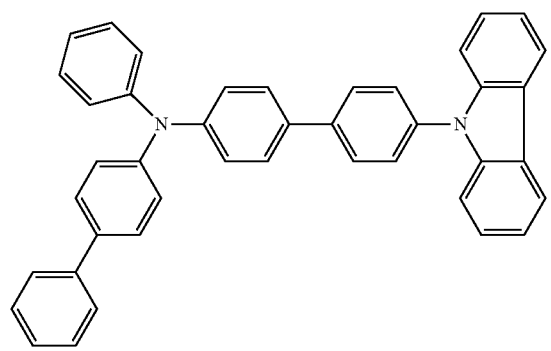
YC-5
YC-6
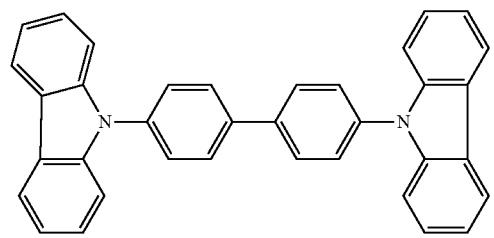
[Specific Examples of the General Formula [29]]
-continued
YD-1
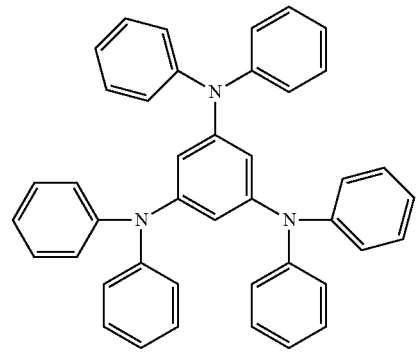
YD-2
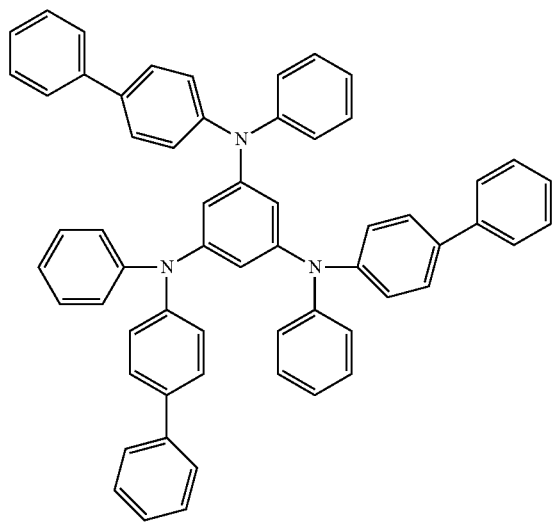

YD-3
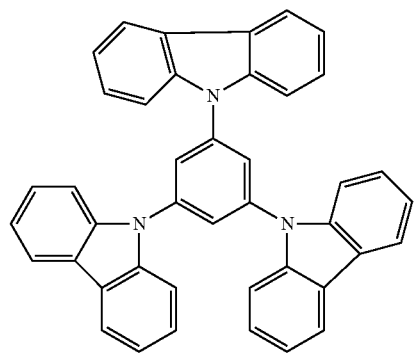
YE-2
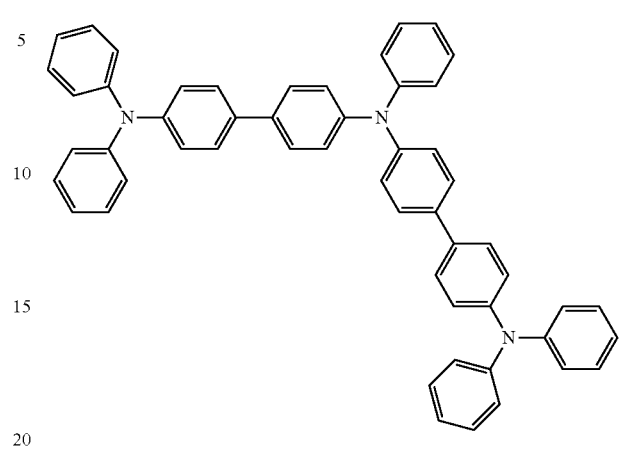
[Specific Examples of the General Formula [30]]
YE-1
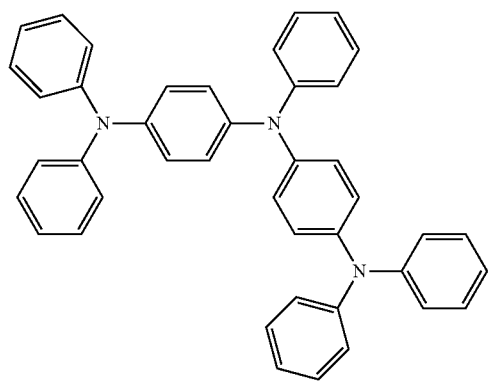
YE-3
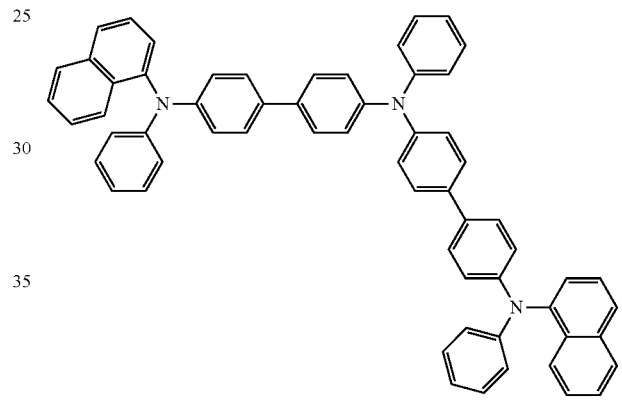
[Specific Examples of the General Formula [31]]
YF-1
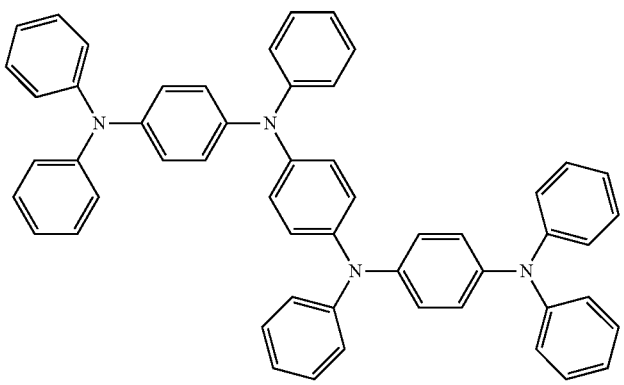

YF-2
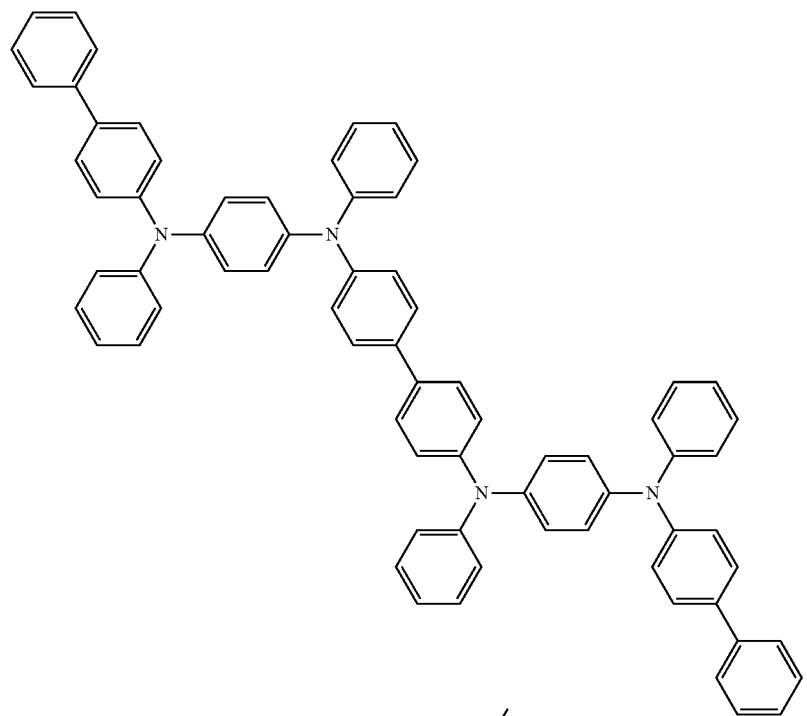
YF-3
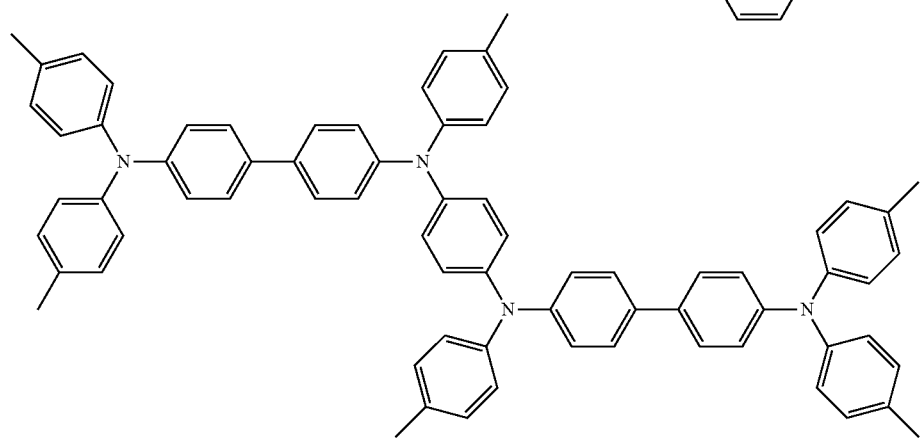
[Specific Examples of the General Formula [32]]
YG-1
YG-2
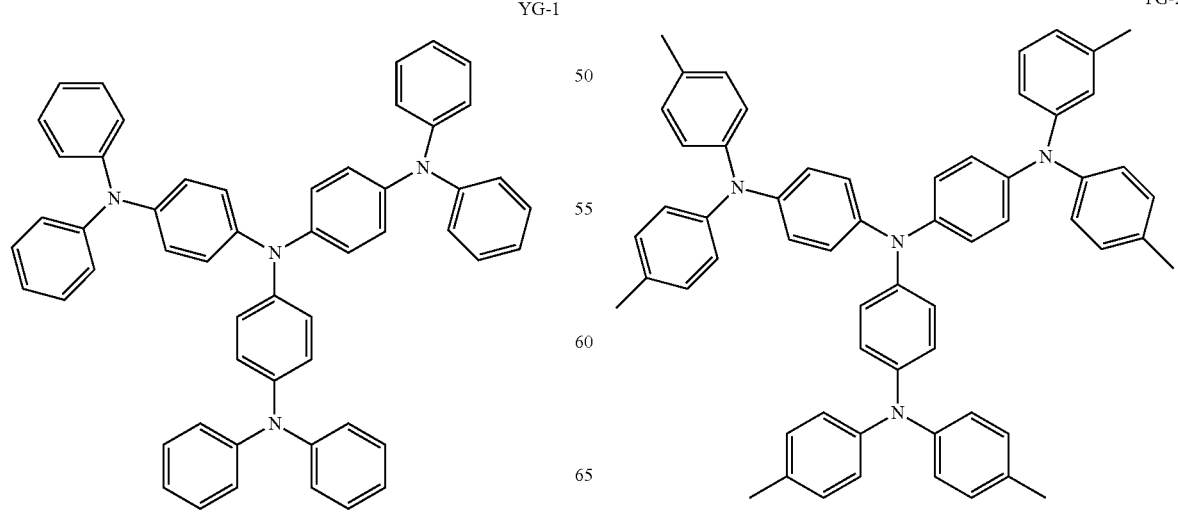

YG-3
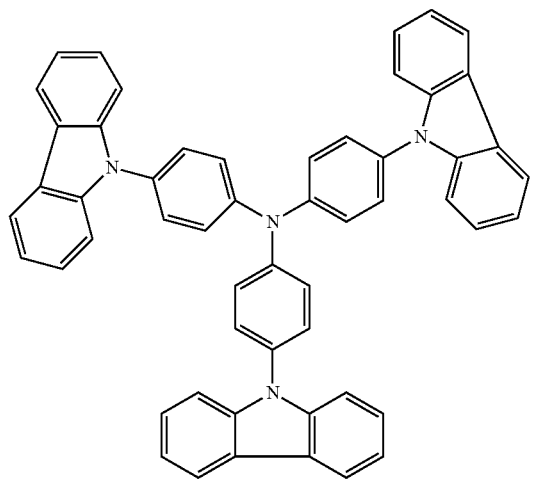
[Specific Examples of the General Formula [33]]
YH-1
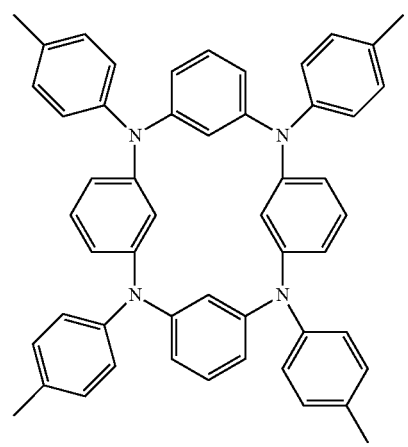
YH-2
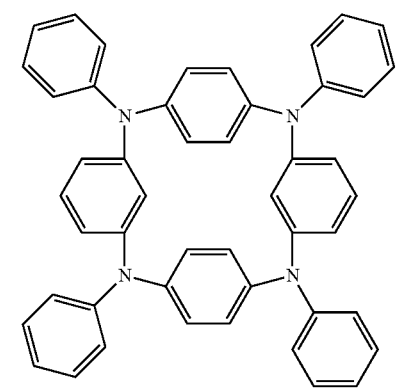
YH-3
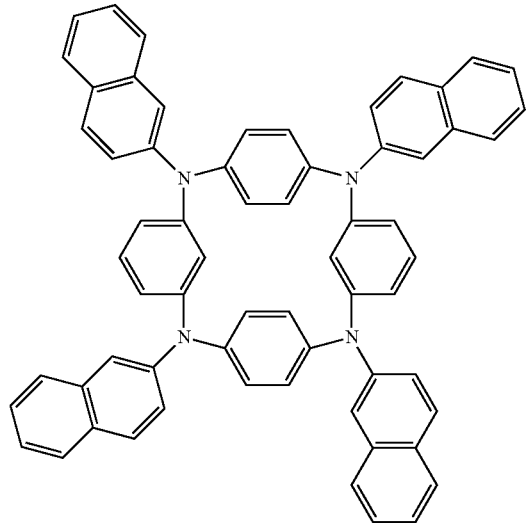
YH-4
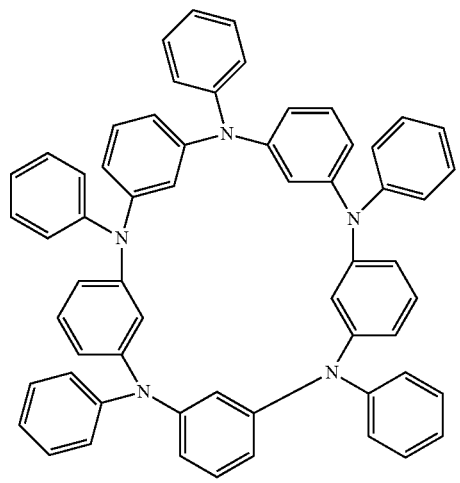
YH-5
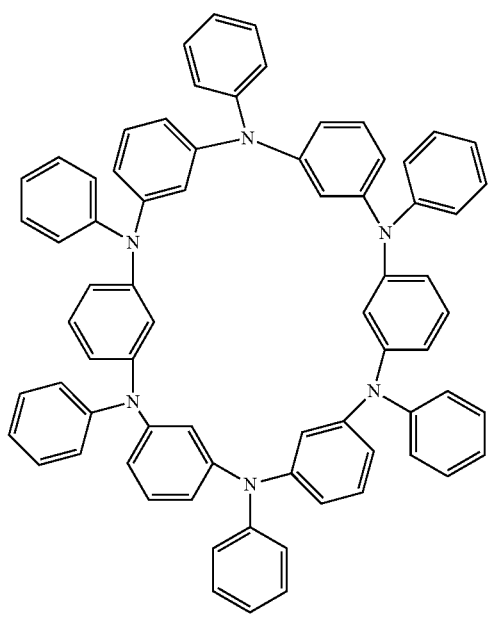

Specific Examples of Polymer Compound
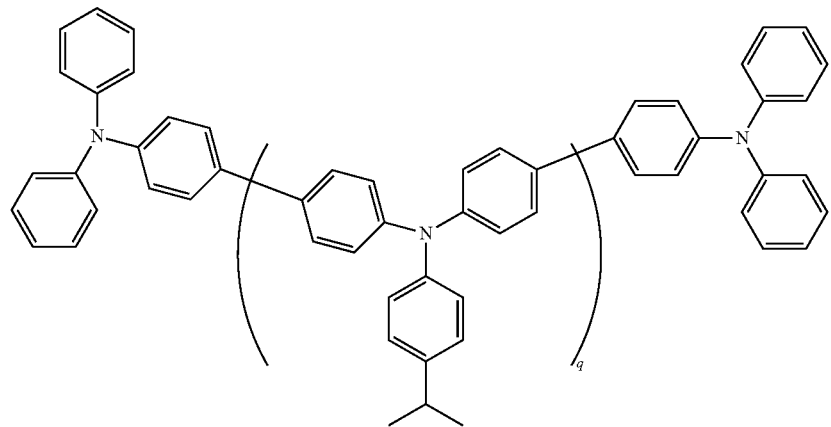
YI-1
(q represents an integer of 1 or more.)
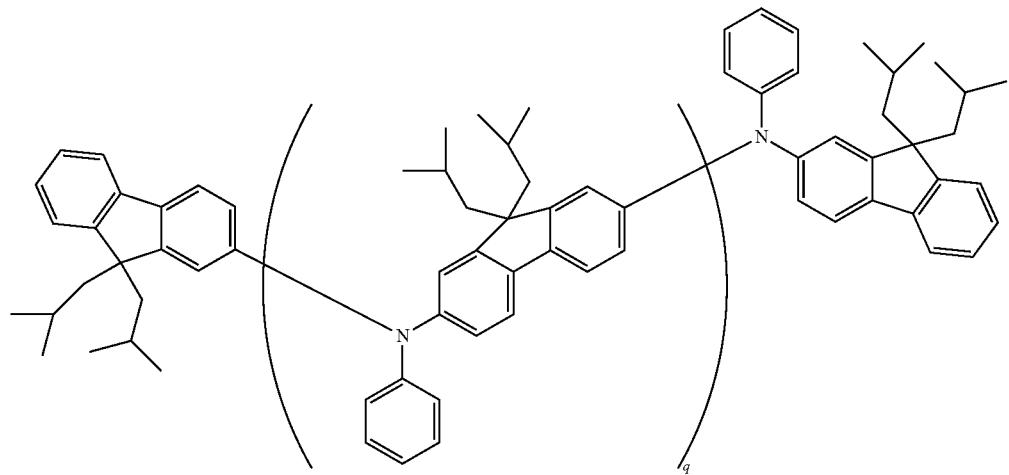
YI-2
(q represents an integer of 1 or more.)
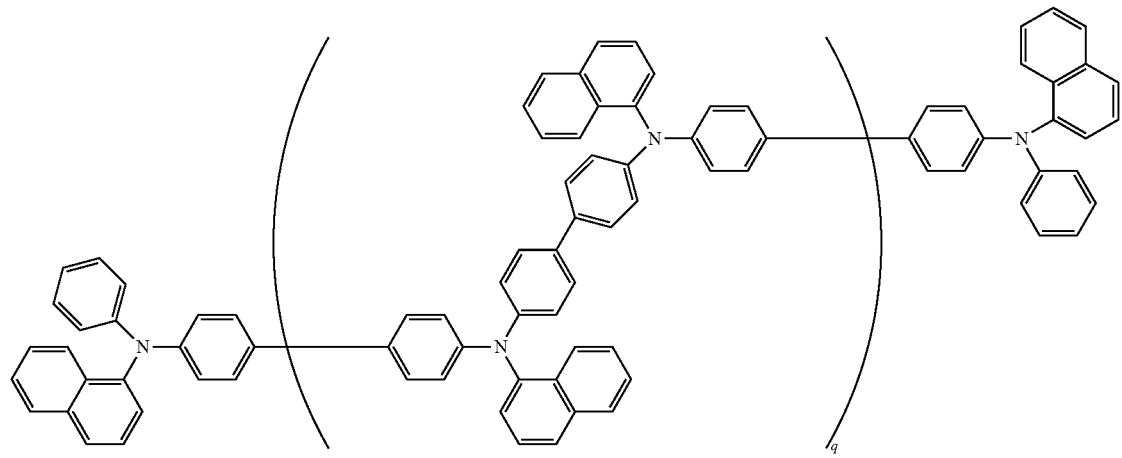
YI-3
(q represents an integer of 1 or more.)

The organic light emitting element of the present invention, in particular, the siloxane compound and the compound having a tertiary arylamine structure as main constituent materials have been described above, provided that the constituent materials for the organic light emitting element of the present invention are not limited to the siloxane compound and the compound having a tertiary arylamine structure. It should be noted that any other constituent material in the organic light emitting element of the present invention is separately described.

(2) Silsesquioxane Compound

Next, the silsesquioxane compound of the present invention is described. Specifically, the silsesquioxane compound of the present invention is a compound represented by any one of the following general formulae [1] to [3].

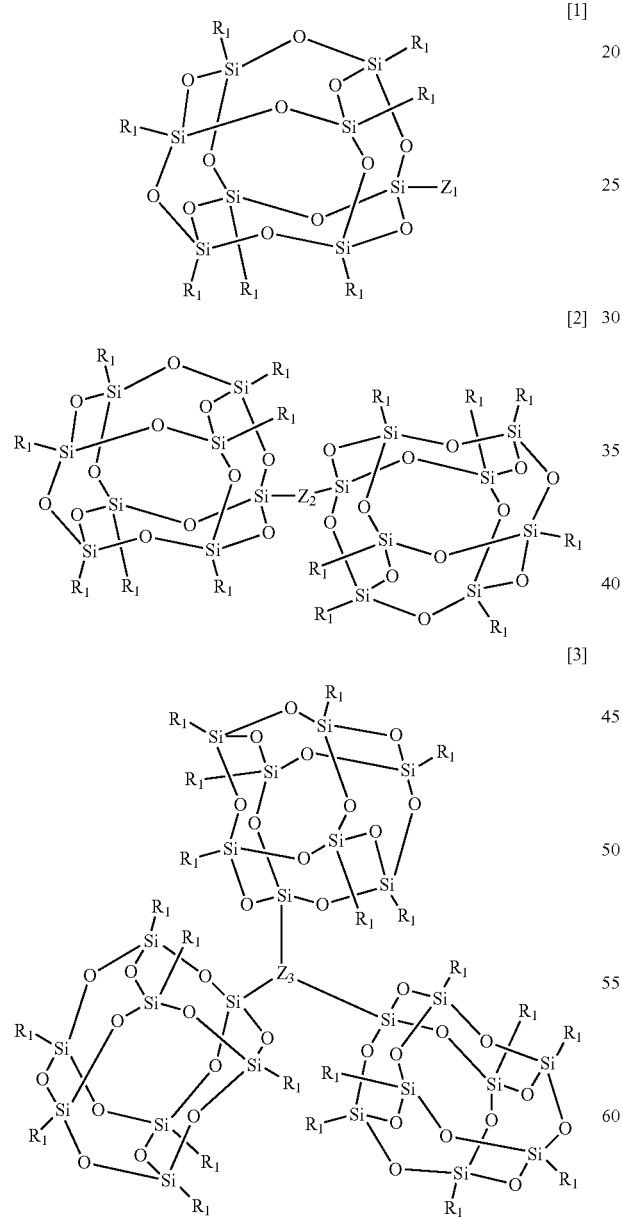

In the formulae [1] to [3], $R_1$ represent an alkyl group having 1 or more and 8 or less carbon atoms.

Examples of the alkyl group having 1 or more and 8 or less carbon atoms represented by $R_1$ include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, and a cyclooctyl group.

Multiple $R_1$'s in each of the formulae [1] to [3] may be identical to or different from each other.

In the formula [1], $Z_1$ represent a monovalent alkyl group having 1 to 8 carbon atoms, a unit represented by the following general formula [4A], or an aromatic amino group selected from the following general formulae [5] to [9].

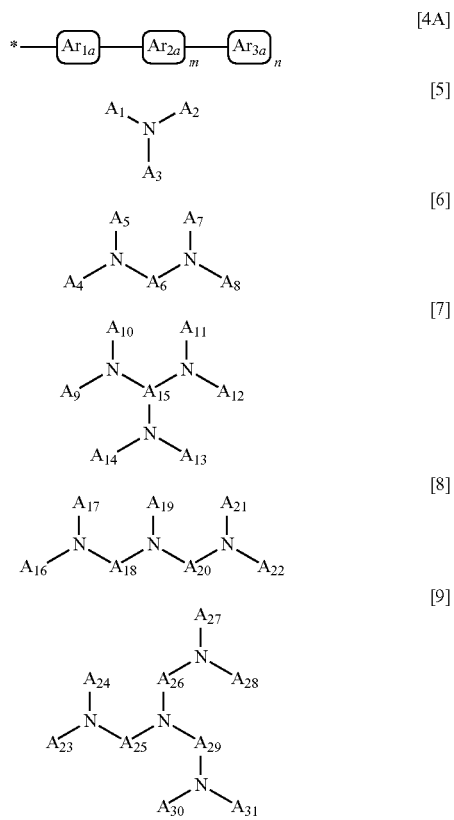

When $Z_1$ represents a monovalent alkyl group having 1 to 8 carbon atoms, specific examples of the alkyl group are the same as the specific examples of the alkyl group having 1 or more and 8 or less carbon atoms represented by $R_1$.

When $Z_1$ represent the unit represented by the general formula [4A], $Ar_{1a}$, $Ar_{2a}$, and $Ar_{3a}$ in the general formula [4A] each represent a substituted or unsubstituted aryl group. Examples of the aryl group represented by any one of $Ar_{1a}$, $Ar_{2a}$, and $Ar_{3a}$ include a phenyl group, biphenyl group, a terphenyl group, a naphthyl group, a phenanthrenyl group, a fluorenyl group, a triphenylenyl group, a chrysenyl group, and a pyrenyl group.

As a substituent that the aryl group may further have, there are given, for example: an alkyl group having 1 or more and 8 or less carbon atoms such as a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, or a cyclooctyl group; a phenoxy group that may have the alkyl group having 1 or more and 8 or less carbon atoms; and an alkoxy group such as methoxy group, an ethoxy group, a propoxy group, a butoxy group, a t-butoxy group, a hexyloxy group, an ethylhexyloxy group, or an octyloxy group.

When $Z_1$ represents a unit represented by the general formula [4A], * in the general formula [4A] represents a bonding hand with a silsesquioxane skeleton.

When $Z_1$ represents a unit represented by the general formula [4A], m and n in the general formula [4A] each represent 0 or 1, provided that n represents 0 when m represents 0.

When $Z_1$ represents an aromatic amino group represented by the general formula [5], $A_1$ to $A_3$ in the general formula [5] each represent a bonding hand with a silsesquioxane skeleton or a unit represented by the general formula [10A] to be described later.

When $Z_1$ represents an aromatic amino group represented by the general formula [6], $A_4$, $A_5$, $A_7$, and $A_8$ in the general formula [6] each represent a bonding hand with a silsesquioxane skeleton or a unit represented by the general formula [10A] to be described later.

When $Z_1$ represents an aromatic amino group represented by the general formula [6], $A_6$ in the general formula [6] represents a unit represented by any one of the general formulae [10B] to [10D] to be described later.

When $Z_1$ represents an aromatic amino group represented by the general formula [7], $A_9$ to $A_{14}$ in the general formula [7] each represent a bonding hand with a silsesquioxane skeleton or a unit represented by the general formula [10A] to be described later.

When $Z_1$ represents an aromatic amino group represented by the general formula [7], $A_{15}$ in the general formula [7] represents a unit represented by any one of the general formulae [10E] to [10G] to be described later.

When $Z_1$ represents an aromatic amino group represented by the general formula [8], $A_{16}$, $A_{17}$, $A_{19}$, $A_{21}$, and $A_{22}$ in the general formula [8] each represent a bonding hand with a silsesquioxane skeleton or a unit represented by the general formula [10A] to be described later.

When $Z_1$ represents an aromatic amino group represented by the general formula [8], $A_{18}$ and $A_{20}$ in the general formula [8] each represent a unit represented by any one of the general formulae [10B] to [10D] to be described later.

When $Z_1$ represents an aromatic amino group represented by the general formula [9], $A_{23}$, $A_{24}$, $A_{27}$, $A_{28}$, $A_{30}$, and $A_{31}$ in the general formula [9] each represent a bonding hand with a silsesquioxane skeleton or a unit represented by the general formula [10A] to be described later.

When $Z_1$ represents an aromatic amino group represented by the general formula [9], $A_{25}$, $A_{26}$, and $A_{29}$ in the general formula [9] each represent a unit represented by any one of the general formulae [10B] to [10D] to be described later.

Next, the units represented by the following general formulae [10A] to [10G] are described.

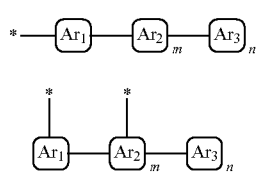

[10A]

[10B]

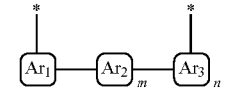 [10C]

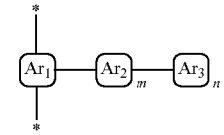 [10D]

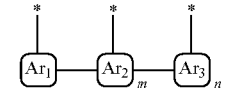 [10E]

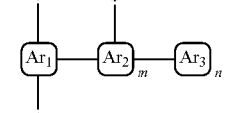 [10F]

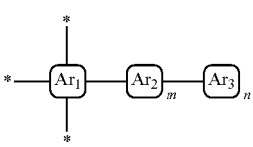 [10G]

In the general formulae [10A] to [10G], $Ar_1$ to $Ar_3$ each represent a substituted or unsubstituted aryl group. Specific examples of the aryl group represented by any one of $Ar_1$ to $Ar_3$ and a substituent which the aryl group may further have are the same as the specific examples of $Ar_{1a}$, $Ar_{2a}$, and $Ar_{3a}$ in the general formula [4A].

In the general formulae [10A] to [10G], ⋇ represents a bonding hand with an N atom.

In the general formulae [10A] to [10G], m and n each represent 0 or 1, provided that n represents 0 when m represents 0.

In the formula [2], $Z_2$ represents a divalent alkyl group having 1 to 8 carbon atoms, a unit represented by any one of the following general formulae [4B] to [4D], or an aromatic amino group selected from the following general formulae [5] to [9].

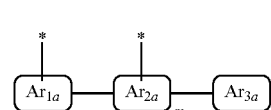 [4B]

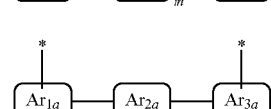 [4C]

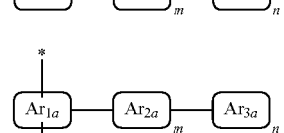 [4D]

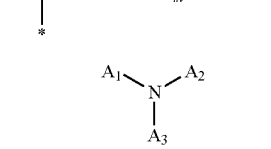 [5]

-continued

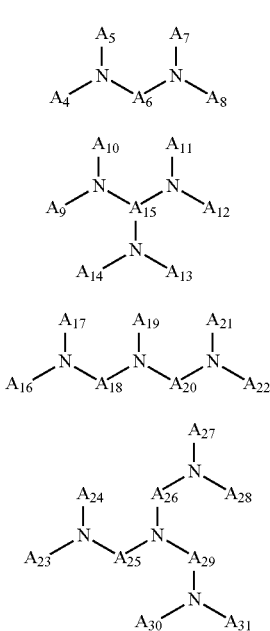

[6]

[7]

[8]

[9]

When $Z_2$ represents a divalent alkyl group having 1 or more and 8 or less carbon atoms, a specific example of the divalent alkyl group is a divalent substituent originating from a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, or a cyclooctyl group.

When $Z_2$ represents a unit represented by any one of the general formulae [4B] to [4D], $Ar_{1a}$, $Ar_{2a}$, and $Ar_{3a}$ in the general formulae [4B] to [4D] each represent a substituted or unsubstituted aryl group. It should be noted that specific examples of the aryl group represented by any one of $Ar_{1a}$, $Ar_{2a}$, and $Ar_{3a}$, and a substituent which the aryl group may further have are the same as the specific examples of $Ar_{1a}$, $Ar_{2a}$, and $Ar_{3a}$ in the general formula [4A].

When $Z_2$ represents a unit represented by any one of the general formulae [4B] to [4D], * represents a bonding hand with a silsesquioxane skeleton.

When $Z_2$ represents a unit represented by any one of the general formulae [4B] to [4D], m and n each represent 0 or 1, provided that n represents 0 when m represents 0.

When $Z_2$ represents an aromatic amino group represented by the general formula [5], $A_1$ to $A_3$ in the general formula [5] each represent a bonding hand with a silsesquioxane skeleton or a unit represented by the general formula [10A].

When $Z_2$ represents an aromatic amino group represented by the general formula [6], $A_4$, $A_5$, $A_7$, and $A_8$ in the general formula [6] each represent a bonding hand with a silsesquioxane skeleton or a unit represented by the general formula [10A].

When $Z_2$ represents an aromatic amino group represented by the general formula [6], $A_6$ in the general formula [6] represents a unit represented by any one of the general formulae [10B] to [10D].

When $Z_2$ represents an aromatic amino group represented by the general formula [7], $A_9$ to $A_{14}$ in the general formula [7] each represent a bonding hand with a silsesquioxane skeleton or a unit represented by the general formula [10A].

When $Z_2$ represents an aromatic amino group represented by the general formula [7], $A_{15}$ in the general formula [7] represents a unit represented by any one of the general formulae [10E] to [10G].

When $Z_2$ represents an aromatic amino group represented by the general formula [8], $A_{16}$, $A_{17}$, $A_{19}$, $A_{21}$, and $A_{22}$ in the general formula [8] each represent a bonding hand with a silsesquioxane skeleton or a unit represented by the general formula [10A].

When $Z_2$ represents an aromatic amino group represented by the general formula [8], $A_{18}$ and $A_{20}$ in the general formula [8] each represent a unit represented by any one of the general formulae [10B] to [10D].

When $Z_2$ represents an aromatic amino group represented by the general formula [9], $A_{23}$, $A_{24}$, $A_{27}$, $A_{28}$, $A_{30}$, and $A_{31}$ in the general formula [9] each represent a bonding hand with a silsesquioxane skeleton or a unit represented by the general formula [10A].

When $Z_2$ represents an aromatic amino group represented by the general formula [9], $A_{25}$, $A_{26}$, and $A_{29}$ in the general formula [9] each represent a unit represented by any one of the general formulae [10B] to [10D].

When $Z_2$ represents any one of the aromatic amino groups represented by the general formulae [5] to [9], the units represented by the general formulae [10A] to [10G] that can be incorporated into the aromatic amino group are each a unit shown below.

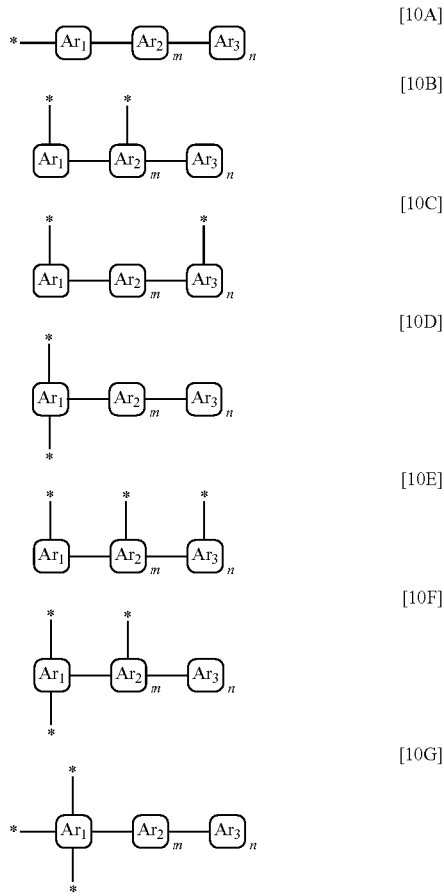

It should be noted that details about the group of units (group of units represented by the general formulae [10A] to [10G]) are the same as those about the units represented by the general formulae [10A] to [10G] that can be incorporated into $Z_1$ in the general formula [1].

In the formula [3], $Z_3$ represents a trivalent alkyl group having 1 to 8 carbon atoms, a unit represented by any one of the following general formulae [4E] to [4G], or an aromatic amino group selected from the following general formulae [5] to [9].

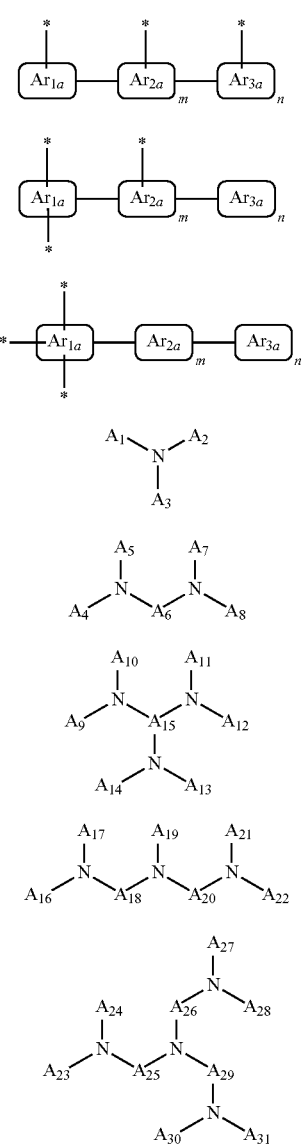

When $Z_3$ represents a trivalent alkyl group having 1 or more and 8 or less carbon atoms, a specific example of the trivalent alkyl group is a trivalent substituent originating from a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, or a cyclooctyl group.

When $Z_3$ represents a unit represented by any one of the general formulae [4E] to [4G], $Ar_{1a}$, $Ar_{2a}$, and $Ar_{3a}$ in the general formulae [4E] to [4G] each represent a substituted or unsubstituted aryl group. It should be noted that specific examples of the aryl group represented by any one of $Ar_{1a}$, $Ar_{2a}$, and $Ar_{3a}$, and a substituent which the aryl group may further have are the same as the specific examples of $Ar_{1a}$, $Ar_{2a}$, and $Ar_{3a}$ in the general formula [4A].

When $Z_3$ represents a unit represented by any one of the general formulae [4E] to [4G], * in the general formulae [4E] to [4G] represents a bonding hand with a silsesquioxane skeleton.

When $Z_3$ represents a unit represented by any one of the general formulae [4E] to [4G], m and n in the general formulae [4E] to [4G] each represent 0 or 1, provided that n represents 0 when m represents 0.

When $Z_3$ represents an aromatic amino group represented by the general formula [5], $A_1$ to $A_3$ in the general formula [5] each represent a bonding hand with a silsesquioxane skeleton.

When $Z_3$ represents an aromatic amino group represented by the general formula [6], $A_4$, $A_5$, $A_7$, and $A_8$ in the general formula [6] each represent a bonding hand with a silsesquioxane skeleton or a unit represented by the general formula [10A].

When $Z_3$ represents an aromatic amino group represented by the general formula [6], $A_6$ in the general formula [6] represents a unit represented by any one of the general formulae [10B] to [10D].

When $Z_3$ represents an aromatic amino group represented by the general formula [7], $A_9$ to $A_{14}$ in the general formula [7] each represent a bonding hand with a silsesquioxane skeleton or a unit represented by the general formula [10A].

When $Z_3$ represents an aromatic amino group represented by the general formula [7], $A_{15}$ in the general formula [7] represents a unit represented by any one of the general formulae [10E] to [10G].

When $Z_3$ represents an aromatic amino group represented by the general formula [8], $A_{16}$, $A_{17}$, $A_{19}$, $A_{21}$, and $A_{22}$ in the general formula [8] each represent a bonding hand with a silsesquioxane skeleton or a unit represented by the general formula [10A].

When $Z_3$ represents an aromatic amino group represented by the general formula [8], $A_{18}$ and $A_{20}$ in the general formula [8] each represent a unit represented by any one of the general formulae [10B] to [10D].

When $Z_3$ represents an aromatic amino group represented by the general formula [9], $A_{23}$, $A_{24}$, $A_{27}$, $A_{28}$, $A_{30}$, and $A_{31}$ in the general formula [9] each represent a bonding hand with a silsesquioxane skeleton or a unit represented by the general formula [10A].

When $Z_3$ represents an aromatic amino group represented by the general formula [9], $A_{25}$, $A_{26}$, and $A_{29}$ in the general formula [9] each represent a unit represented by any one of the general formulae [10B] to [10D].

When $Z_3$ represents any one of the aromatic amino groups represented by the general formulae [6] to [9], the units represented by the general formulae [10A] to [10G] that can be incorporated into the aromatic amino group are each a unit shown below.

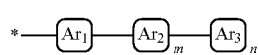

[10A]

-continued

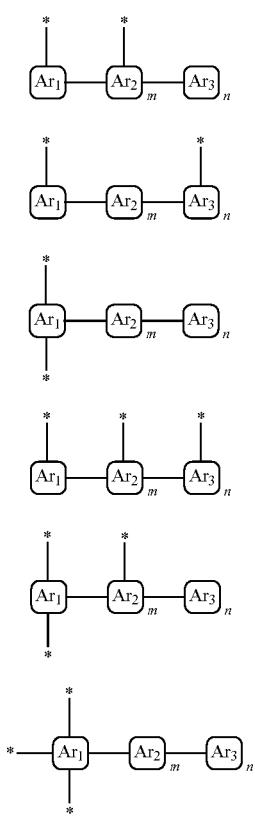

It should be noted that details about the group of units (group of units represented by the general formulae [10A] to [10G]) are the same as those about the units represented by the general formulae [10A] to [10G] that can be incorporated into $Z_1$ in the general formula [1].

Here, the silsesquioxane compound represented by any one of the general formulae [1] to [3] is such that a molecular unit containing Si—O—Si (silsesquioxane unit) is of a cage-like structure. Accordingly, each silsesquioxane unit has high stability and a space can be provided in the cage-like structure, whereby the absorbance can be reduced and the band gap can be widened.

Next, the features of the silsesquioxane compound represented by any one of the general formulae [1] to [3] are described. The silsesquioxane compound represented by any one of the general formulae [1] to [3] has the following structural features (2-1) and (2-2): (2-1) all substituents $R_1$'s of a silsesquioxane unit are each an alkyl group having 1 or more and 8 or less carbon atoms; and (2-2) a substituent unit Z containing an aryl group substitutes at one position.

The compound exerts two effects described below because the compound has the features.

A first effect is that solubility in an organic solvent improves. In general, an alkyl group has higher solubility in an organic solvent than that of an aromatic substituent (such as an aryl group) showing strong intermolecular stacking in a solid state. Therefore, the silsesquioxane compound of the present invention has higher solubility in an organic solvent than that of each of Compound a-1 and Compound b-1 described in PTL 1. Accordingly, handleability at the time of its synthesis is good and crystallization hardly occurs when the compound is brought into a thin-film state.

A second effect is that the absorbance at the maximum absorption wavelength reduces and a band gap in a thin-film state widens. The effect results from the fact that one or more silsesquioxane units are substituted with the only one substituent unit $Z_1$, $Z_2$, or $Z_3$ that can include an aryl group. By the way, most of the aryl groups are each a substituent having absorption in the visible region and showing a large stack interaction. In contrast, the silsesquioxane unit is a molecular unit having no absorption in the visible region. The silsesquioxane compound of the present invention has a larger ratio of a silsesquioxane unit than those of Compound a-1 and Compound b-1 described in PTL 1. Accordingly, when the silsesquioxane compound of the present invention is formed into a thin film, the absorbance at the maximum absorption wavelength reduces and an additionally wide band gap can be maintained.

By virtue of the two effects described above, when the silsesquioxane compound of the present invention is used as a constituent material for the organic light emitting element, the absorbance of the compound itself is low and hence light generated in the emission layer can be extracted to the outside without being absorbed by the silsesquioxane compound of the present invention. Further, an electron or exciton can be trapped in the emission layer by the wide band gap of the silsesquioxane compound of the present invention, and hence the light emitting efficiency improves.

Here, the silsesquioxane compound of the present invention has a partial structure, i.e., the substituent unit $Z_1$, $Z_2$, or $Z_3$, and these substituent units are roughly classified into the following two partial structures: (2-3) a partial structure free of an arylamine structure; and (2-4) a partial structure containing an arylamine structure.

Hereinafter, the features (2-3) and (2-4) are described.

<When $Z_1$, $Z_2$, or $Z_3$ is Partial Structure Free of Arylamine Structure>

When $Z_1$, $Z_2$, or $Z_3$ represents an alkyl group having 1 to 8 carbon atoms, or represents any one of the general formulae [4A] to [4G], the partial structure represented by $Z_1$, $Z_2$, or $Z_3$ corresponds to the partial structure described in the feature (2-3). In this case, the case where $Z_1$, $Z_2$, or $Z_3$ represents any one of the general formulae [4A] to [4G] is preferred.

When $Z_1$, $Z_2$, or $Z_3$ represents any one of the general formulae [4A] to [4G], a phenyl group, a biphenyl group, a terphenyl group, a naphthyl group, or a fluorenyl group is particularly preferred as an aryl group in any one of the general formulae [4A] to [4G] ($Ar_{1a}$, $Ar_2$, $Ar_{3a}$). Those substituents are each such a substituent that the number of condensed rings of aromatic rings forming an aryl group is two or less. In addition, those substituents are each a substituent having a wider band gap than that of such an aryl group that the number of condensed rings of aromatic rings forming the aryl group is three or more, e.g., a phenanthrenyl group, a triphenylenyl group, a chrysenyl group, or a pyrenyl group.

It should be noted that a state where the band gap is wide can be maintained even when the aryl group further has an alkyl group having 1 or more and 8 or less carbon atoms, a phenoxy group that may have an alkyl group having 1 or more and 8 or less carbon atoms, or an alkoxy group having 1 or more and 8 or less carbon atoms.

Here, the ratio of the silsesquioxane unit to an entire molecule increases as the number of condensed rings, or the linking number of aromatic rings, of the aryl group ($Ar_{1a}$, $Ar_{2a}$, or $Ar_{3a}$) in any one of the general formulae [4A] to [4G] reduces. As a result, the absorbance at the maximum absorption wavelength reduces and the band gap widens.

In view of the foregoing, out of the compounds each having the feature (2-3), a silsesquioxane compound represented by any one of the following general formula [11] and the following general formula [12] is preferred.

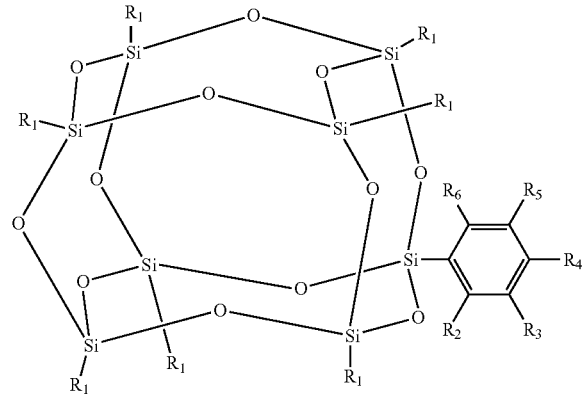

[11]

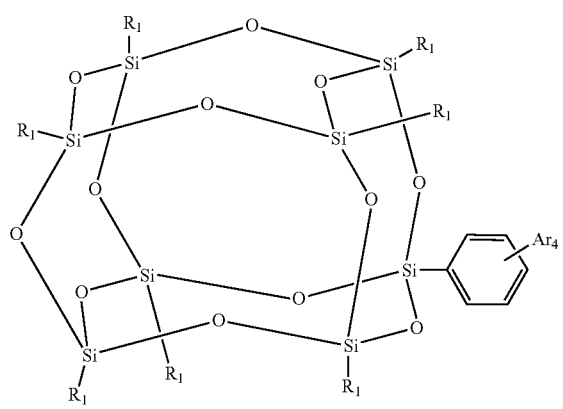

[12]

In the general formulae [11] and [12], $R_1$ represents an alkyl group having 1 or more and 8 or less carbon atoms. Specific examples of the alkyl group represented by $R_1$ are the same as those of $R_1$ in the general formula [1]. In addition, multiple $R_1$'s represented in each of the formulae [11] and [12] may be identical to or different from each other.

In the general formula [11], $R_2$ to $R_6$ each represent a hydrogen atom or an alkyl group or alkoxy group having 1 to 8 carbon atoms.

Examples of the alkyl group having 1 or more and 8 or less carbon atoms represented by any one of $R_2$ to $R_6$ include a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, and a cyclooctyl group.

Examples of the alkoxy group represented by any one of $R_2$ to $R_6$ include a methoxy group, an ethoxy group, a propoxy group, a butoxy group, a t-butoxy group, a hexyloxy group, an ethylhexyloxy group, and an octyloxy group.

In the general formula [12], $Ar_4$ represents a substituted or unsubstituted aryl group.

An example of the aryl group represented by $Ar_4$ is a substituent selected from a phenyl group, a biphenyl group, a terphenyl group, a naphthyl group, and a fluorenyl group.

As a substituent that the aryl group may further have, there are given, for example: an alkyl group having 1 or more and 8 or less carbon atoms such as a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, or a cyclooctyl group; a phenoxy group that may have the alkyl group having 1 or more and 8 or less carbon atoms; and an alkoxy group such as a methoxy group, an ethoxy group, a propoxy group, a butoxy group, a t-butoxy group, a hexyloxy group, an ethylhexyloxy group, or an octyloxy group.

In addition, the silsesquioxane compound having the feature (2-3) is constituted of a substituent stable to oxidation and hence has a feature that the compound has strong resistance to oxidation.

In the organic light emitting element, the organic compound in the organic light emitting element repeatedly undergoes oxidation and reduction upon transfer of a hole or an electron in the organic compound layer. Accordingly, stability (resistance) to the oxidation and reduction that occur at the time of the transfer of the hole or the electron is important. Therefore, the use of the silsesquioxane compound having the feature (2-3) as a constituent material for the organic light emitting element improves the durability of the organic light emitting element against continuous light emission.

<When $Z_1$, $Z_2$, or $Z_3$ is Partial Structure Containing Arylamine Structure>

A silsesquioxane compound having the feature (2-4) is such that $Z_1$, $Z_2$, or $Z_3$ represents a partial structure represented by any one of the general formulae [5] to [9]. In this case, aryl groups represented by $Ar_1$ to $Ar_3$ that can be incorporated into $Z_1$, $Z_2$, and $Z_3$ are each preferably a phenyl group, a biphenyl group, a terphenyl group, a naphthyl group, or a fluorenyl group. It is because a wide band gap is obtained as in the case of the silsesquioxane compound having the feature (2-3) that any such substituent is suitably selected.

It should be noted that a state where the band gap is wide can be maintained even when a substituent suitable as the aryl group further has an alkyl group having 1 or more and 8 or less carbon atoms.

Here, the ratio of the silsesquioxane unit to the entire molecule increases as the number of condensed rings, or the linking number of aromatic rings, of the aryl group ($Ar_1$, $Ar_2$, or $Ar_3$) that can be incorporated into any one of the general formulae [5] to [9] reduces. As a result, the absorbance at the maximum absorption wavelength reduces and the band gap widens.

In view of the foregoing, out of the compounds each having the feature (2-4), a silsesquioxane compound represented by any one of the following general formula [13] to the following general formula [15] is preferred.

[13]

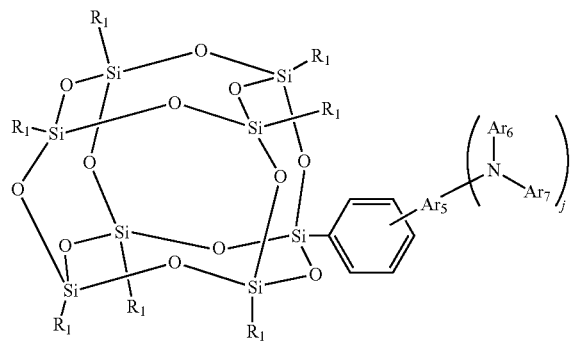

[14]

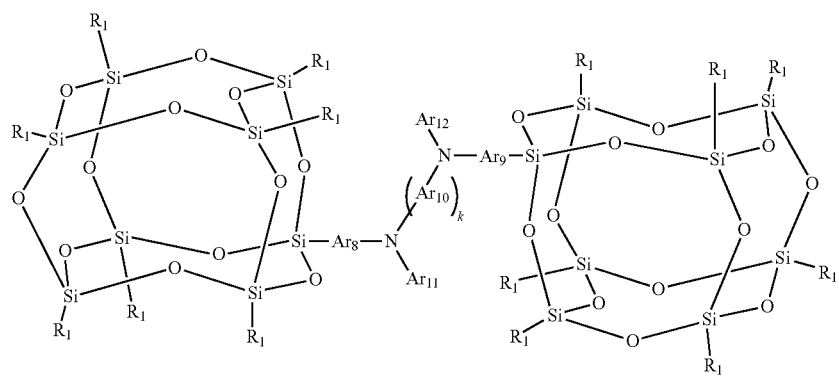

[15]

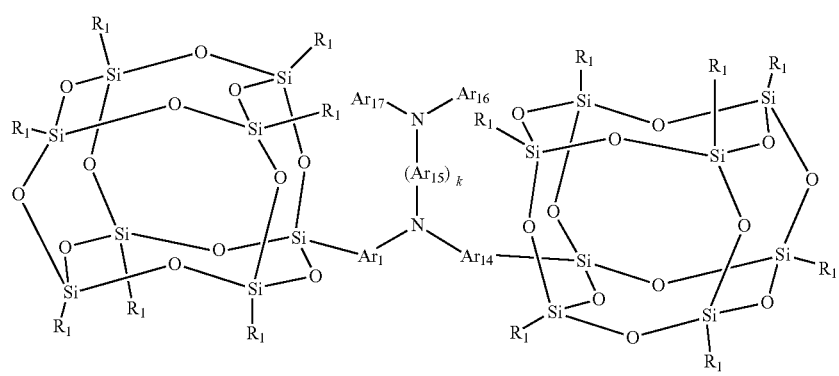

In the general formulae [13] to [15], $R_1$ represents an alkyl group having 1 or more and 8 or less carbon atoms. Specific examples of the alkyl group represented by $R_1$ are the same as those of $R_1$ in the general formula [1]. In addition, multiple $R_1$'s represented in each of the general formulae [13] to [15] may be identical to or different from each other.

In the general formula [13], j represents an integer of 1 to 3.

In the general formula [13], $Ar_5$ represents a substituted or unsubstituted, (j+1)-valent arylene group. The arylene group represented by $Ar_5$ is a (j+1)-valent substituent derived from a substituent selected from a phenylene group, a biphenylene group, a terphenylene group, a naphthylene group, and a fluorenylene group.

A substituent that the arylene group represented by $Ar_5$ may further have is, for example, an alkyl group having 1 or more and 8 or less carbon atoms such as a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, or a cyclooctyl group.

In the general formula [13], $Ar_6$ and $Ar_7$ each represent a substituted or unsubstituted aryl group. Each of the aryl groups represented by $Ar_6$ and $Ar_7$ is a substituent selected from a phenyl group, a biphenyl group, a terphenyl group, a naphthyl group, and a fluorenyl group.

A substituent that the aryl group represented by any one of $Ar_6$ and $Ar_7$ may have is, for example, an alkyl group having 1 or more and 8 or less carbon atoms such as a methyl group, an ethyl group, an n-propyl group, an isopropyl group, an n-butyl group, an isobutyl group, an s-butyl group, a t-butyl group, an n-pentyl group, an n-hexyl group, an n-heptyl group, an n-octyl group, an isobutyl group, a dimethylbutyl group, an ethylhexyl group, a cyclopentyl group, a cyclohexyl group, a cycloheptyl group, or a cyclooctyl group.

In the general formula [13], when j represents 2 or more, multiple $Ar_6$'s and multiple $Ar_7$'s may be identical to or different from each other.

In the general formulae [14] and [15], k represents 1 or 2.

In the general formula [14], $Ar_8$ to $Ar_{10}$ each represent a substituted or unsubstituted, divalent arylene group. Each of the divalent arylene groups represented by $Ar_8$ to $Ar_{10}$ is a substituent selected from a phenylene group, a biphenylene group, a terphenylene group, a naphthylene group, and a fluorenylene group. It should be noted that two $Ar_{10}$'s that present in the case where k represents 2 may be identical to or different from each other.

In the general formula [14], $Ar_{11}$ and $Ar_{12}$ each represent a substituted or unsubstituted aryl group. Specific examples of the monovalent aryl group represented by any one of $Ar_{11}$ and $Ar_{12}$ are the same as the specific examples of the aryl group represented by any one of $Ar_5$ to $Ar_7$ in the general formula [13].

In addition, in the general formula [14], specific examples of a substituent which $Ar_8$ to $Ar_{12}$ may each further have are the same as the specific examples of the substituent which $Ar_5$ to $Ar_7$ in the general formula [13] may each further have.

In the general formula [15], $Ar_{13}$ to $Ar_{15}$ each represent a substituted or unsubstituted, divalent arylene group. The divalent arylene group represented by any one of $Ar_{13}$ to $Ar_{15}$ is a substituent selected from a phenylene group, a biphenylene group, a terphenylene group, a naphthylene group, and a fluorenylene group. It should be noted that when k represents 2, two $Ar_{15}$'s may be identical to or different from each other.

In the general formula [15], $Ar_{16}$ and $Ar_{17}$ each represent a substituted or unsubstituted aryl group. Specific examples of the monovalent aryl group represented by any one of $Ar_{16}$ and $Ar_{17}$ are the same as the specific examples of the aryl group represented by any one of $Ar_5$ to $Ar_7$ in the general formula [13].

In addition, in the general formula [15], specific examples of a substituent which $Ar_{13}$ to $Ar_{17}$ may each further have are the same as the specific examples of the substituent which $Ar_5$ to $Ar_7$ in the general formula [13] may each further have.

In addition, an arylamine derivative has a feature that its hole transfer ability is higher than that of an aromatic hydrocarbon-based compound. Therefore, the silsesquioxane compound having the feature (2-4) has a feature that its hole transport ability is high by virtue of its structural feature (feature that the compound contains an arylamine structure).

Accordingly, the use of the silsesquioxane compound having the feature (2-4) as the hole injection layer or hole transport layer constituting the organic light emitting element increases its hole mobility and reduces its driving voltage.

The silsesquioxane compound of the present invention can be used as a constituent material for the organic light emitting element, i.e., a material for the organic light emitting element. Here, the material for the organic light emitting element is a material to be used in the formation of any one of the respective layers constituting the organic light emitting element such as a hole injection layer, a hole transport layer, an electron blocking layer, an emission layer, a hole blocking layer, an electron transport layer, and an electron injection layer.

The silsesquioxane compound of the present invention can be used as a constituent material for the emission layer. In this case, the compound is preferably used as a host. Here, the host is a compound having the largest weight ratio out of the compounds constituting the emission layer. In addition, the emission layer may contain not only the host but also a guest (dopant). Here, the guest is a compound that has a smaller weight ratio than that of the host out of the compounds constituting the emission layer and that is mainly responsible for light emission.

Of the silsesquioxane compounds of the present invention, the compound having the feature (2-4) is preferably used as a constituent material for the hole injection layer or hole transport layer constituting the organic light emitting element. This is because of the following reason: the compound having the feature (2-4) has a hole transport ability, and the compound itself does not absorb light emission from the emission layer and has a wide band gap. Therefore, the introduction of the compound having the feature (2-4) out of the silsesquioxane compounds of the present invention into the hole injection layer or the hole transport layer improves charge and exciton blocking abilities, thereby providing an organic light emitting element having additionally high light emitting efficiency.

In addition, out of the silsesquioxane compounds of the present invention, the compound having the feature (2-3) is preferably used, for example, as follows: the compound is mixed with any other organic compound and the mixture is used as the host for the emission layer. The same holds true for the case where the compound is used as a constituent material for any other layer (such as the hole injection layer or the hole transport layer). It can be said that the silsesquioxane compounds of the present invention including, but not limited to, the compound having the feature (2-3) are each preferred as the host for the emission layer that suitably has a wider band gap than the band gap of a light emitting dopant because the compounds each have a wide band gap. Here, it is because of the following reason that the band gap of the host is suitably wider than that of the light emitting dopant: satisfying the suitable condition suppresses the loss of an exciton due to the transfer of energy from the light emitting dopant to the silsesquioxane compound of the present invention. Accordingly, an exciton can be efficiently fed into the light emitting dopant and hence the light emitting dopant can efficiently emit light.

In addition, the silsesquioxane compound of the present invention can be used upon production of all organic light emitting elements that output light in the visible region because the compound has a wide band gap beyond an ultraviolet region. Here, examples of the organic light emitting elements that output light in the visible region include a blue light emitting element, a green light emitting element, a red light emitting element, and a white light emitting element.

(Specific Examples of Organic Compound of the Present Invention)

Specific examples of the silsesquioxane compound of the present invention are shown below, provided that the present invention is not limited to these specific examples. It should be noted that the term "POSS1" in the formulae refers to a substituent shown below and the term "POSS2" in the formulae refers to a substituent shown below.

POSS1
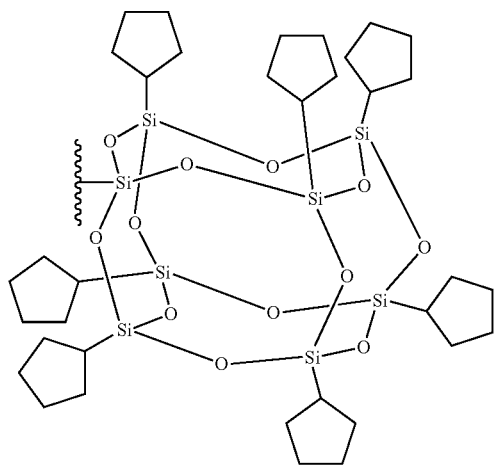
POSS2
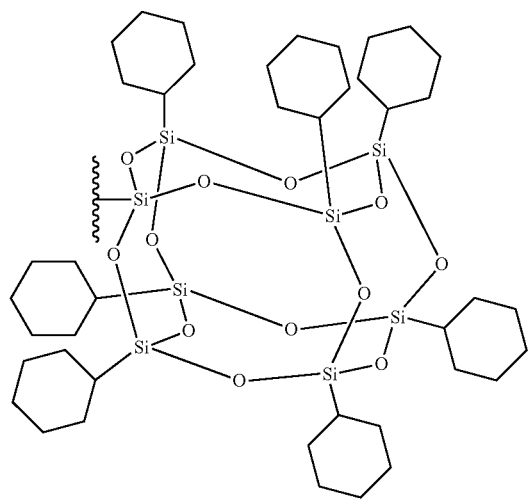
A1
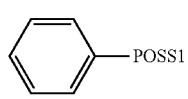—POSS1
A2
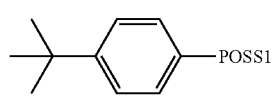—POSS1
A3
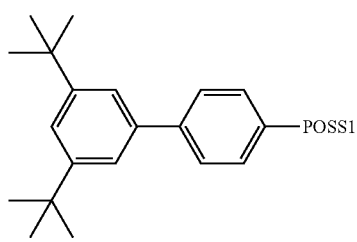—POSS1
A4
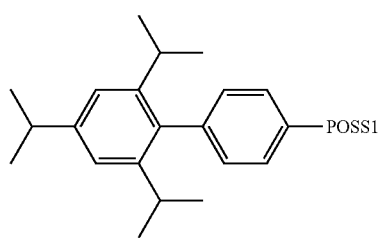—POSS1
A5
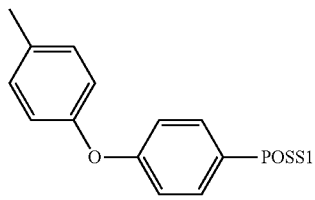—POSS1
A6
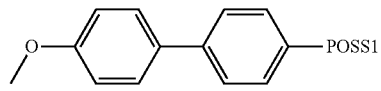—POSS1
A7
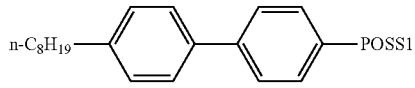—POSS1
A8
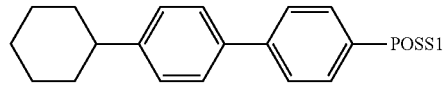—POSS1
A9
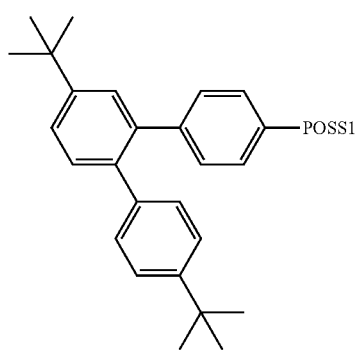—POSS1
A10
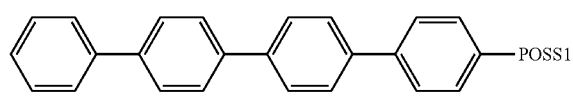—POSS1

-continued
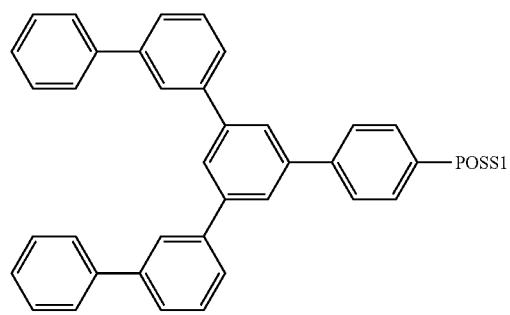 A11
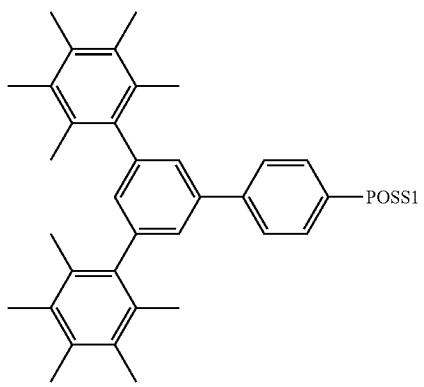 A12
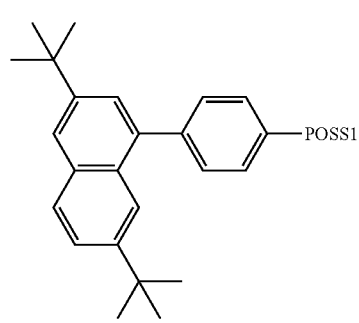 A13
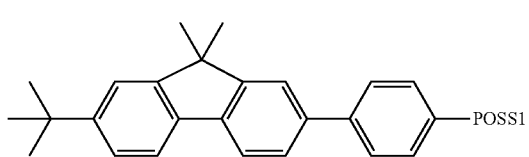 A14
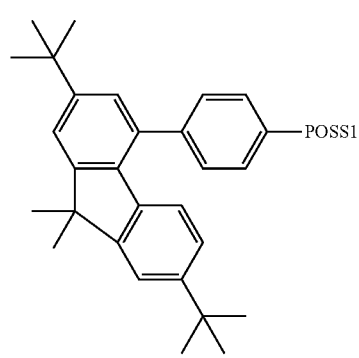 A15
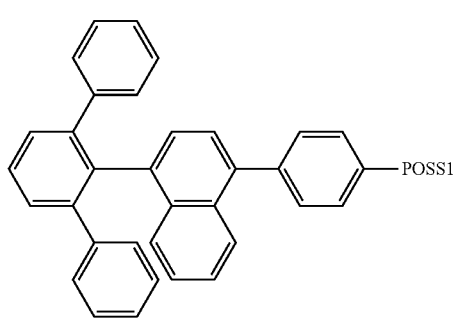 A16
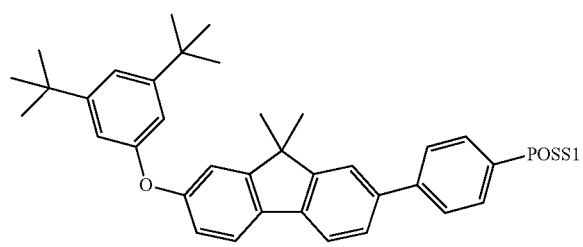 A17
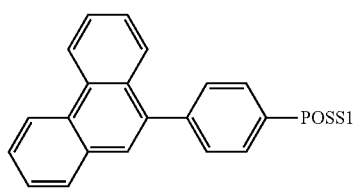 A18

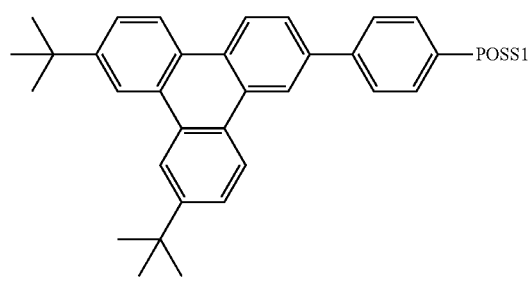
A19
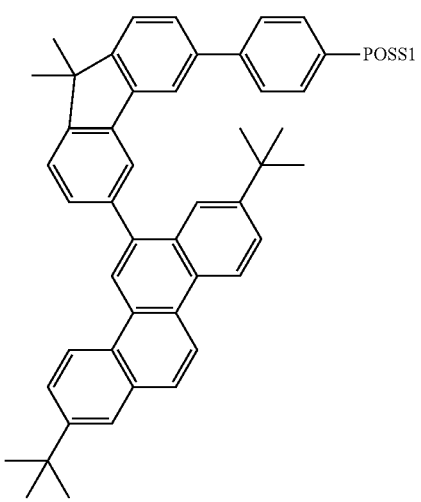
A20
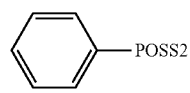
A21
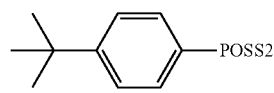
A22
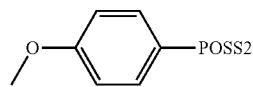
A23
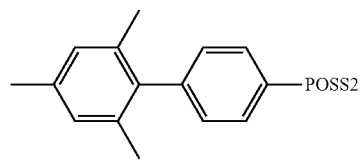
A24
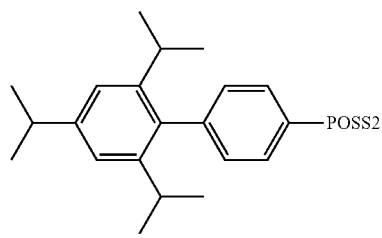
A25
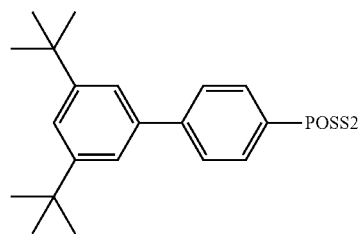
A26
A27
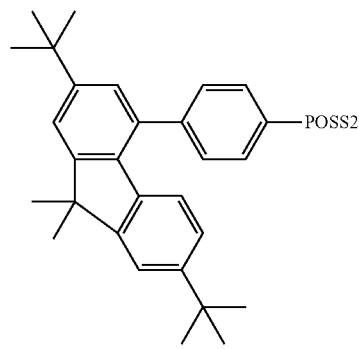
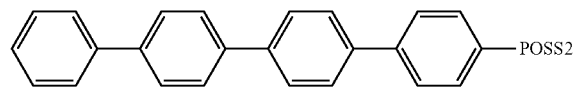
A28

-continued
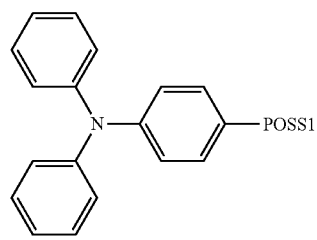
B1
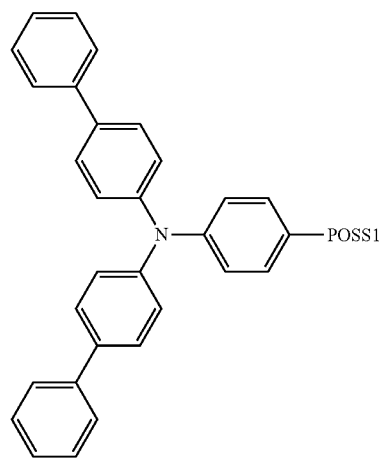
B2
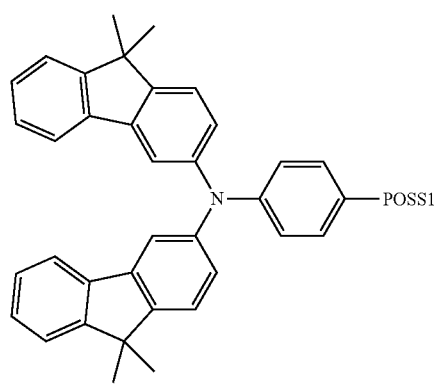
B3
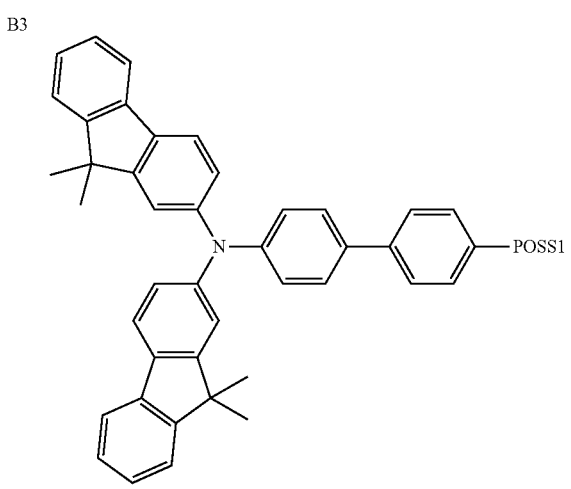
B4
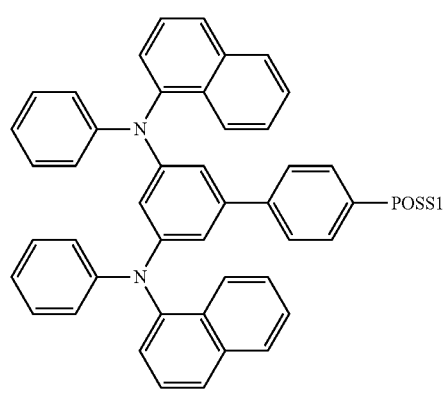
B5
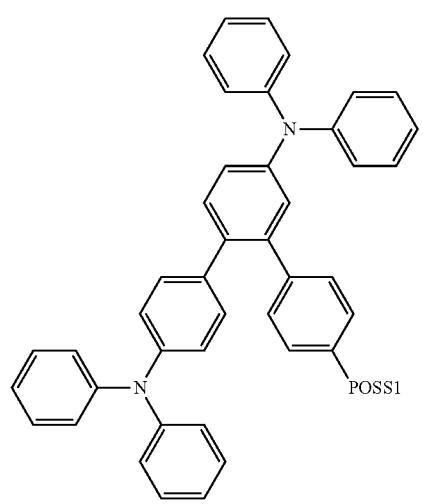
B6

-continued
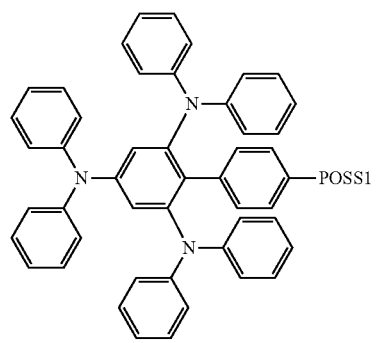
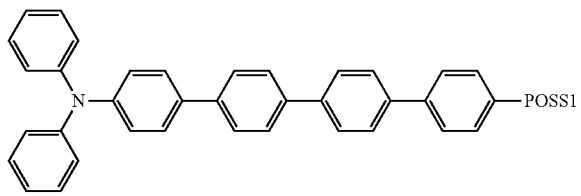
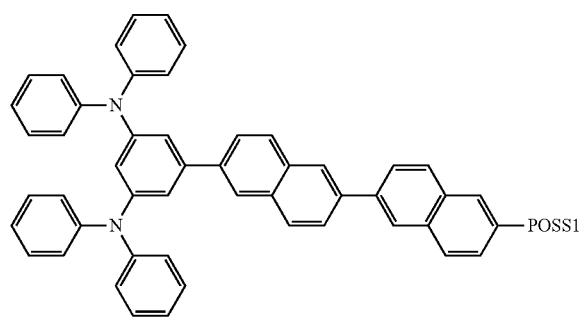
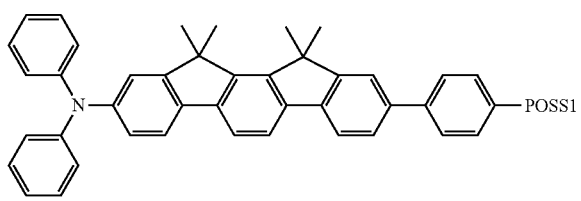
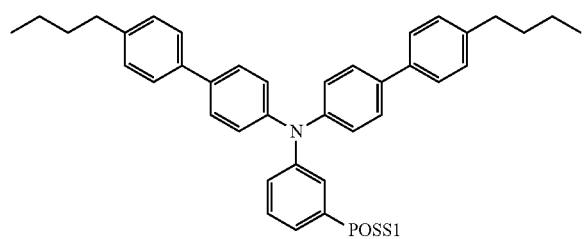
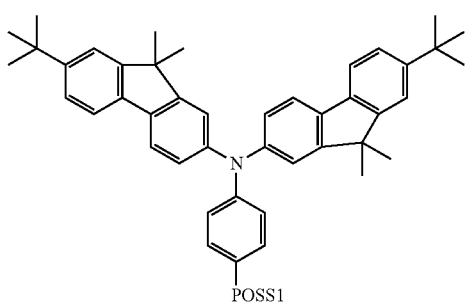

-continued
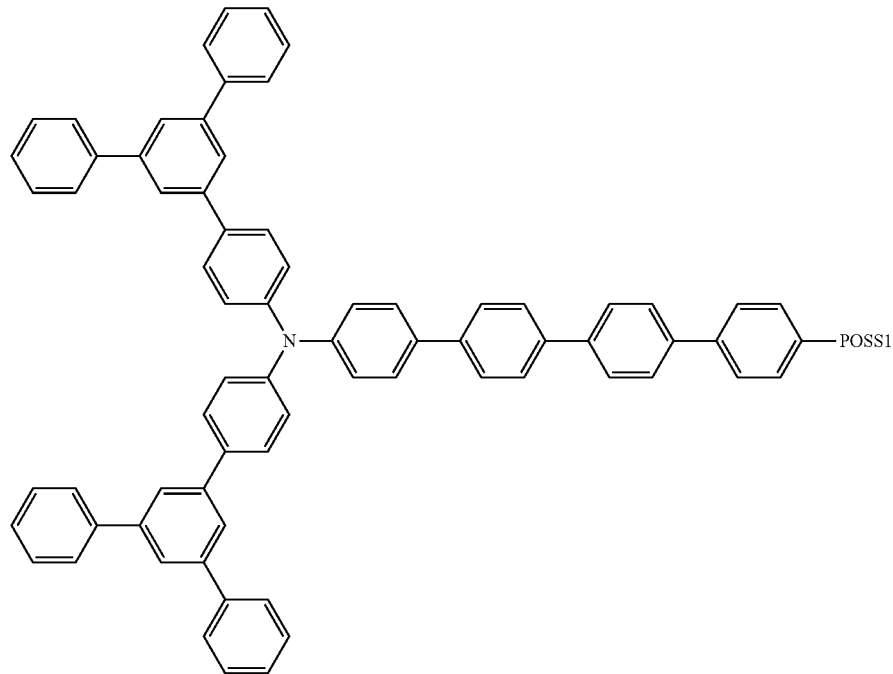
B12
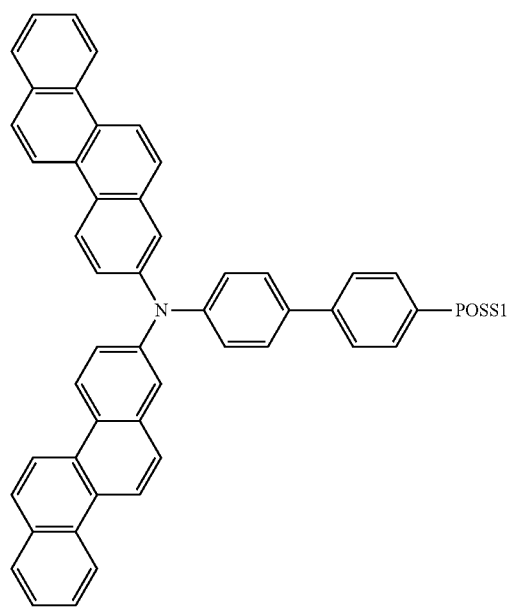
B13
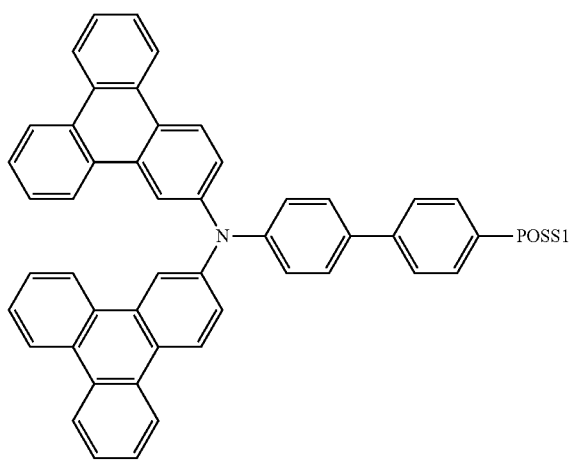
B14

-continued
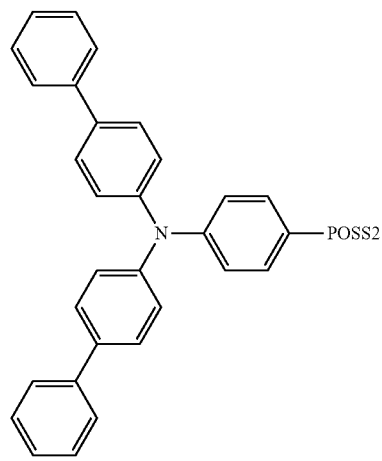
B15
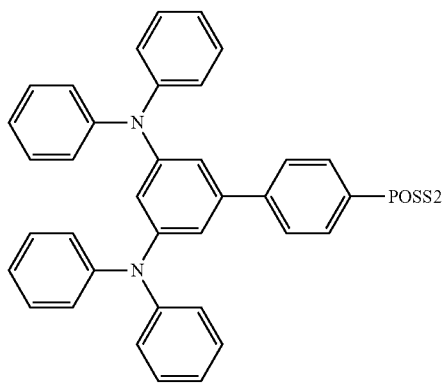
B16
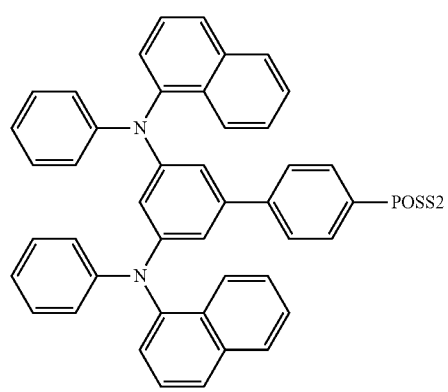
B17
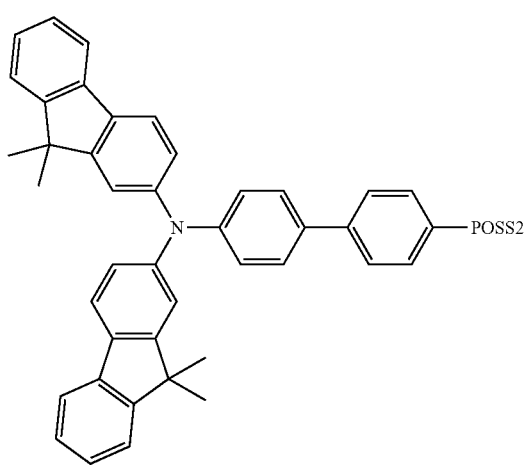
B18
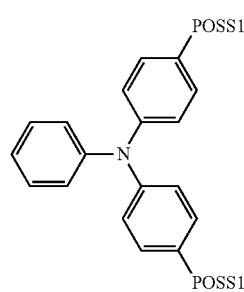
C1
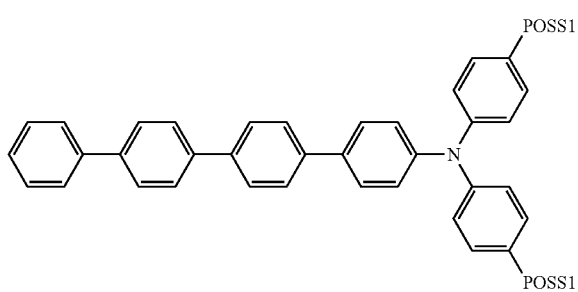
C2
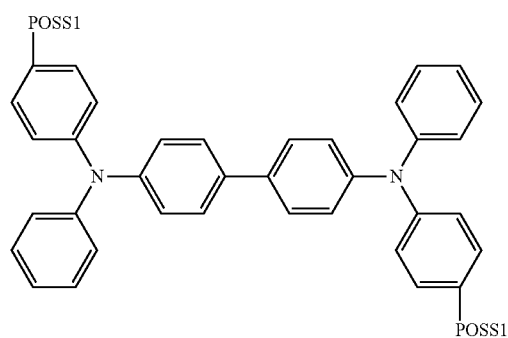
C3
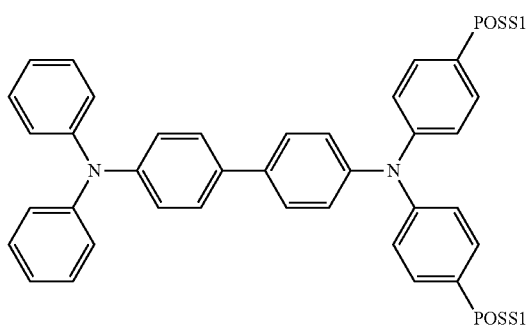
C4

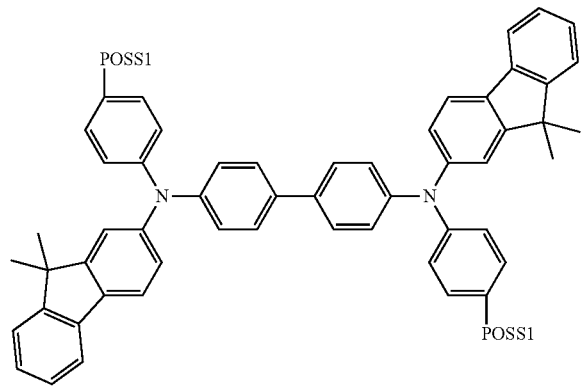
C5
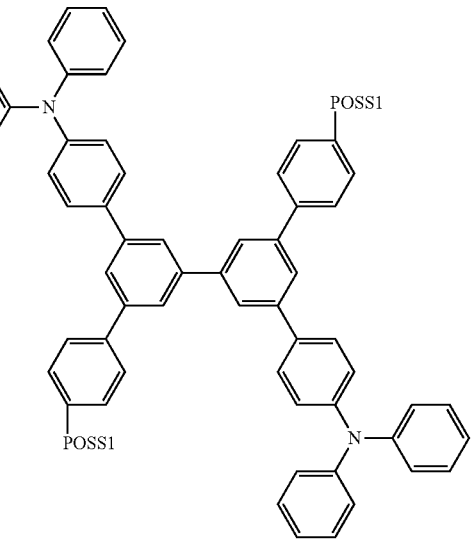
C6
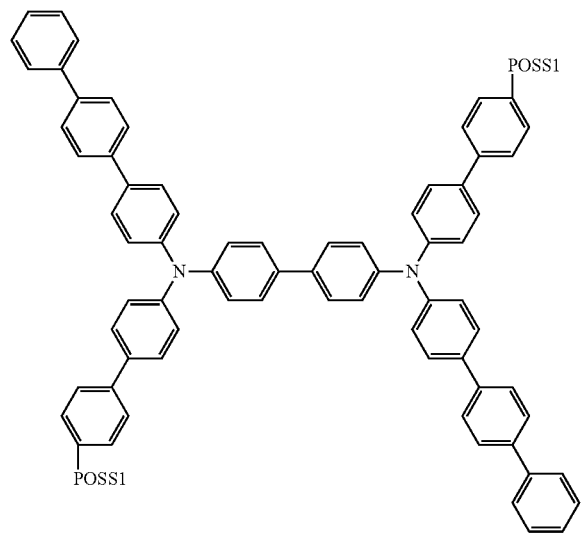
C7
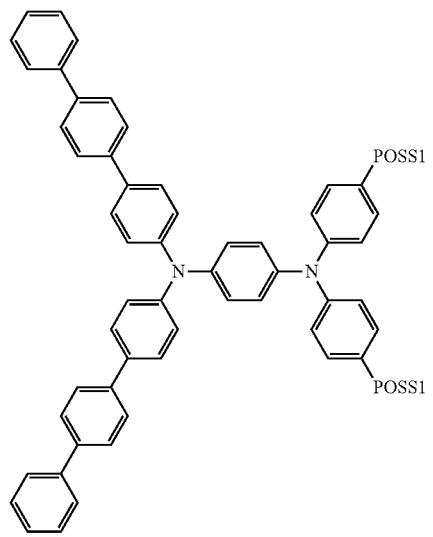
C8
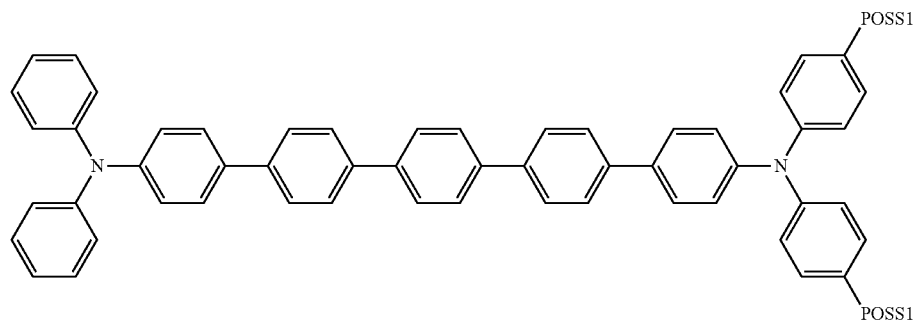
C9

-continued
C10
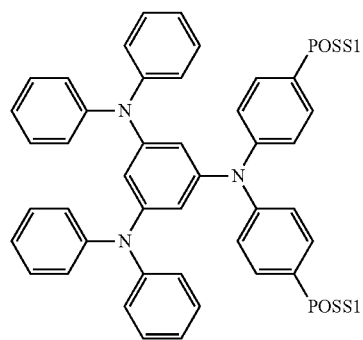
C11
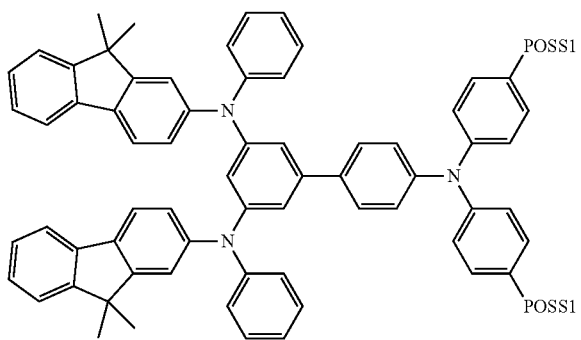
C12
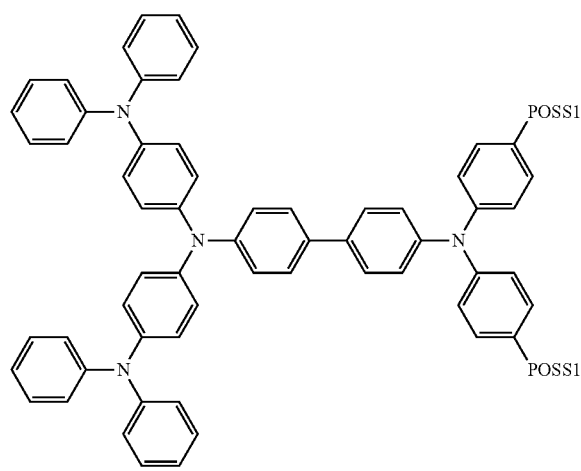
C13
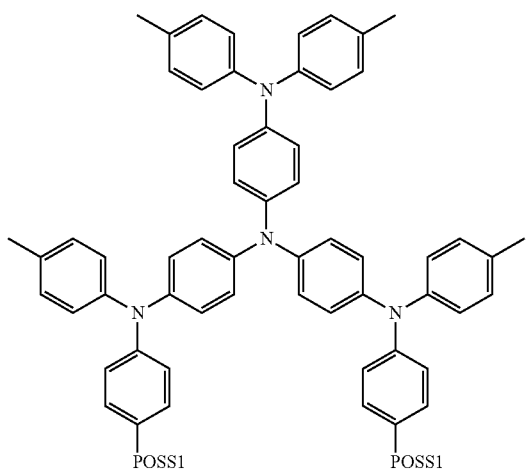
C14
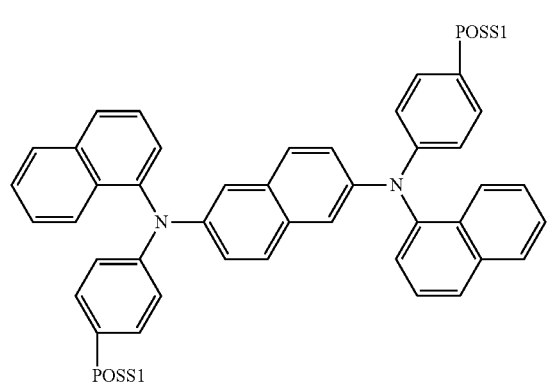
C15
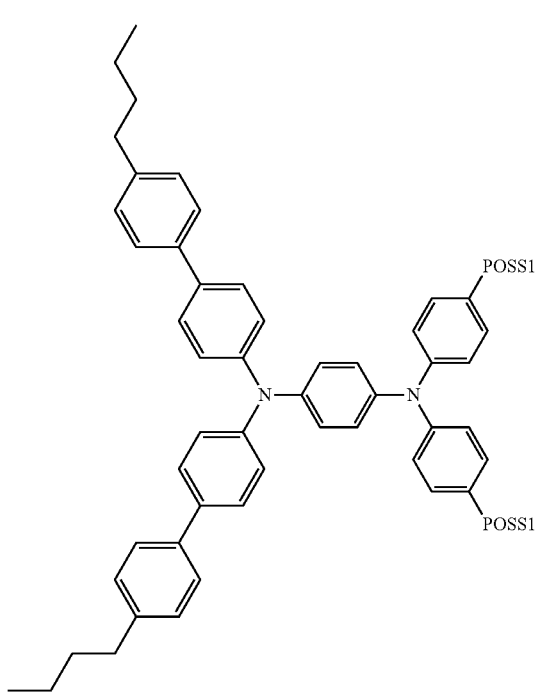

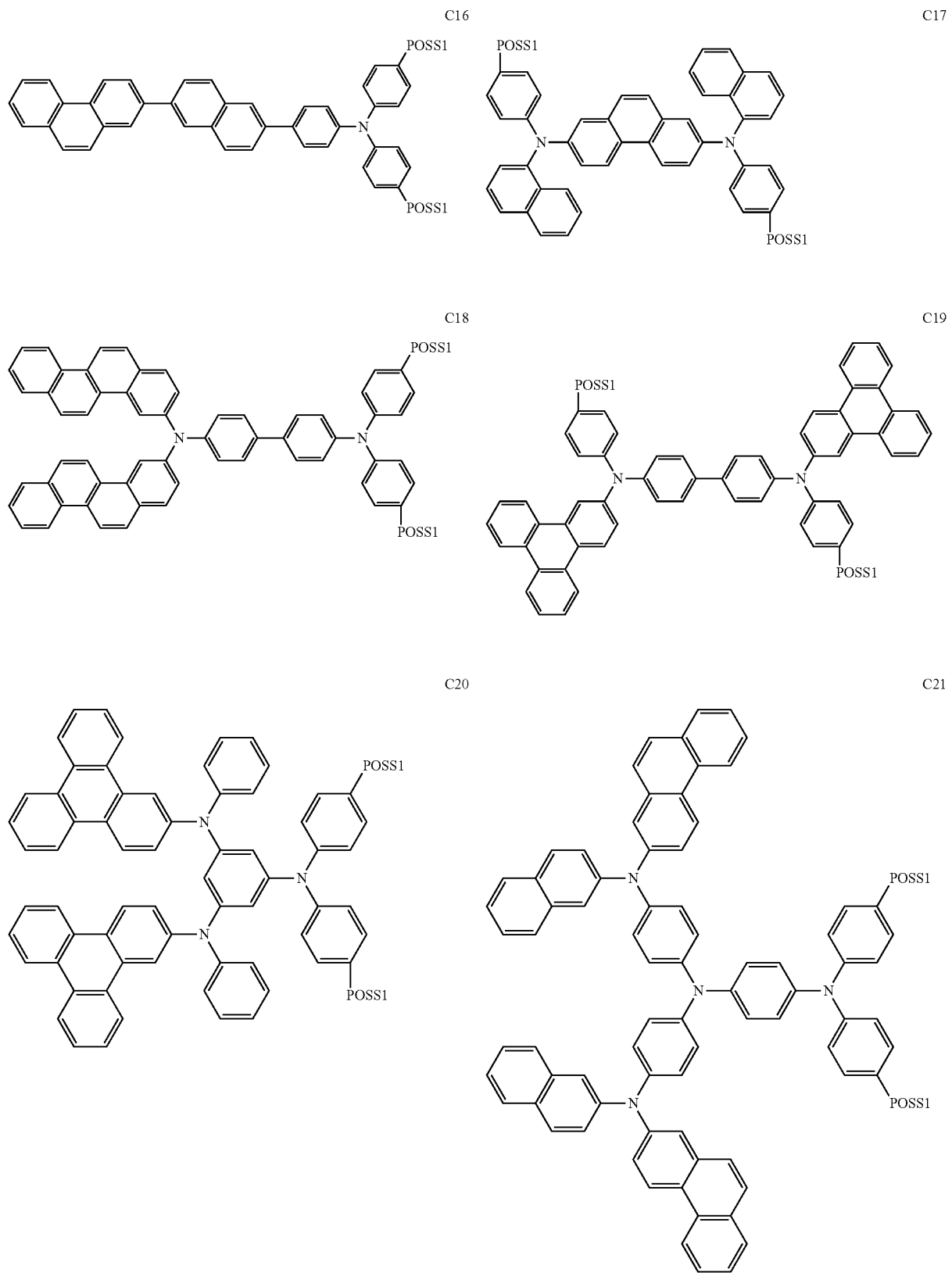

-continued
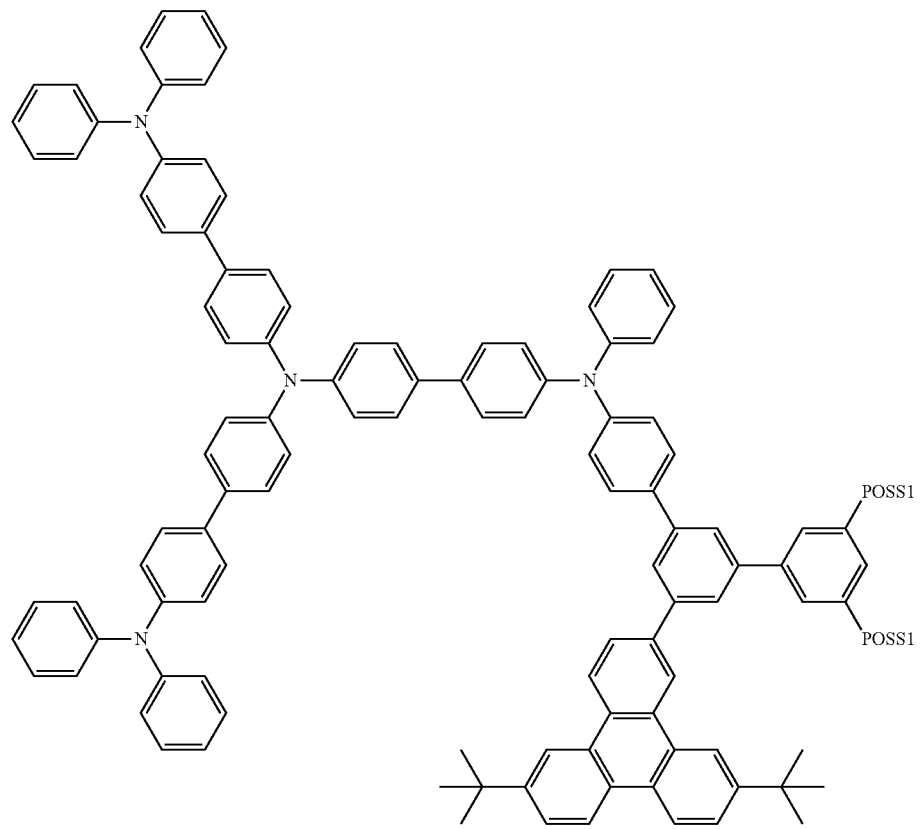
C22
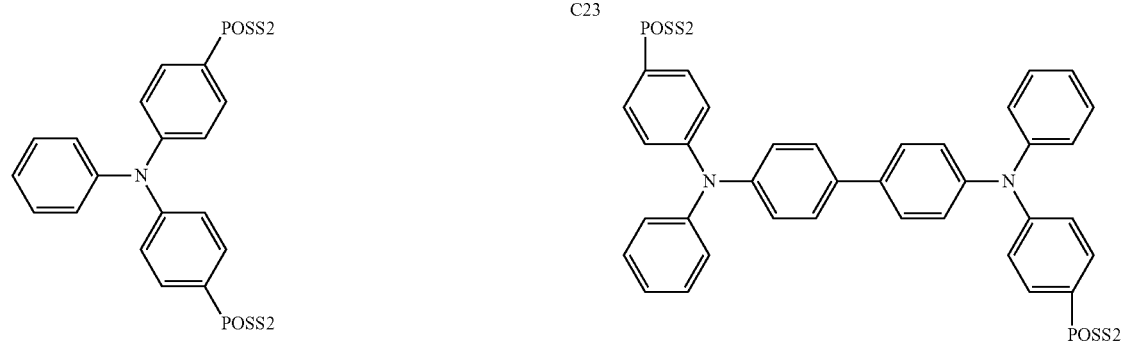
C23  C24
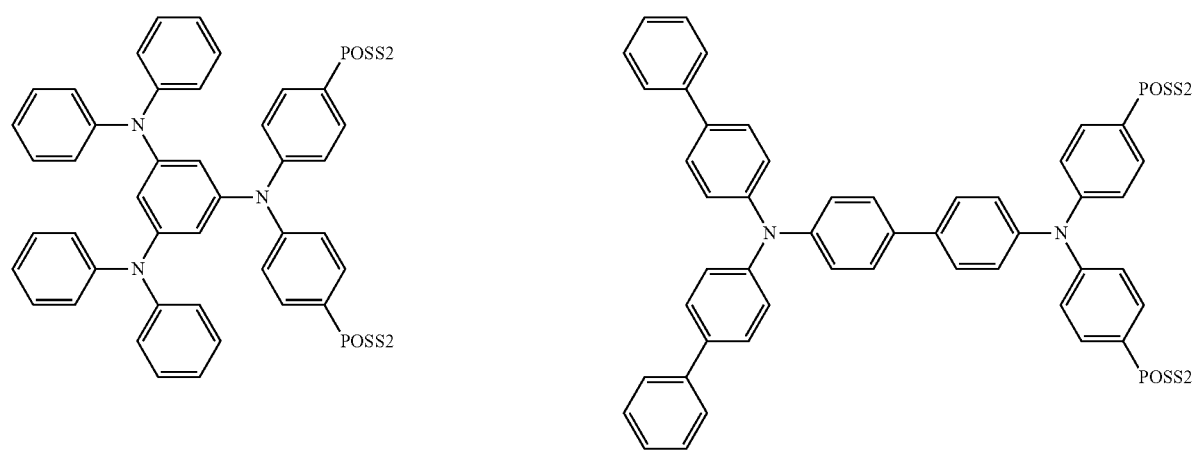
C25  C26

-continued
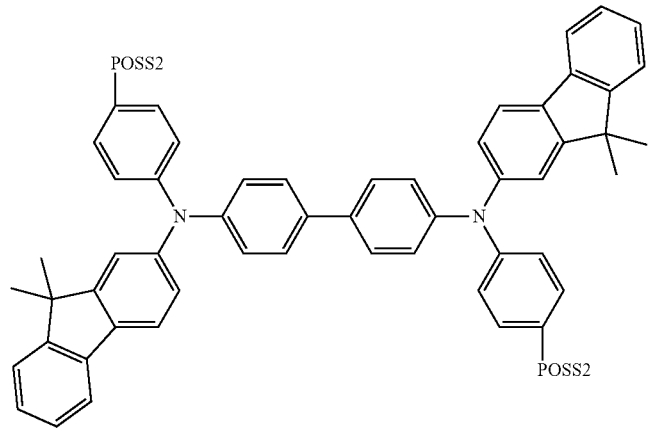
C27
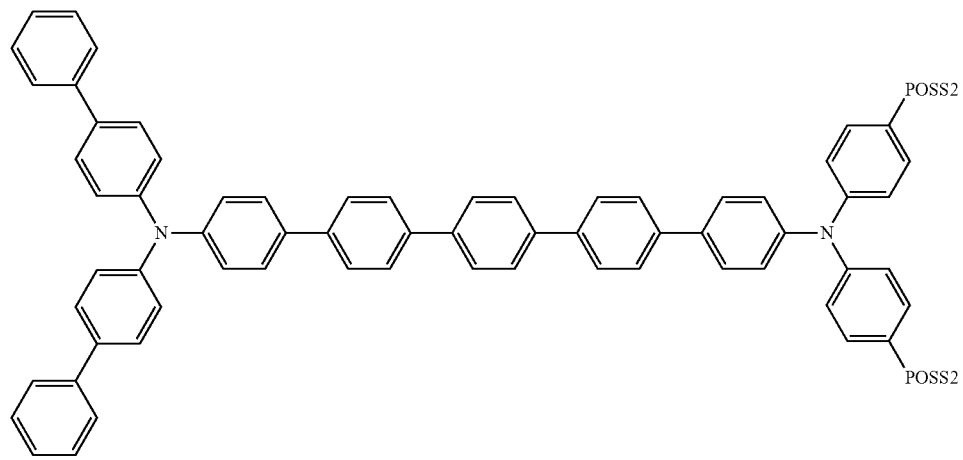
C28
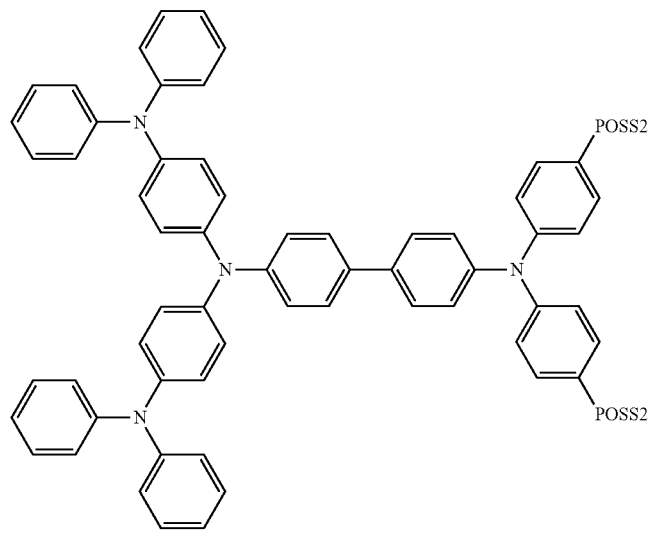
C29

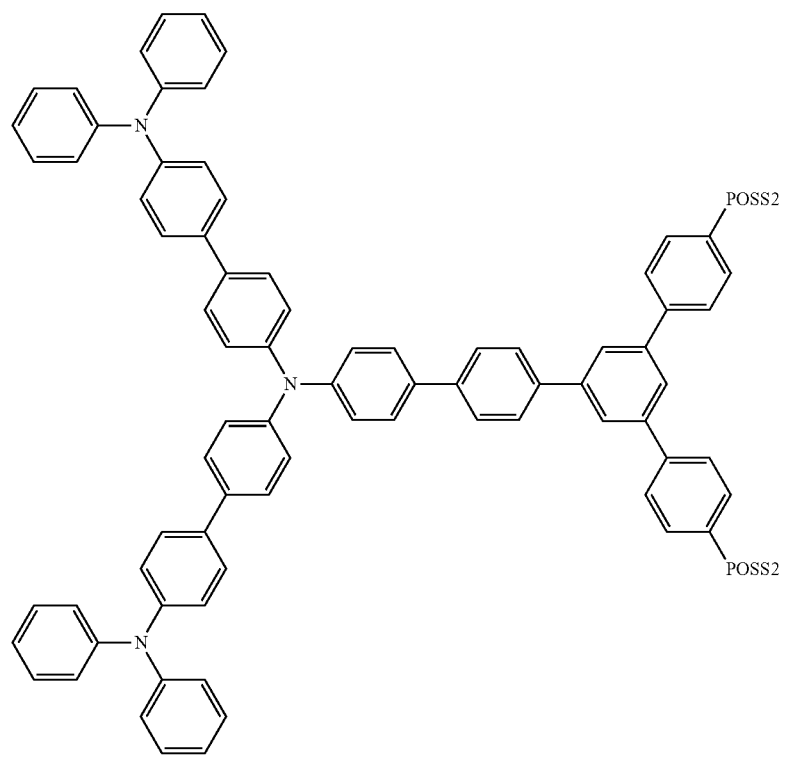
C30
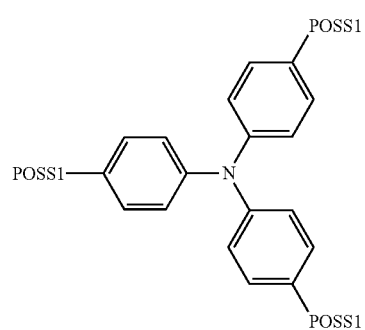
D1
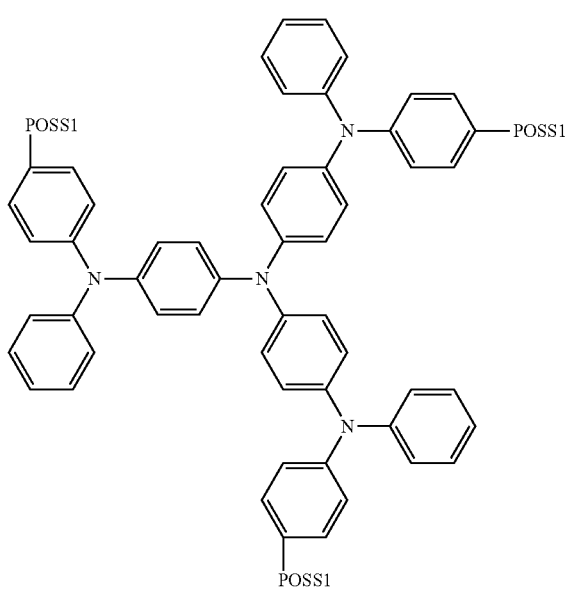
D2

-continued
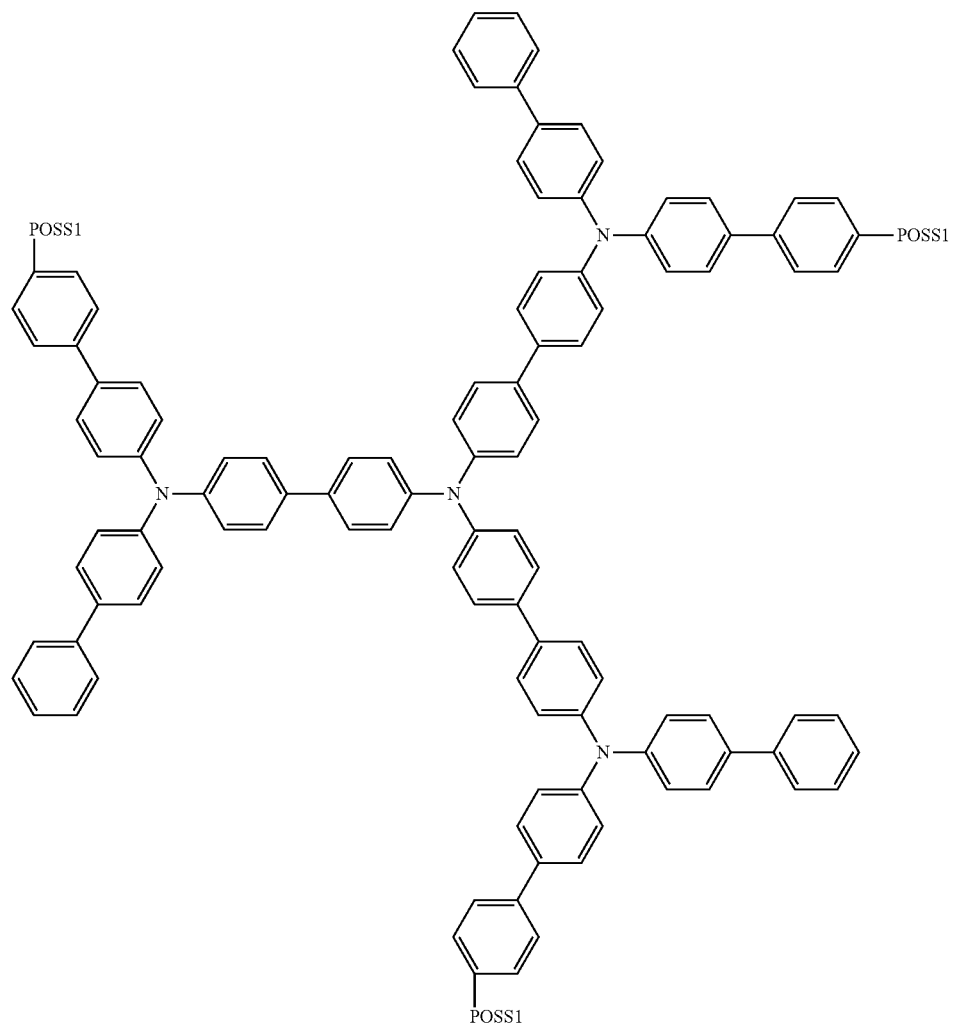
D3

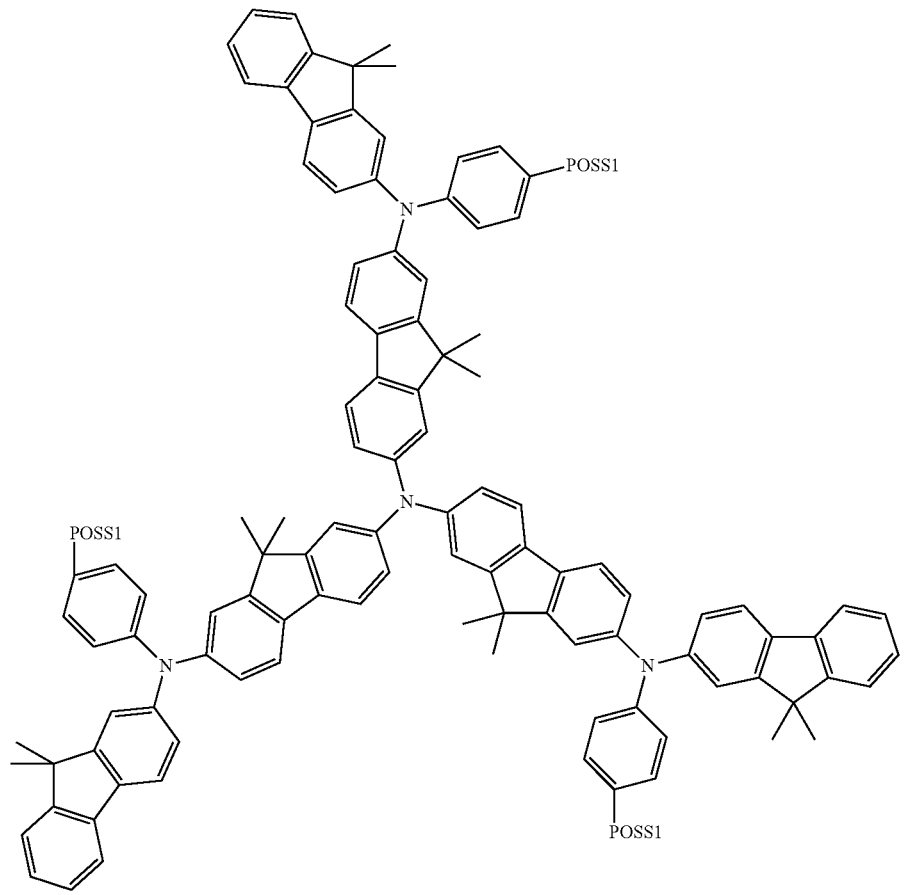
D4
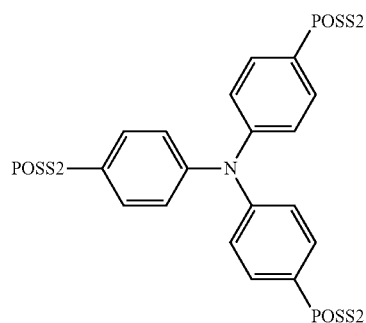
D5
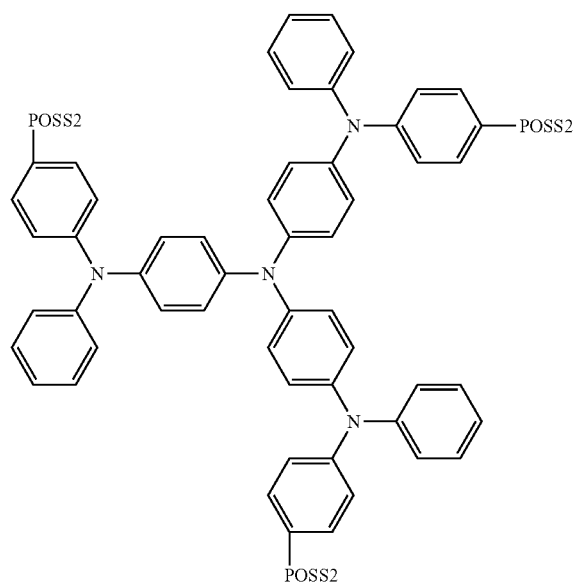
D6

-continued
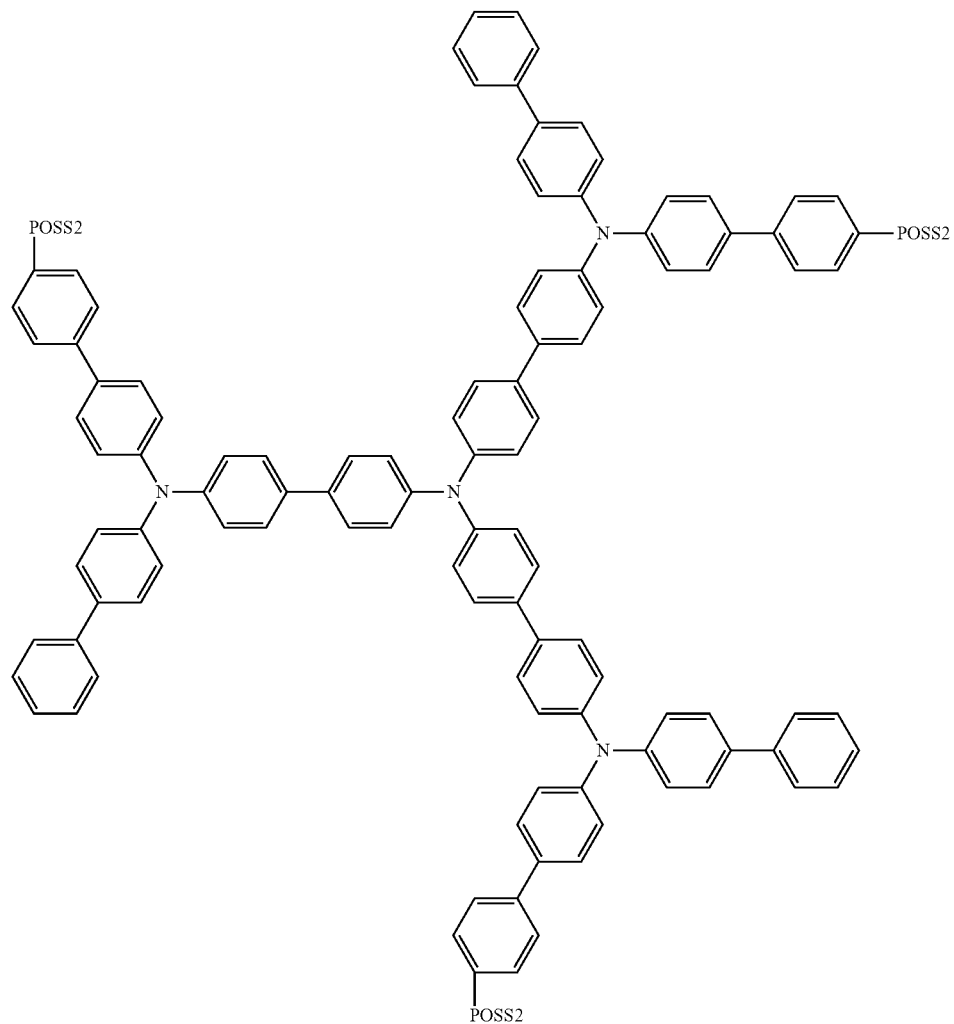
D7
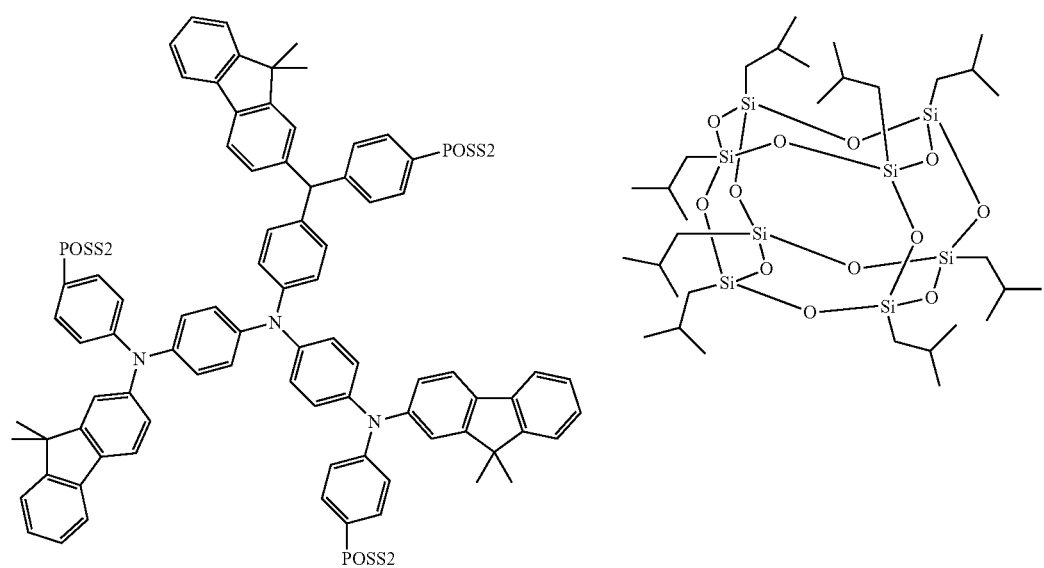
D8
E1

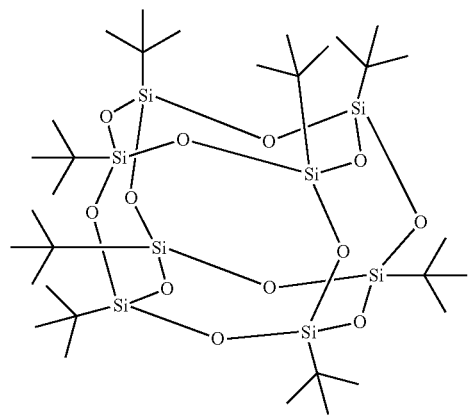
E2
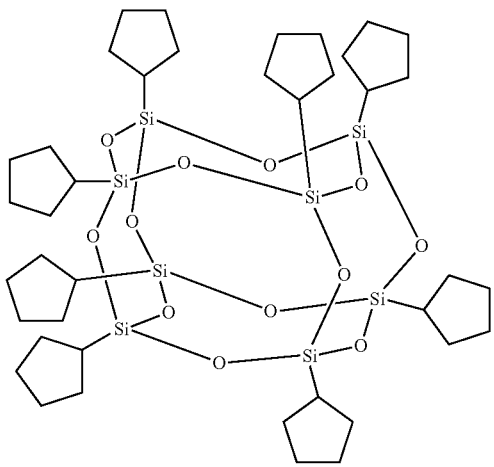
E3
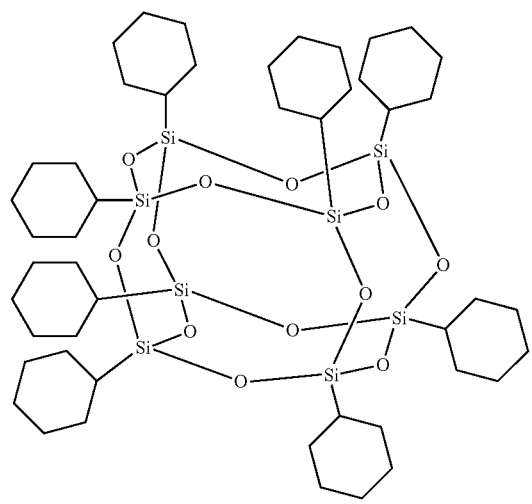
E4
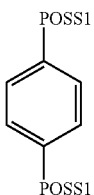
F1
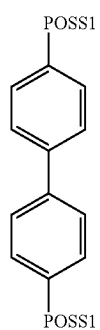
F2
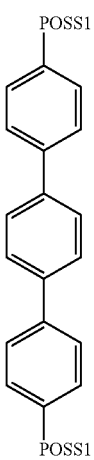
F3

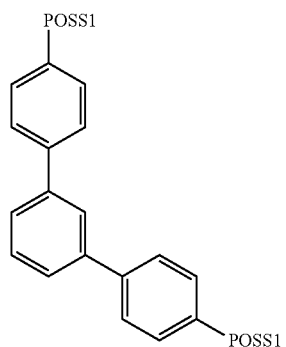 F4
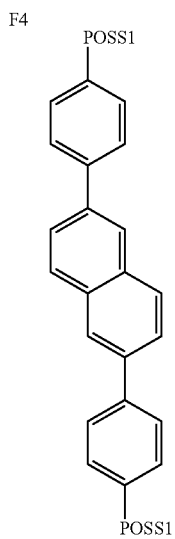 F5
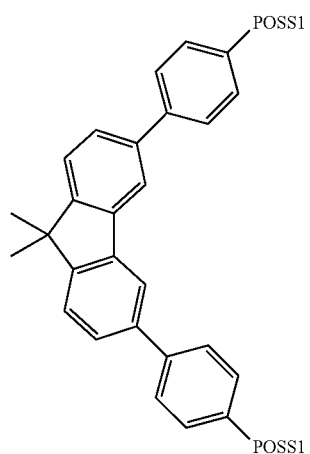 F6
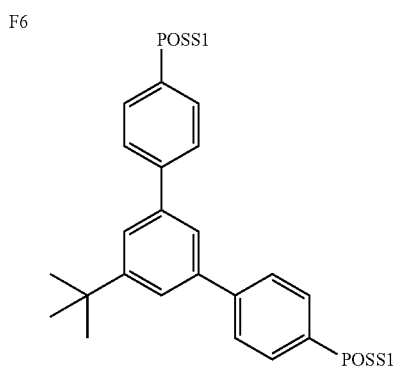 F7
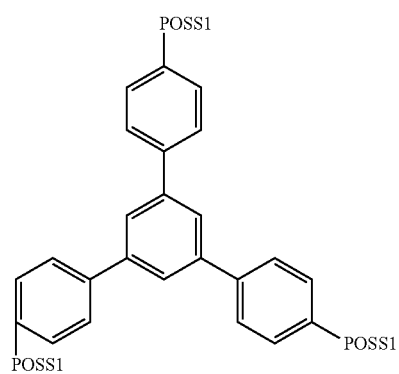 F8
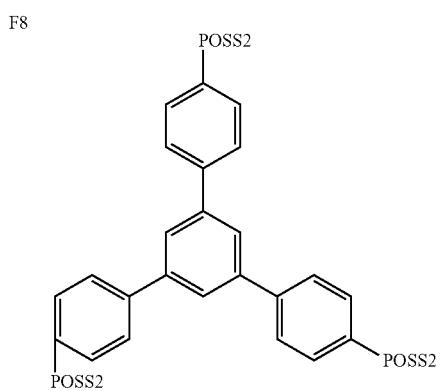 F9

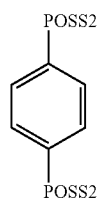

F10

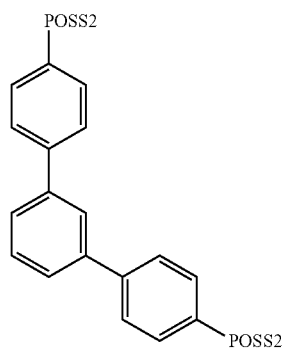

F11

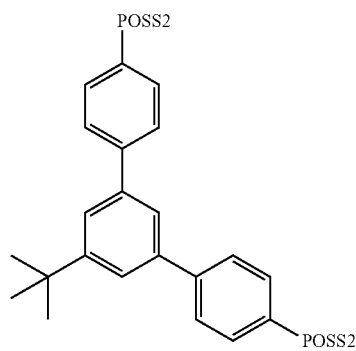

F12

Each of the silsesquioxane compounds listed above has a silsesquioxane skeleton. In addition, when the compound is brought into a thin-film state, the thin film has a low absorbance and a wide band gap because the number of the $SP^2$ carbon atoms of the compound is ten times or less the number of its silicon atoms.

In addition, the silsesquioxane compounds listed above can be classified into Group A to Group F described below depending on the number of silsesquioxane skeletons and the kinds of substituents. Effects specific to the respective groups are described below.

Compounds belonging to Group A are a group of compounds each having one silsesquioxane unit. Accordingly, the compound group has the following features: the compound group has a smaller molecular weight than that of any other compound group, can be subjected to sublimation purification, and can be easily synthesized. In addition, the compounds belonging to Group A each have a feature that the compound is stable to oxidation because the compound group is free of an arylamine structure.

Here, out of the compounds belonging to Group A, Exemplified Compounds A1 to A17 and A21 to A28 are a group of the following compounds: an aryl group in each of the compounds is an aryl group in which the number of condensed rings is two or less, specifically, a phenyl group, a terphenyl group, a naphthyl group, or a fluorenyl group. Here, a compound having an aryl group in which the number of condensed rings is two or less has a smaller number of π-electrons on $SP^2$ hybrid orbitals than that of a compound having an aryl group in which the number of condensed rings is three or more such as a phenanthrenyl group, a triphenylenyl group, a chrysenyl group, or a benzophenanthrenyl group. Accordingly, the compounds themselves have low absorbances and wide band gaps.

In particular, out of the compounds belonging to Group A, Exemplified Compounds A1 to A9, A13 to A15, and A21 to A27 are a group of compounds defined by the general formula [11] or the general formula [12], and are a group of the following compounds: the ratio of the number of silicon atoms to the number of $SP^2$ carbon atoms in a molecule of each of the compounds is 40% or more. Accordingly, the compounds each have a particularly high ratio of the number of silicon atoms in a molecule thereof. Accordingly, the absorbance of the entirety of each of the compounds additionally reduces and the band gap thereof additionally widens, and hence the compound is preferred. As a compound has a lower absorbance and a wider band gap, the extent to which the light emitting efficiency of the organic light emitting element is improved by using the compound as a constituent material for the element enlarges.

Compounds belonging to Group B are a group of compounds each having one silsesquioxane unit as in the compounds belonging to Group A. Accordingly, as in the compounds belonging to Group A, the compound group has the following features: the compound group has a small molecular weight, can be subjected to sublimation purification, and can be easily synthesized.

In addition, the compounds belonging to Group B each have a feature that its hole transport ability is high. That is, the compounds belonging to Group B each have a feature that the hole transport ability is additionally high because the ratio of the number of $SP^2$ carbon atoms in a molecule thereof is particularly high among the exemplified compounds of the silsesquioxane compound of the present invention.

Here, out of the compounds belonging to Group B, Exemplified Compounds B1 to B12 and B15 to B18 are each such that an aryl group in $Z_1$ is limited to an aryl group in which the number of condensed rings is two or less. Accordingly, a low absorbance and a wide band gap can be realized.

In particular, Exemplified Compounds B1 to B8, B10 to B12, and B15 to B18 are a group of compounds defined by the general formula [13]. Accordingly, the number of aryl groups constituting a partial structure bonded to the silsesquioxane unit is small and at least one of the aryl groups is a phenyl group. Accordingly, the absorbance additionally reduces and the wide band gap can be maintained.

Compounds belonging to Group C are a group of the following compounds: the compounds each have two silsesquioxane units in a molecule thereof and a partial structure ($Z_2$) linking the two silsesquioxane units contains an arylamine structure. The compounds belonging to Group C are each a compound having the following features: the compound has a high ratio of the number of silicon atoms to the number of $SP^2$ carbon atoms in a molecule thereof and has a high ability to finely adjust physical properties. Here, it is because the molecule contains two silsesquioxane skeletons that the ratio of the number of the silicon atoms to the number of the $SP^2$ carbon atoms in the molecule is high. Accordingly, even when the number of the $SP^2$ carbon atoms increases, the ratio of the number of the silicon atoms to the number of the $SP^2$ carbon atoms in the molecule can be kept at 10% or more, and hence combinations of the kinds and number of aryl groups that can be incorporated into $Z_2$ can be diversified. Therefore, the compounds belonging to Group C each have the following feature: physical properties required as a constituent material for the organic light emitting element such as a hole injection ability, a hole transport ability, an HOMO level, and a glass transition temperature can be finely adjusted. Accordingly, when any one of the compounds belonging to Group C is used as a constituent material for the organic light emitting element, the compound can adapt to various element constructions.

Here, out of the compounds belonging to Group C, Exemplified Compounds C1 to C15 and C23 to C30 are each such that an aryl group in $Z_2$ is limited to an aryl group in which the number of condensed rings is two or less. Accordingly, a low absorbance and a wide band gap can be realized, and hence any such compound is preferred.

In particular, Exemplified Compounds C3 to C5, C7 to C9, C14, C15, C24, and C26 to C28 are a group of compounds defined by the general formula [14] or [15]. Those compounds are a group of the following compounds: the number of aryl groups constituting a partial structure bonded to a silsesquioxane unit is small and the compounds each contain two arylamine structures. In addition, those compounds are preferred because each of the compounds has a low absorbance and a wide band gap, and has a good balance with the physical properties such as the hole injection ability, the hole transport ability, the HOMO level, and the glass transition temperature.

Compounds belonging to Group D are a group of the following compounds: the compounds each have three silsesquioxane units in a molecule thereof and a partial structure ($Z_3$) linking the three silsesquioxane units contains an arylamine structure. The compounds belonging to Group D are each a compound having a high ratio of the number of silicon atoms to the number of $SP^2$ carbon atoms in a molecule thereof, specifically, 20% or more. Accordingly, an additionally low absorbance and an additionally wide band gap can be realized.

Compounds belonging to Group E are a group of compounds each having no aryl group. Accordingly, the ratio of Si atoms in a layer containing any such silsesquioxane compound can be easily increased. In addition, none of the compounds belonging to Group E has absorption in the visible region because none of the compounds has an aromatic ring in a molecule thereof. Further, none of the compounds belonging to Group E has an arylamine structure, to say nothing of an aryl group. Therefore, when any one of the compounds belonging to Group E is used as a constituent material for the organic light emitting element, the compound is preferably mixed with, for example, a hole injection material or a hole transport material.

Compounds belonging to Group F are a group of compounds each containing no arylamine structure and are a group of compounds each having two or three silsesquioxane units in a molecule thereof. The compounds belonging to Group F each have a feature that the compound is stable to oxidation because the compounds are a group of compounds each containing no arylamine structure. In addition, each of the compounds belonging to Group F has a high ratio of the number of silicon atoms to the number of $SP^2$ carbon atoms in a molecule thereof, specifically, 40% or more because the compound has two or three silsesquioxane units. Accordingly, the compounds each also have a feature that an additionally low absorbance and an additionally wide band gap can be realized.

The silsesquioxane compound of the present invention is mainly used as a constituent material for the organic light emitting element.

When the silsesquioxane compound of the present invention is used as a constituent material for the organic light emitting element, embodiments of the organic light emitting element having the silsesquioxane compound of the present invention are roughly classified into two embodiments, specifically, the following embodiments (2A) and (2B): (2A) an organic light emitting element having at least an anode, a cathode, an emission layer formed between the anode and the cathode, and an organic compound layer formed between the anode and the emission layer, the organic compound layer containing a compound having a tertiary arylamine structure; and (2B) an organic light emitting element having an anode, a cathode, and an organic compound layer formed between the anode and the cathode.

When the silsesquioxane compound of the present invention is used as a constituent material for the organic light emitting element according to the aspect (2A), the organic compound of the present invention is incorporated into the organic compound layer together with the compound having a tertiary arylamine structure. Here, the organic compound layer constituting the organic light emitting element according to the aspect (2A) is a layer formed between the anode and the emission layer. Accordingly, the organic compound of the present invention is incorporated into a layer formed between the anode and the emission layer such as a hole transport layer, a hole injection layer, or an electron blocking layer. In addition, the silsesquioxane compound of the present invention is a compound having a wider band gap among the siloxane compounds. Accordingly, the compound is a suitable material as compared with any other siloxane compound.

By the way, the aspect (2B) can be subdivided into the following (2B-1) to (2B-3): (2B-1) an organic light emitting element having an anode, a cathode, an emission layer formed between the anode and the cathode, and an organic compound layer (hole injection/transport layer) formed between the anode and the emission layer; (2B-2) an organic light emitting element having an anode, a cathode, an emission layer formed between the anode and the cathode, and an organic compound layer (electron injection/transport layer) formed between the cathode and the emission layer; and (2B-3) an organic light emitting element having an anode, a cathode, and an emission layer formed between the anode and the cathode (an organic light emitting element having an emission layer as the "organic compound layer" in the aspect (2B)).

When the silsesquioxane compound of the present invention is used as a constituent material for the organic light emitting element according to the aspect (2B), examples of the organic compound layer containing the organic compound of the present invention include an emission layer, a hole injection/transport layer (a hole injection layer, a hole transport layer, or an electron blocking layer), and an electron injection/transport layer (an electron injection layer, an electron transport layer, or a hole/exciton blocking layer). In addition, when the organic compound of the present invention is used as a constituent material for the organic light emitting element according to the aspect (2B), the layer containing the organic compound of the present invention may be a single layer or may be multiple layers. Further, when the organic compound of the present invention is used as a constituent material for the organic light emitting element according to the aspect (2B), the layer containing the organic compound of the present invention may be a layer formed only of the organic compound of the present invention, or may be a layer obtained by mixing the organic compound of the present invention and any other compound.

When the silsesquioxane compound of the present invention and any other compound are mixed to form a layer, their mixing ratio is appropriately adjusted. Here, in the case of film formation involving the sublimation of the compounds such as a vacuum deposition method, the mixing ratio is determined in consideration of a ratio between their sublimation rates at the time of vapor deposition. In addition, in the case of an application method, a weight ratio between the compounds at the time of the preparation of an application solution is taken into consideration.

The basic construction of the organic light emitting element of the present invention having an organic compound is, for example, described in each of the following constructions (a) to (e), provided that the present invention is not limited thereto.

(a) (Substrate/)anode/emission layer/cathode
(b) (Substrate/)anode/hole transport layer/electron transport layer/cathode
(c) (Substrate/)anode/hole transport layer/emission layer/electron transport layer/cathode
(d) (Substrate/)anode/hole injection layer/hole transport layer/emission layer/electron transport layer/cathode
(e) (Substrate/)anode/hole transport layer/emission layer/hole/exciton blocking layer/electron transport layer/cathode Although each of the constructions (a) to (e) is a construction in the case where an electrode close to the substrate is the anode, the present invention is not limited thereto and a construction in the case where the electrode close to the substrate is the cathode is of course included in the present invention.

(3) Other Constituent Materials for Organic Light Emitting Element

Next, other constituent materials for the organic light emitting element of the present invention (materials except siloxane compounds (including a compound corresponding to the silsesquioxane compound of the present invention) and the compound having a tertiary arylamine structure) are described. In the organic light emitting element of the present invention, conventionally known low-molecular weight and high-molecular weight materials can be used as required. More specifically, a hole injectable/transportable material, an emission assisting material, an electron injectable/transportable material, or the like can be used.

Hereinafter, examples of these materials are described.

Examples of the hole injectable/transportable material include the organic compounds represented by any one of the general formulae [1] to [6] as well as a triarylamine derivative, a phenylenediamine derivative, a stilbene derivative, a phthalocyanine derivative, a porphyrin derivative, poly(vinyl carbazole), poly(thiophene), and any other conductive polymer. It should be noted that the present invention is not limited to these materials.

As a light emitting material (guest) mainly involved in light emitting function, there are given, for example: a fluorescent light emitting material that emits blue, green, or red light such as a triarylamine derivative, a phenylene derivative, a condensed ring aromatic compound (e.g., a fluoranthene derivative, a benzofluoranthene derivative, a pyrene derivative, a chrysene derivative, or a derivative obtained by substitution thereof with a diarylamine), or a stilbene derivative; and a phosphorescent light emitting material that emits blue, green, or red light such as an organic metal complex (e.g., an organic iridium complex, an organic platinum complex, or a rare earth metal complex).

In the present invention, the content of the guest is preferably from 0.1 mass % or more and 30 mass % or less, more preferably from 0.5 mass % or more and 10 mass % or less with reference to the total amount of the emission layer.

The host in the emission layer is a material having the highest weight ratio in the emission layer. Examples of the host include, but of course not limited to, a triarylamine derivative, a phenylene derivative, a condensed ring aromatic compound (e.g., a naphthalene derivative, a phenanthrene derivative, a fluorene derivative, or a chrysene derivative), an organic metal complex (e.g., an organic aluminum complex such as tris(8-quinolinolato)aluminum, an organic beryllium complex, an organic iridium complex, or an organic platinum complex), and a polymer derivative such as a poly(phenylene vinylene) derivative, a poly(fluorene) derivative, a poly(phenylene) derivative, a poly(thienylene vinylene) derivative, or a poly(acetylene) derivative.

More specific examples of the host include the group of compounds represented in Table 2.

TABLE 2

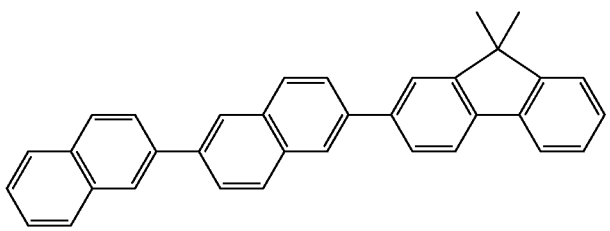 [SMILES: CC1(C)c2ccccc2-c2ccc(-c3ccc4cc(-c5ccc6ccccc6c5)ccc4c3)cc21]

H1

TABLE 2-continued
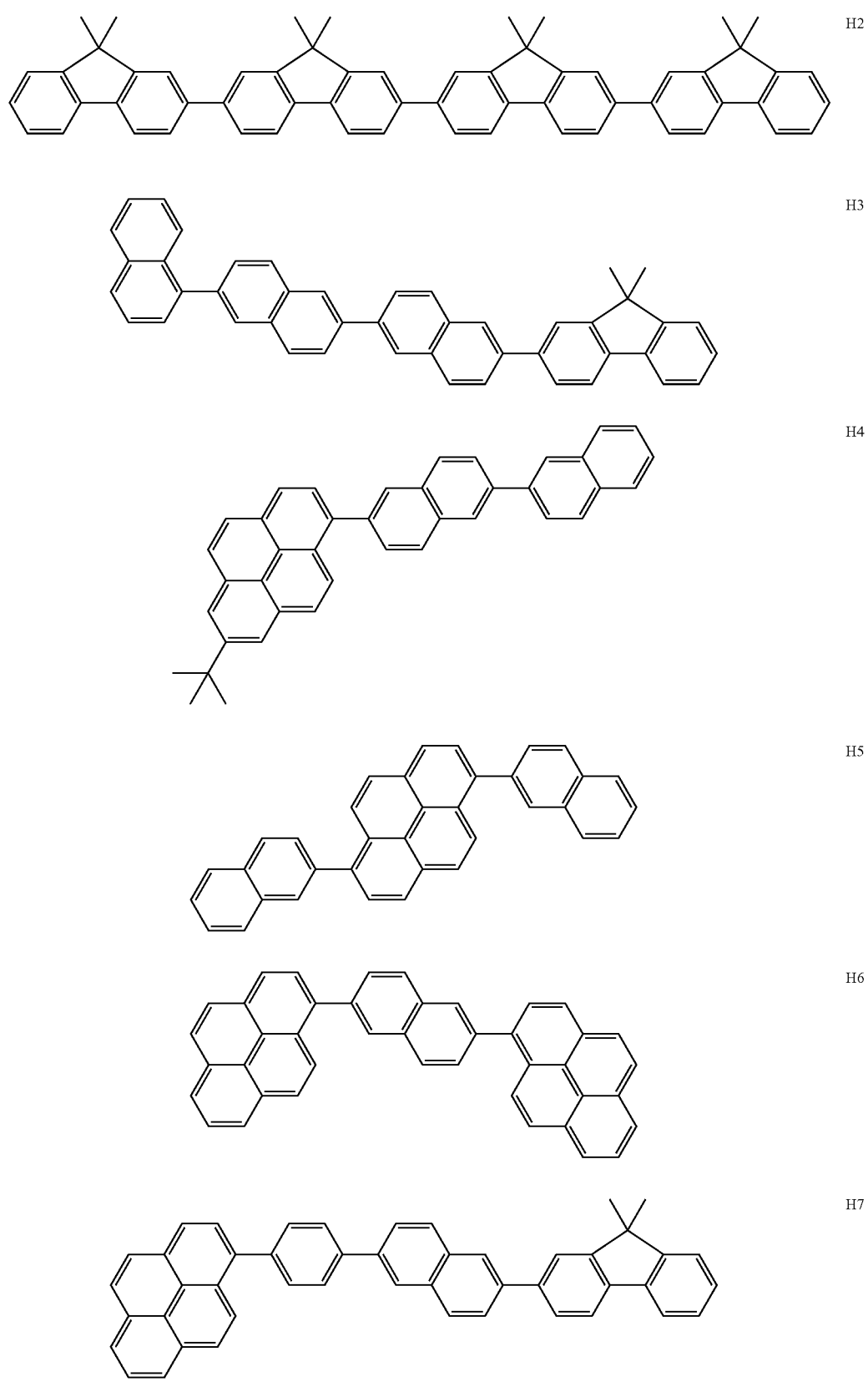
H2
H3
H4
H5
H6
H7

TABLE 2-continued
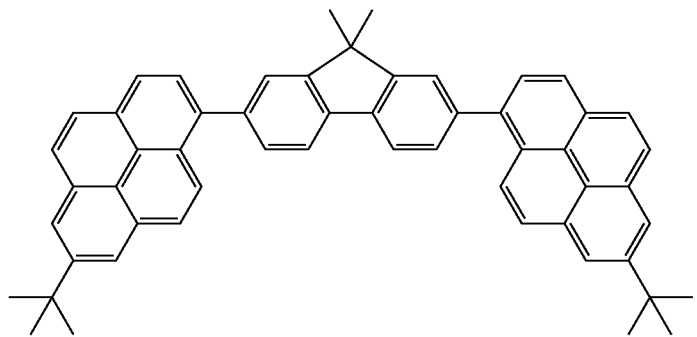 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] H8
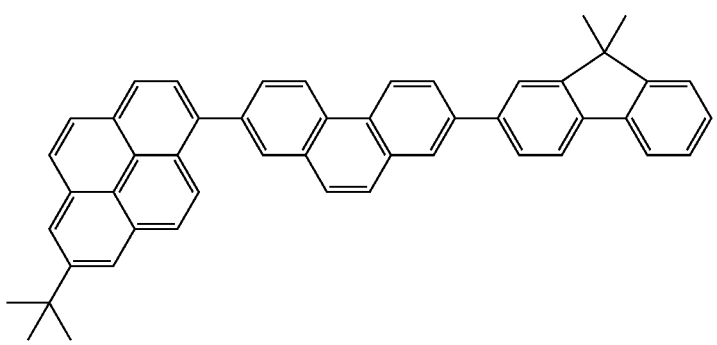 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] H9
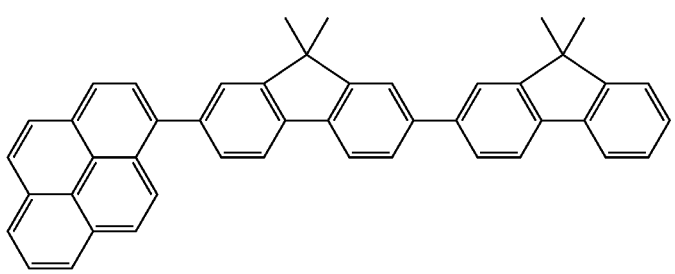 [SMILES: CC1(C)c2ccccc2-c2ccc(-c3ccc4c(c3)C(C)(C)c3cc(-c5ccc6ccc7cccc8ccc5c6c78)ccc3-4)cc21] H10
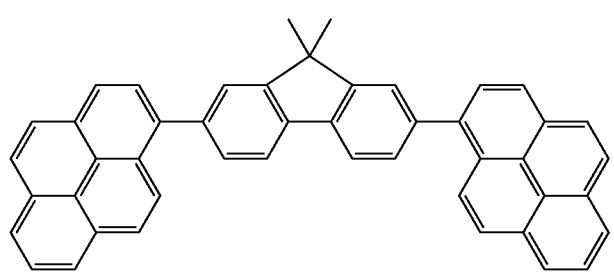 [SMILES: CC1(C)c2cc(-c3ccc4ccc5cccc6ccc3c4c56)ccc2-c2ccc(-c3ccc4ccc5cccc6ccc3c4c56)cc21] H11
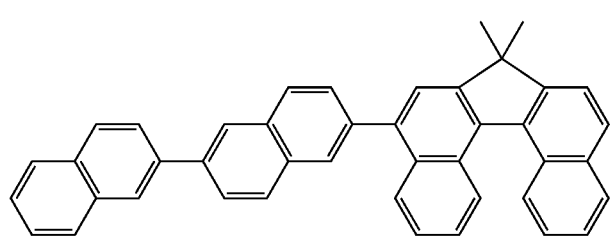 [SMILES: CC1(C)c2ccc3ccccc3c2-c2c1cc(-c1ccc3cc(-c4ccc5ccccc5c4)ccc3c1)c1ccccc21] H12

TABLE 2-continued
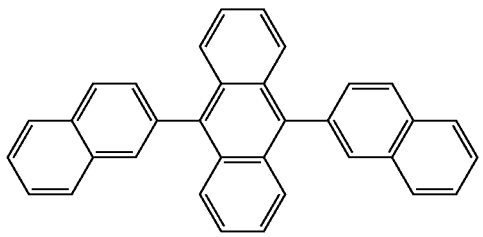 [SMILES: c1ccc2cc(-c3c4ccccc4c(-c4ccc5ccccc5c4)c4ccccc34)ccc2c1] H13
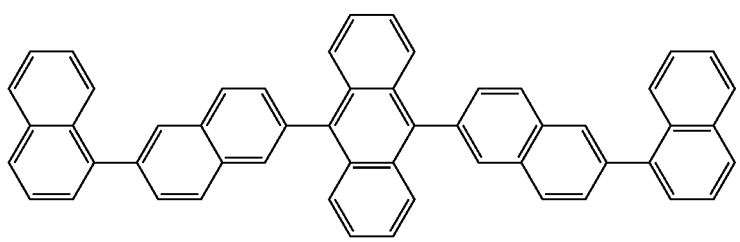 [SMILES: c1ccc2c(-c3ccc4cc(-c5c6ccccc6c(-c6ccc7cc(-c8cccc9ccccc89)ccc7c6)c6ccccc56)ccc4c3)cccc2c1] H14
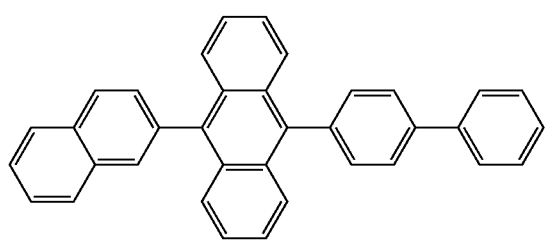 [SMILES: c1ccc(-c2ccc(-c3c4ccccc4c(-c4ccc5ccccc5c4)c4ccccc34)cc2)cc1] H15
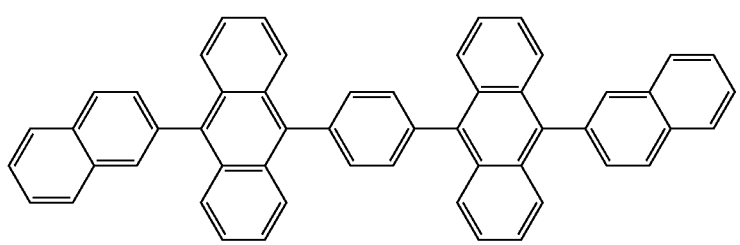 [SMILES: c1ccc2cc(-c3c4ccccc4c(-c4ccc(-c5c6ccccc6c(-c6ccc7ccccc7c6)c6ccccc56)cc4)c4ccccc34)ccc2c1] H16
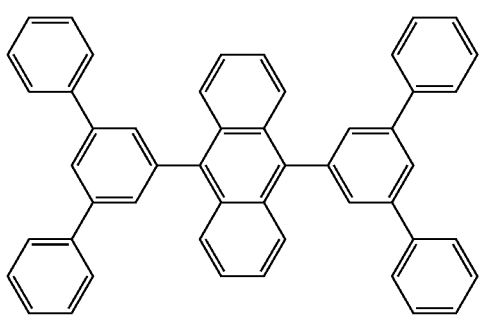 [SMILES: c1ccc(-c2cc(-c3ccccc3)cc(-c3c4ccccc4c(-c4cc(-c5ccccc5)cc(-c5ccccc5)c4)c4ccccc34)c2)cc1] H17
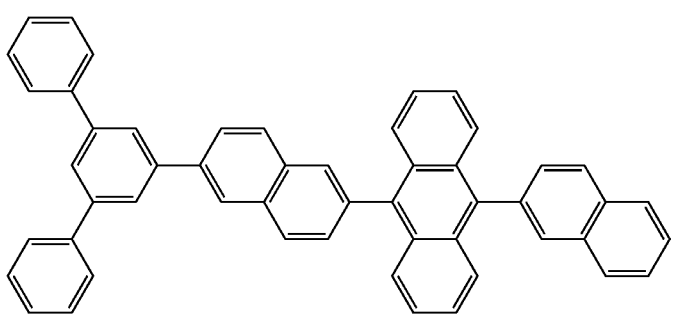 [SMILES: c1ccc(-c2cc(-c3ccccc3)cc(-c3ccc4cc(-c5c6ccccc6c(-c6ccc7ccccc7c6)c6ccccc56)ccc4c3)c2)cc1] H18

TABLE 2-continued
| | |
|---|---|
| 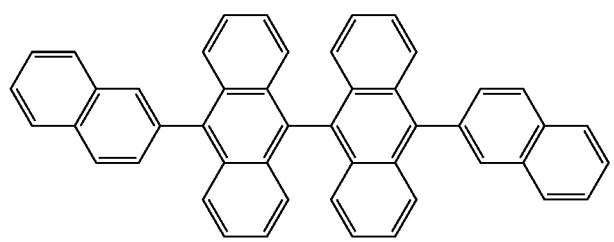 [SMILES: c1ccc2cc(-c3c4ccccc4c(-c4c5ccccc5c(-c5ccc6ccccc6c5)c5ccccc45)c4ccccc34)ccc2c1] | H19 |
| 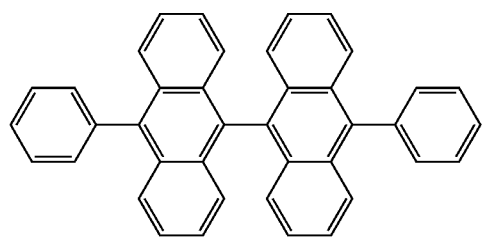 [SMILES: c1ccc(-c2c3ccccc3c(-c3c4ccccc4c(-c4ccccc4)c4ccccc34)c3ccccc23)cc1] | H20 |
| 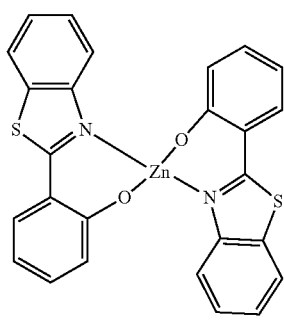 | H21 |
| 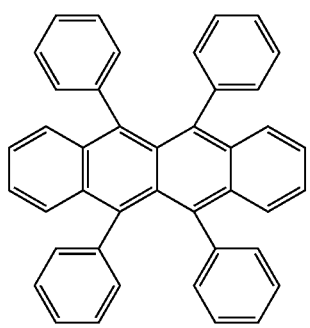 [SMILES: c1ccc(-c2c3ccccc3c(-c3ccccc3)c3c(-c4ccccc4)c4ccccc4c(-c4ccccc4)c23)cc1] | H22 |
| 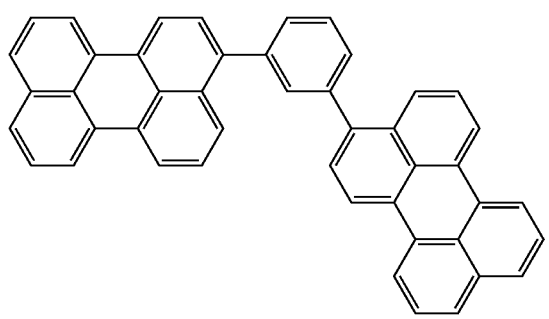 [SMILES: c1cc(-c2ccc3c4cccc5cccc(c6cccc2c63)c54)cc(-c2ccc3c4cccc5cccc(c6cccc2c63)c54)c1] | H23 |

TABLE 2-continued

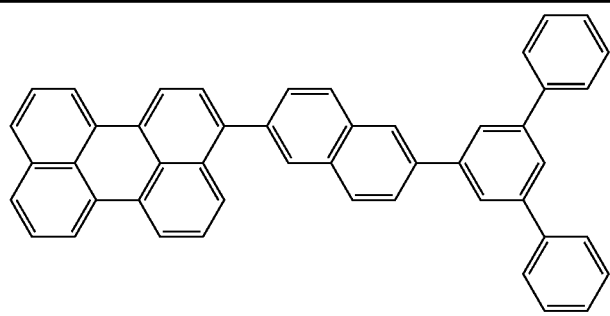

H24

Examples of the host include, but of course not limited to: condensed ring compounds (such as a fluorene derivative, a naphthalene derivative, an anthracene derivative, a pyrene derivative, a carbazole derivative, a quinoxaline derivative, and a quinoline derivative); an organic aluminum complex such as tris(8-quinolinolato)aluminum; an organozinc complex; and polymer derivatives such as a triphenylamine derivative, a poly(fluorene) derivative, and a poly(phenylene) derivative in addition to the group of compounds represented in Table 2.

The electron injectable/transportable material can be arbitrarily selected from materials that allow electrons to be easily injected from the cathode and can transport the injected electrons to the emission layer in consideration of, for example, the balance with the hole mobility of the hole transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex.

A constituent material for the anode desirably has as large a work function as possible. Examples thereof may include: metal simple substances such as gold, platinum, silver, copper, nickel, palladium, cobalt, selenium, vanadium, and tungsten or alloys obtained by combining these metal simple substances; metal oxides such as tin oxide, zinc oxide, indium oxide, indium tin oxide (ITO), and indium zinc oxide; and conductive polymers such as polyaniline, polypyrrole, and polythiophene.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: alkali metals such as lithium; alkaline earth metals such as calcium; and metal simple substances such as aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole injection layer, the hole transport layer, the electron blocking layer, the emission layer, the hole blocking layer, the electron transport layer, or the electron injection layer) for forming the organic light emitting element of the present invention is formed by the following method.

A dry process such as a vacuum vapor deposition method, an ionized vapor deposition method, sputtering, or a plasma process can be used for the formation of the organic compound layer for forming the organic light emitting element of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum vapor deposition method, the solution application method, or the like, the layer hardly undergoes crystallization or the like and is excellent in stability over time. In addition, when the layer is formed by the application method, the film can be formed by using the constituent materials in combination with an appropriate binder resin.

Examples of the binder resin include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

The light that the organic light emitting element of the present invention emits may be any one of blue, green, and red lights, and may be a light of a color obtained by mixing multiple luminescent colors selected from blue, green, and red, e.g., a white color obtained by mixing blue, green, and red.

(4) Application of Organic Light Emitting Element

The organic light emitting element of the present invention can be used as a constituent member for a display apparatus or lighting apparatus. In addition, the element finds use in applications such as an exposure light source for an image forming apparatus of an electrophotographic system, a backlight for a liquid crystal display apparatus, and a light emitting apparatus including a white light source and a color filter. Examples of the color filter include filters that transmit light beams having three colors, i.e., red, green, and blue colors.

A display apparatus of the present invention includes the organic light emitting element of the present invention in its display portion. It should be noted that the display portion includes multiple pixels.

In addition, the pixels each have the organic light emitting element of the present invention and a transistor as an example of an active element (switching element) or amplifying element for controlling emission luminance, and the anode or cathode of the organic light emitting element and the drain electrode or source electrode of the transistor are electrically connected to each other. Here, the display apparatus can be used as an image display apparatus for a PC or the like. The transistor is, for example, a TFT element and the TFT element is provided on, for example, the insulating surface of a substrate. In addition, the TFT element preferably includes an electrode formed of a transparent oxide semiconductor.

The display apparatus may be an image information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

A lighting apparatus of the present invention includes the organic light emitting element of the present invention and an AC/DC converter circuit (circuit for converting an AC voltage into a DC voltage) connected to the organic light emitting element and supplying a driving voltage to the organic light emitting element. It should be noted that the lighting apparatus may further have a color filter.

An image forming apparatus of the present invention is an image forming apparatus including: a photosensitive member; a charging portion for charging the surface of the photosensitive member; an exposure portion for exposing the photosensitive member to form an electrostatic latent image; and a developing device for developing the electrostatic latent image formed on the surface of the photosensitive member. Here, the exposing means to be provided in the image forming apparatus includes the organic light emitting element of the present invention.

In addition, the organic light emitting element of the present invention can be used as a constituent member (light emitting member) for an exposing apparatus for exposing a photosensitive member. An exposing apparatus including a plurality of the organic light emitting elements of the present invention is, for example, an exposing apparatus in which the organic light emitting elements of the present invention are placed to form a line along a predetermined direction.

Next, the display apparatus of the present invention is described with reference to the drawing. FIG. 1 is a schematic sectional view illustrating an example of a display apparatus including an organic light emitting element and a switching element connected to the organic light emitting element. It should be noted that the organic light emitting element of the present invention is used as the organic light emitting element constituting a display apparatus 1 of FIG. 1.

The display apparatus 1 of FIG. 1 includes a substrate 11 made of glass or the like and a moisture-proof film 12 for protecting a TFT element 18 or organic compound layer as the switching element, the film being formed on the substrate. In addition, a metal gate electrode 13 is represented by reference numeral 13, a gate insulating film 14 is represented by reference numeral 14, and a semiconductor layer is represented by reference numeral 15.

A TFT element 18 includes the semiconductor layer 15, a drain electrode 16, and a source electrode 17. An insulating film 19 is formed on the TFT element 18. An anode 21 constituting the organic light emitting element and the source electrode 17 are connected to each other through a contact hole 20.

It should be noted that a system for the electrical connection between the electrode (anode or cathode) in the organic light emitting element and the electrode (source electrode or drain electrode) in the TFT is not limited to the aspect illustrated in FIG. 1. In other words, one of the anode and the cathode, and one of the source electrode and drain electrode of the TFT element have only to be electrically connected to each other.

Although multiple organic compound layers are illustrated like one layer in the display apparatus 1 of FIG. 1, an organic compound layer 22 may be multiple layers. A first protective layer 24 and second protective layer 25 for suppressing the deterioration of the organic light emitting element are formed on a cathode 23.

When the display apparatus 1 of FIG. 1 is a display apparatus that emits white light, an emission layer in the organic compound layer 22 in FIG. 1 may be a layer obtained by mixing a red light emitting material, a green light emitting material, and a blue light emitting material. In addition, the layer may be a laminated emission layer obtained by laminating a layer formed of the red light emitting material, a layer formed of the green light emitting material, and a layer formed of the blue light emitting material. Further, alternatively, the following aspect is permitted: the layer formed of the red light emitting material, the layer formed of the green light emitting material, and the layer formed of the blue light emitting material are, for example, arranged side by side to form domains in one emission layer.

Although the transistor is used as the switching element in the display apparatus 1 of FIG. 1, an MIM element may be used instead of the transistor as the switching element.

In addition, the transistor to be used in the display apparatus 1 of FIG. 1 is not limited to a transistor using a single crystal silicon wafer and may be a thin-film transistor including an active layer on the insulating surface of a substrate. A thin-film transistor using single crystal silicon as the active layer, a thin-film transistor using non-single crystal silicon such as amorphous silicon or microcrystalline silicon as the active layer, or a thin-film transistor using a non-single crystal oxide semiconductor such as an indium zinc oxide or an indium gallium zinc oxide as the active layer is also permitted. It should be noted that the thin-film transistor is also called a TFT element.

The transistor in the display apparatus 1 of FIG. 1 may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light emitting element is preferably provided in the Si substrate.

As described above, the driving of the display apparatus using the organic light emitting element of the present invention enables display that has good image quality and is stable over a long time period.

EXAMPLES

Hereinafter, the present invention is described in detail by way of Examples, provided that the present invention is not limited to Examples described below.

Example 1

Synthesis of Exemplified Compound A3

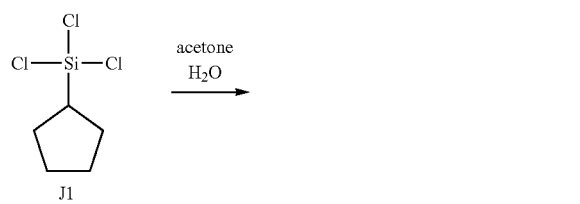

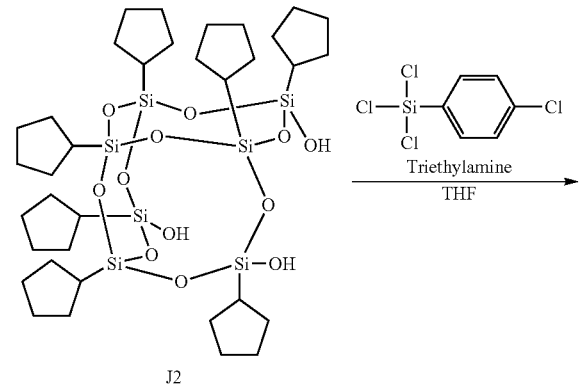

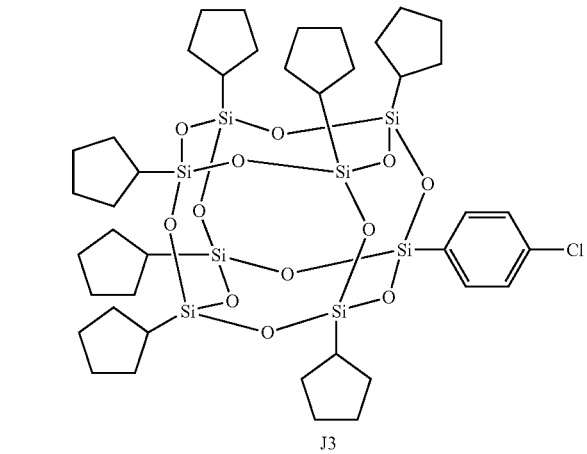

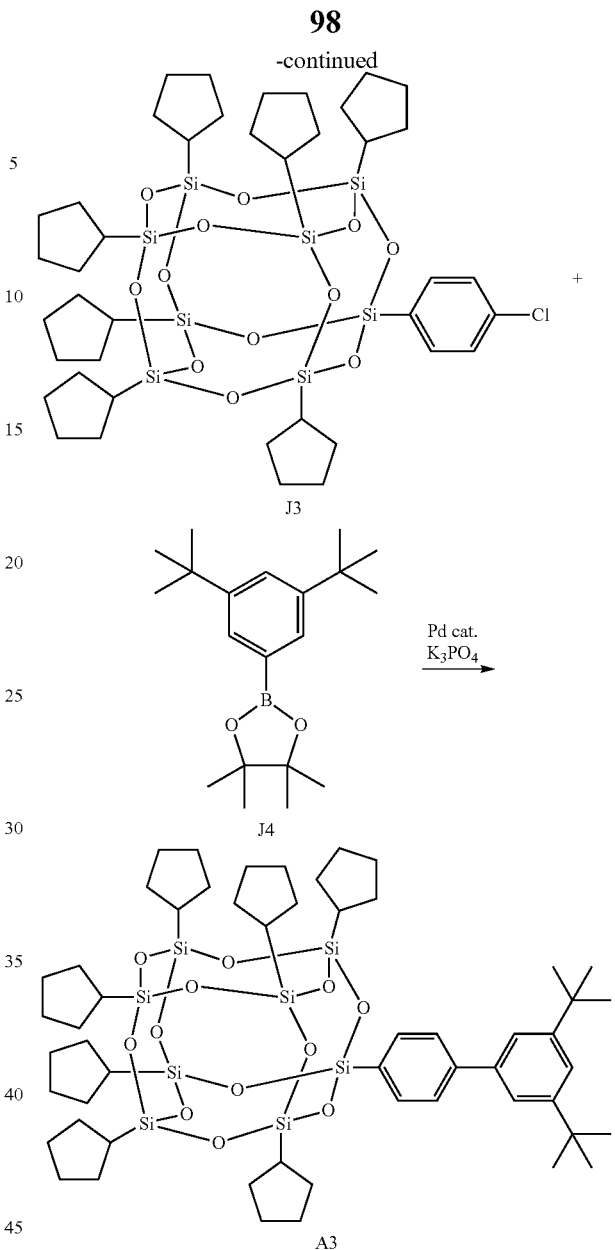

(1) Synthesis of Compound J2

The following reagent and solvent were charged into a reaction vessel.

Compound J1: 25 ml (150 mmol)
Acetone: 600 ml

Next, 170 ml of distilled water were dropped to the reaction solution. Next, the reaction solution was heated to 70° C. and then stirred at the temperature (70° C.) for 3 days. After the completion of the reaction, the suspension was filtered and washed with acetone. After that, pyridine was charged into the washed product to provide a pyridine solution. Next, the pyridine solution was brought into an acidic condition to produce a crystal. Next, the crystal was subjected to Soxhlet extraction with diethyl ether and chloroform to provide 6.3 g (yield: 33%) of Compound J2 as a white solid.

(2) Synthesis of Compound J3

The following reagents and solvent were charged into a reaction vessel.

Compound J2: 3.1 g (3.5 mmol)
Triethylamine: 1.0 g (10 mmol)
THF: 18 ml

Next, 0.93 g (3.8 mmol) of trichloro(4-chlorophenyl)silane was dropped to the reaction solution. Next, the reaction solution was stirred at room temperature for 12 hours and then the produced solid was taken by filtration. Next, the product taken by filtration was purified by silica gel column chromatography (developing solvent; heptane:chloroform=4:1) to provide 1.4 g (yield: 39%) of Compound J3 as a white solid.

(3) Synthesis of Exemplified Compound A3

The following reagents and solvent were charged into a reaction vessel.
Palladium acetate: 26 mg (0.12 mmol)
x-Phos: 160 mg (0.35 mmol)
Toluene: 3 ml Next, the reaction solution was stirred at room temperature for 15 minutes. Next, the following reagents and solvent were charged into the reaction solution.
Compound J3: 400 mg (1.3 mmol)
Compound J4: 1.2 g (1.2 mmol)
Potassium phosphate: 980 mg (4.6 mmol)
Water: 0.53 ml Next, the reaction solution was heated to 95° C. and then stirred at the temperature (95° C.) for 5 hours. After the completion of the reaction, the reaction solution was cooled. After that, 20 ml of heptane were added to the solution and then the mixture was purified by silica gel column chromatography (developing solvent; heptane:chloroform=10:1) to provide 730 mg (yield: 54%) of Exemplified Compound A3 as a white solid.

Mass spectrometry based on LC-MS involving using a Micromass ZQ manufactured by Waters confirmed 1,166 as the $M^+$ of Exemplified Compound A3.

Example 2

Synthesis of Exemplified Compound A6

Exemplified Compound A6 was synthesized by the same method as that of Example 1 except that Compound J5 shown below was used instead of Compound J4 in the section (3) of Example 1.

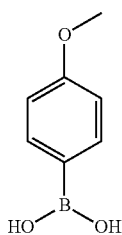

J5

The same analysis method as that of Example 1 (mass spectrometry based on LC-MS) confirmed 1,084 as the $M^+$ of Exemplified Compound A6.

Example 3

Synthesis of Exemplified Compound A9

Exemplified Compound A9 was synthesized by the same method as that of Example 1 except that Compound J6 shown below was used instead of Compound J4 in the section (3) of Example 1.

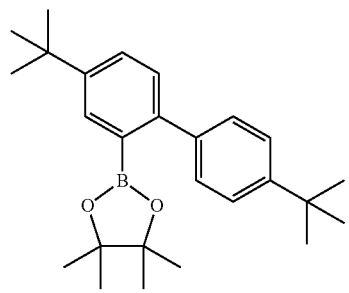

J6

The same analysis method as that of Example 1 (mass spectrometry based on LC-MS) confirmed 1,084 as the $M^+$ of Exemplified Compound A9.

Example 4

Synthesis of Exemplified Compound A11

Exemplified Compound A11 was synthesized by the same method as that of Example 1 except that Compound J7 shown below was used instead of Compound J4 in the section (3) of Example 1.

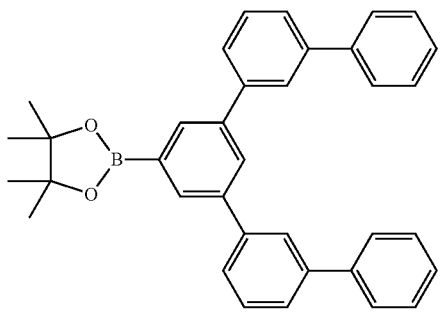

J7

The same analysis method as that of Example 1 (mass spectrometry based on LC-MS) confirmed 1,358 as the $M^+$ of Exemplified Compound A11.

Example 5

Synthesis of Exemplified Compound A15

Exemplified Compound A15 was synthesized by the same method as that of Example 1 except that Compound J8 shown below was used instead of Compound J4 in the section (3) of Example 1.

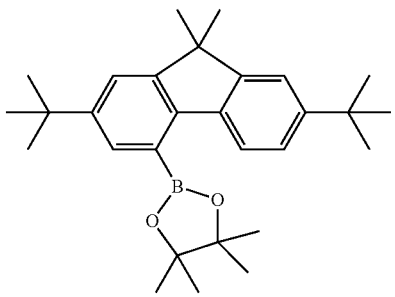

J8

Example 6

Synthesis of Exemplified Compound A19

Exemplified Compound A19 was synthesized by the same method as that of Example 1 except that Compound J9 shown below was used instead of Compound J4 in the section (3) of Example 1.

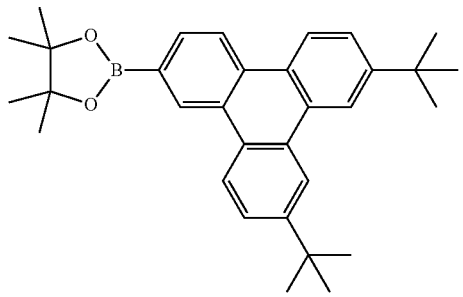

J9

The same analysis method as that of Example 1 (mass spectrometry based on LC-MS) confirmed 1,316 as the M+ of Exemplified Compound A19.

Example 7

Synthesis of Exemplified Compound A24

Exemplified Compound A24 was synthesized by the same method as that of Example 1 except that: Compound J10 shown below was used instead of Compound J1 in the section (1) of Example 1; and Compound J11 shown below was used instead of Compound J4 in the section (3) of Example 1.

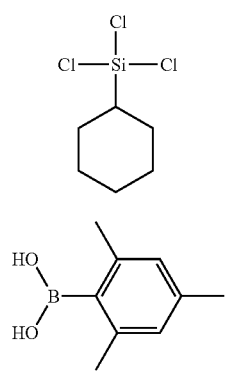

The same analysis method as that of Example 1 (mass spectrometry based on LC-MS) confirmed 1,194 as the M+ of Exemplified Compound A19.

Example 8

Synthesis of Exemplified Compound B1

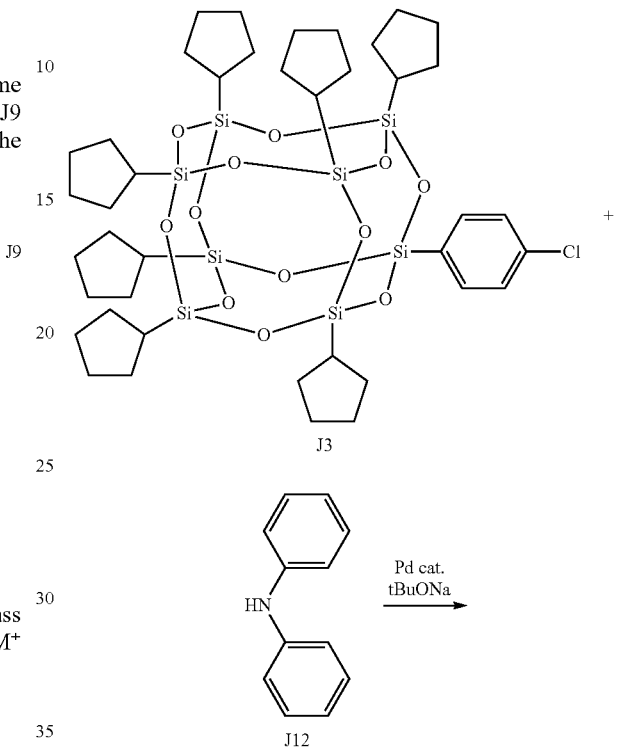

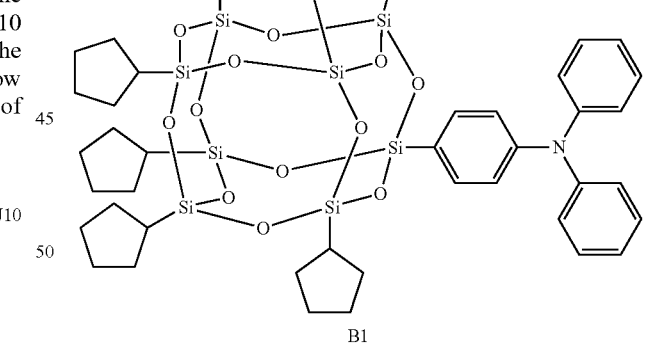

B1

The following reagents and solvent were charged into a reaction vessel.
Tris(dibenzylideneacetone)dipalladium(0): 23 mg (0.025 mmol)
x-Phos: 47 mg (0.10 mmol)
Toluene: 5 ml
Next the reaction solution was stirred at room temperature for 15 minutes. After that, the following reagents were charged into the reaction solution.
Compound J3: 500 mg (0.49 mmol)
Compound J12: 88 mg (0.52 mmol)
t-Butoxysodium: 95 mg (0.99 mmol)

Next, the reaction solution was heated to 120° C. and then stirred at the temperature (120° C.) for 5 hours. After the completion of the reaction, the reaction solution was cooled and then an organic layer was extracted with toluene. Next, the extracted organic layer was dried and then the solvent was removed by distillation under reduced pressure to provide a coarse product. Next, the coarse product was purified by silica gel column chromatography (developing solvent; heptane:toluene=5:1) to provide 368 mg (yield: 65%) of Exemplified Compound B1 as a white solid.

Mass spectrometry based on MALDI confirmed 1,145 as the M⁺ of Exemplified Compound B1.

Example 9

Synthesis of Exemplified Compound B5

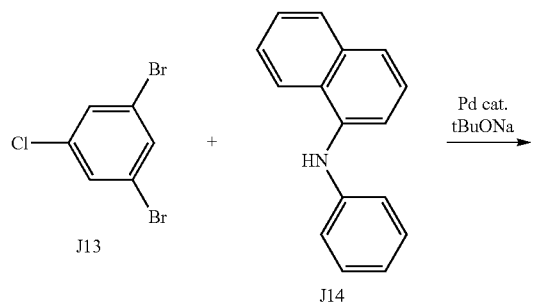

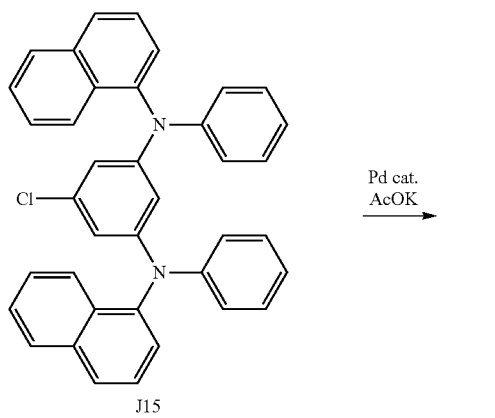

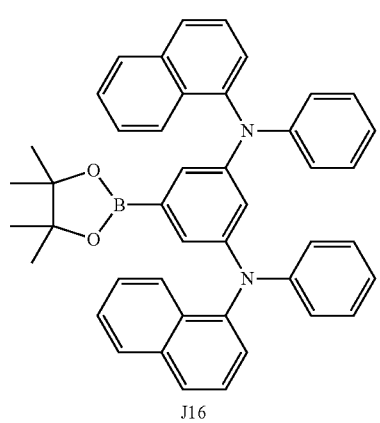

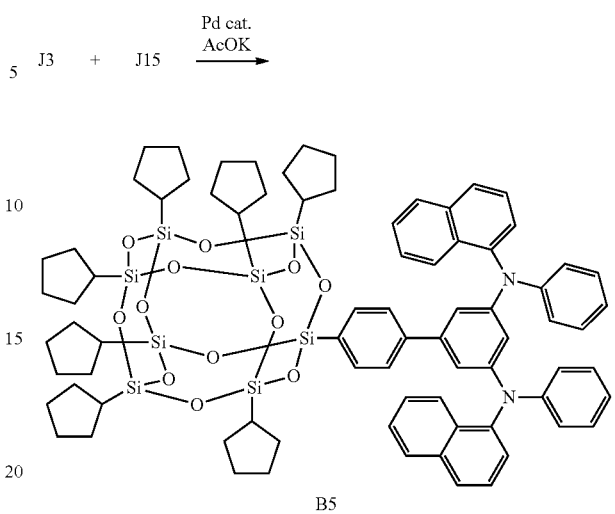

B5

(1) Synthesis of Compound J15

The following reagents and solvent were charged into a reaction vessel.

Tris(dibenzylideneacetone)dipalladium(0): 190 mg (0.21 mmol)
Tri(t-butyl)phosphine: 170 mg (0.82 mmol)
Toluene: 20 ml Next, the reaction solution was stirred at room temperature for 15 minutes. After that, the following reagents were charged into the reaction solution.

Compound J13: 560 mg (2.1 mmol)
Compound J14: 1.0 g (4.6 mmol)
t-Butoxysodium: 880 mg (9.1 mmol)

Next, the reaction solution was heated to 100° C. and then stirred at the temperature (100° C.) for 3 hours. After the completion of the reaction, the reaction solution was cooled and then an organic layer was extracted with toluene. Next, the extracted organic layer was dried and then the solvent was removed by distillation under reduced pressure to provide a coarse product. Next, the coarse product was purified by silica gel column chromatography (developing solvent; heptane:toluene=3:1) to provide 760 mg (yield: 67%) of Compound J15.

(2) Synthesis of Compound J16

The following reagents and solvent were charged into a reaction vessel.

Palladium acetate: 31 mg (0.14 mmol)
x-Phos: 130 mg (0.27 mmol)
1,4-Dioxane: 10 ml Next, the reaction solution was stirred at room temperature for 15 minutes. After that, the following reagents were charged into the reaction solution.

Compound J15: 750 mg (1.4 mmol)
Bis(pinacolato)diboron: 670 mg (2.7 mmol)
Potassium acetate: 400 mg (4.1 mmol)

Next, the reaction solution was heated to 100° C. and then stirred at the temperature (100° C.) for 6 hours. After the completion of the reaction, the reaction solution was cooled and then an organic layer was extracted with toluene. Next, the extracted organic layer was dried and then the solvent was removed by distillation under reduced pressure to provide a coarse product. Next, the coarse product was purified by silica gel column chromatography (developing solvent; heptane:toluene=1:1) to provide 490 mg (yield: 55%) of Compound J16.

(3) Synthesis of Exemplified Compound B5

The following reagents and solvent were charged into a reaction vessel.

Tris(dibenzylideneacetone)dipalladium(0): 45 mg (0.049 mmol)

x-Phos: 70 mg (0.16 mmol)

1,4-Dioxane: 5 ml

Next, the reaction solution was stirred at room temperature for 15 minutes. After that, the following reagents were charged into the reaction solution.

Compound J3: 500 mg (0.49 mmol)
Compound J16: 350 mg (0.54 mmol)
Potassium acetate: 99 mg (0.99 mmol)

Next, the reaction solution was heated to 100° C. and then stirred at the temperature (100° C.) for 6 hours. After the completion of the reaction, the reaction solution was cooled and then added with methanol. The resulting precipitate was filtered and then the precipitate was purified by silica gel column chromatography (developing solvent; heptane:toluene=7:1) to provide 370 mg (yield: 56%) of Exemplified Compound B5 as a white solid.

Mass spectrometry based on MALDI confirmed 1,488 as the M+ of Exemplified Compound B5.

Example 10

Synthesis of Exemplified Compound B16

(1) Synthesis of Compound J10A

Compound J10A was synthesized by the same method as that of the section (1) of Example 1 except that Compound J10 was used instead of Compound J1 in the section (1) of Example 1.

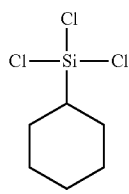

J10

(2) Synthesis of Compound J15A

Compound J15A was synthesized by the same method as that of the section (1) of Example 9 except that Compound J17 shown below was used instead of Compound J14 in the section (1) of Example 9.

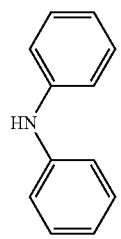

J17

(3) Synthesis of Compound J16A

Compound J16A was synthesized by the same method as that of of the section (2) of Example 9 except that Compound J15A synthesized in the section (2) was used instead of Compound J15 in the section (2) of Example 9.

(4) Synthesis of Exemplified Compound B16

Exemplified Compound B16 was synthesized by the same method as that of the section (3) of Example 9 except that Compound J10A was used instead of Compound J3 and Compound J16A was used instead of Compound J16 in the section (3) of Example 9.

Mass spectrometry based on MALDI confirmed 1,486 as the M+ of Exemplified Compound B16.

Example 11

Synthesis of Exemplified Compound C3

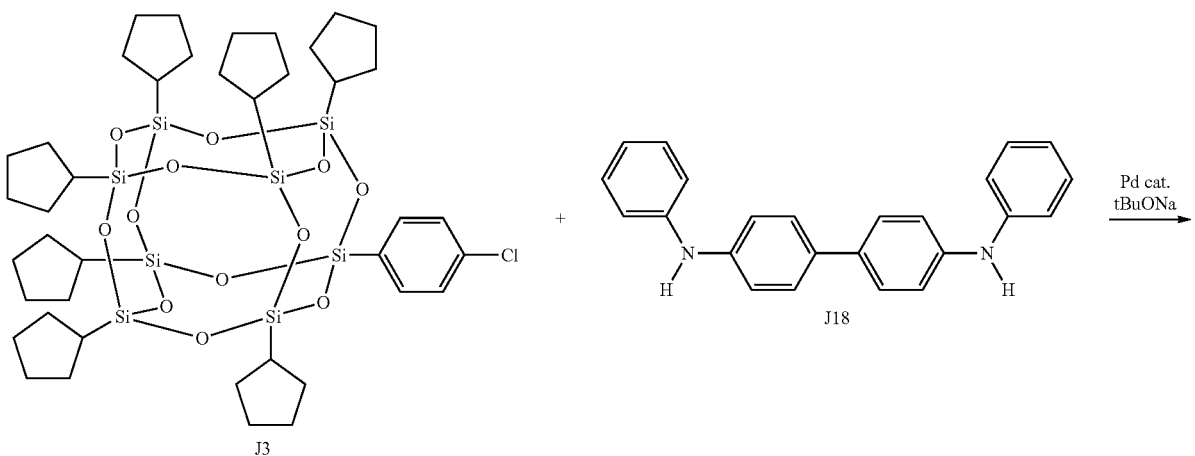

-continued

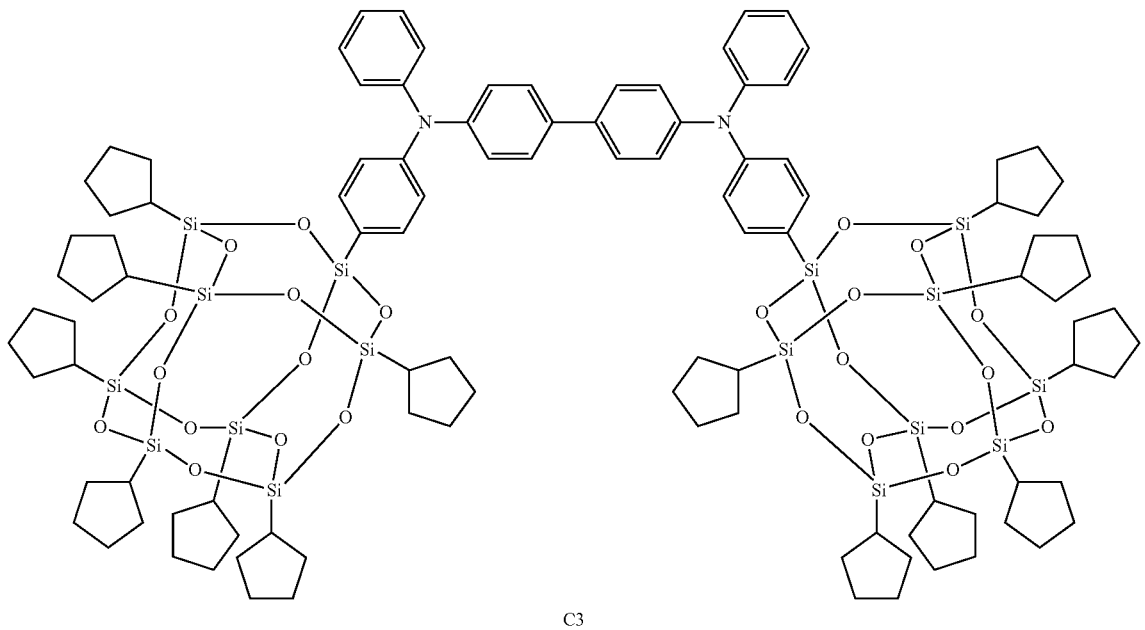

C3

The following reagents and solvent were charged into a reaction vessel.

Tris(dibenzylideneacetone)dipalladium(0): 45 mg (0.05 mmol)

x-Phos: 71 mg (0.15 mmol)

Toluene: 5 ml

Next, the reaction solution was stirred at room temperature for 15 minutes. After that, the following reagents were charged into the reaction solution.

Compound J3: 1.0 g (0.99 mmol)

Compound J18: 160 mg (0.47 mmol)

t-Butoxysodium: 170 mg (1.9 mmol)

Next, the reaction solution was heated to 120° C. and then stirred at the temperature (120° C.) for 5 hours. After the completion of the reaction, the reaction solution was cooled and then an organic layer was extracted with toluene. Next, the extracted organic layer was dried and then the solvent was removed by distillation under reduced pressure to provide a coarse product. Next, the coarse product was purified by sequentially performing hot filtration and dispersion washing with heptane, thereby providing 790 mg (yield: 73%) of Exemplified Compound C3 as a white solid.

Mass spectrometry based on MALDI confirmed 2,288 as the $M^+$ of Exemplified Compound C3.

Example 12

Synthesis of Exemplified Compound C5

Exemplified Compound C5 was synthesized by the same method as that of Example 11 except that Compound J19 shown below was used instead of Compound J18 in Example 11.

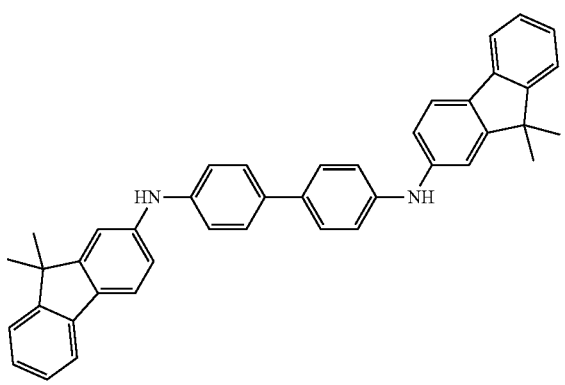

J19

Mass spectrometry based on MALDI confirmed 2,520 as the $M^+$ of Exemplified Compound C5.

Example 13
Synthesis of Exemplified Compound C6
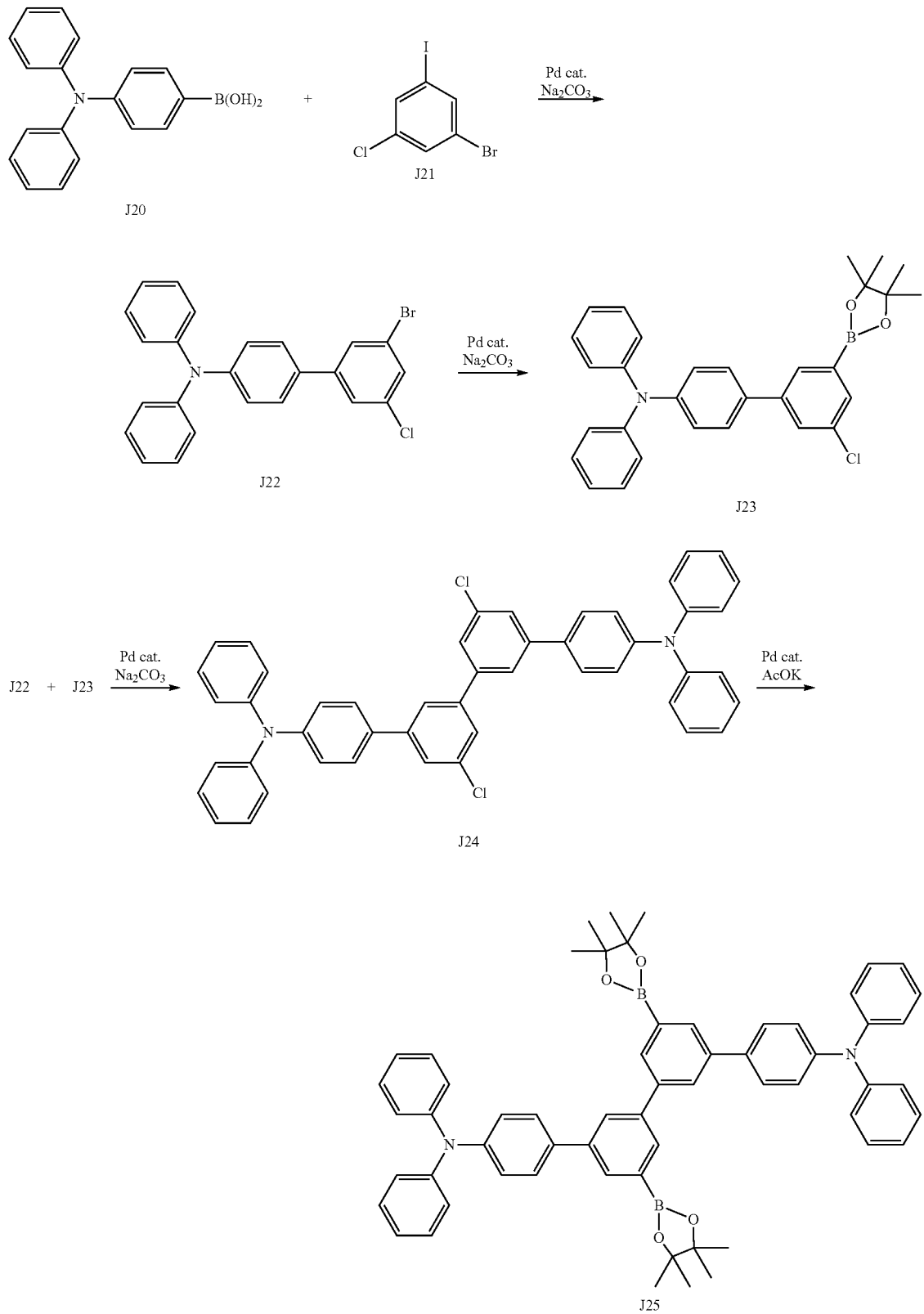

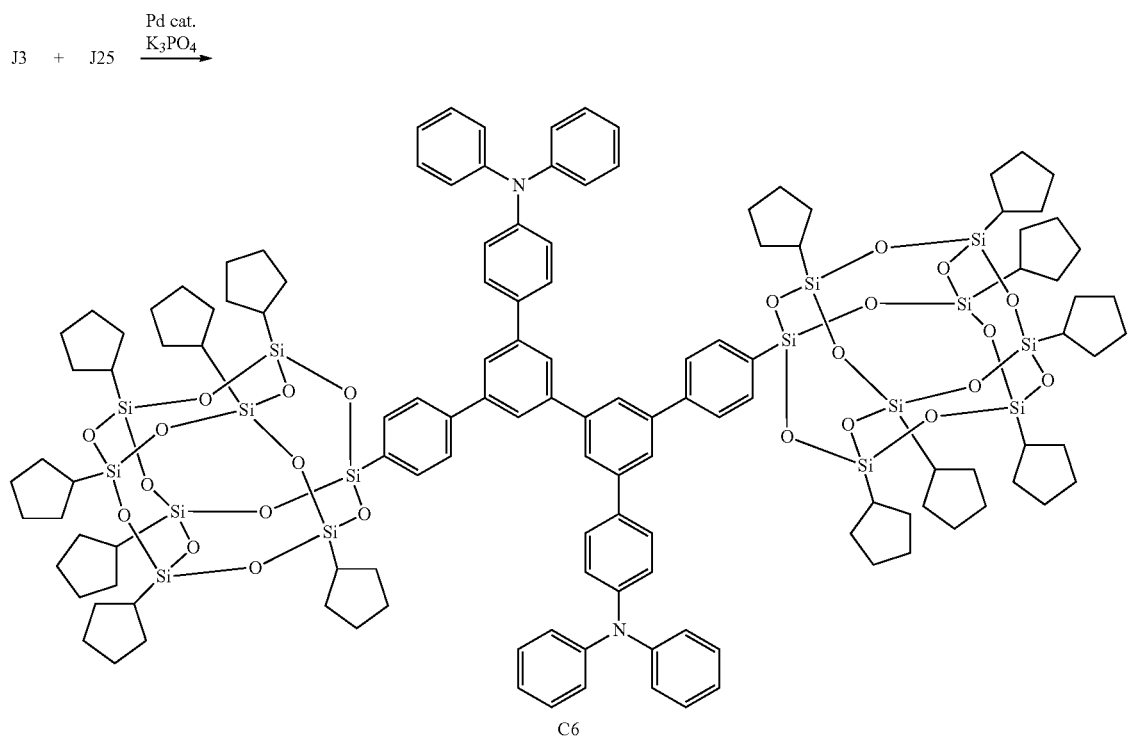

C6

(1) Synthesis of Compound J22

The following reagents and solvents were charged into a reaction vessel.

Compound J20: 1.44 g (5.00 mmol)
Compound J21: 2.11 g (6.33 mmol)
Toluene: 10 ml
Ethanol: 10 ml
10 mass % Sodium carbonate aqueous solution: 20 ml Next, 288 mg (0.0025 mmol) of tetrakis triphenylphosphine palladium(0) were added to the reaction solution and then the reaction solution was heated to 90° C. and stirred at the temperature (90° C.) for 5 hours. After the completion of the reaction, the reaction solution was cooled and then an organic layer was extracted with toluene. Next, the extracted organic layer was dried and then the solvent was removed by distillation under reduced pressure to provide a coarse product. Next, the coarse product was purified by silica gel column chromatography (developing solvent; heptane:chloroform=2:1) to provide 1.55 g (yield: 72%) of Compound J22.

(2) Synthesis of Compound J23

The following reagents and solvents were charged into a reaction vessel.

Compound J22: 1.0 g (2.3 mmol)
Bis(pinacolato)diboron: 1.17 g (4.6 mmol)
Potassium acetate: 0.68 g (6.9 mmol)
[1,1'-bis(diphenylphosphino)ferrocene]palladium(II)dichloride (dichloromethane adduct): 94 mg
1,4-dioxane: 300 ml Next, the reaction solution was heated to 100° C. and then stirred at the temperature (100° C.) for 4 hours. After the completion of the reaction, the reaction solution was cooled and then the reaction solution was concentrated under reduced pressure to provide a coarse product. Next, the coarse product was purified by silica gel column chromatography (developing solvent; heptane:chloroform=2:1) to provide 0.95 g (yield: 85%) of Compound J23.

(3) Synthesis of Compound J24

The following reagents and solvents were charged into a reaction vessel.

Compound J22: 0.696 g (1.60 mmol)
Compound J23: 0.80 g (1.66 mmol)
Toluene: 20 ml
Ethanol: 10 ml
10 mass % Sodium carbonate aqueous solution: 20 ml Next, 96 mg of tetrakis triphenylphosphine palladium(0) were added to the reaction solution and then the reaction solution was heated to 90° C. and stirred at the temperature (90° C.) for 5 hours. After the completion of the reaction, the reaction solution was cooled and then an organic layer was extracted with toluene. Next, the extracted organic layer was dried and then the solvent was removed by distillation under reduced pressure to provide a coarse product. Next, the coarse product was purified by silica gel column chromatography (developing solvent; heptane:toluene=7:1) to provide 1.10 g (yield: 97%) of Compound J24.

(4) Synthesis of Compound J25

The following reagents and solvent were charged into a reaction vessel.

Palladium dibenzylideneacetone: 81 mg
s-Phos: 135 mg
1,4-Dioxane: 30 ml

Next, the reaction solution was stirred at room temperature for 15 minutes. After that, the following reagents were charged into the reaction solution.

Compound J24: 1.0 g (1.41 mmol)
Bis(pinacolato)diboron: 1.79 g (7.05 mmol)
Potassium acetate: 829 mg (8.46 mmol)

Next, the reaction solution was heated to 100° C. and then stirred at the temperature (100° C.) for 7 hours. After the completion of the reaction, the reaction solution was cooled. Next, the solution was purified by silica gel column chromatography (developing solvent; heptane:chloroform=1:1) to provide 943 mg (yield: 75%) of Compound J25.

(5) Synthesis of Exemplified Compound C6

The following reagents and solvent were charged into a reaction vessel.

Palladium dibenzylideneacetone: 23 mg
s-Phos: 43 mg
Toluene: 3 ml

Next, the reaction solution was stirred at room temperature for 15 minutes. After that, the following reagents and solvent were charged into the reaction solution.

Compound J3: 545 mg (0.538 mmol)
Compound J25: 200 g (0.224 mmol)
Potassium phosphate: 285 mg (1.34 mmol)
Water: 0.53 ml Next, the reaction solution was heated to 95° C. and then stirred at the temperature (95° C.) for 7 hours. After the completion of the reaction, the reaction solution was cooled. Next, 20 ml of heptane were added to the reaction solution and then the mixture was purified by silica gel column chromatography (developing solvent; heptane:chloroform=3:1) to provide 65 mg (yield: 11%) of Exemplified Compound C6 as a white solid.

Mass spectrometry based on MALDI confirmed 2,592 as the $M^+$ of Exemplified Compound C6.

Example 14

Synthesis of Exemplified Compound C24

(1) Synthesis of Compound J10A

Compound J10A was synthesized by the same method as that of the section (1) of Example 1 except that Compound J10 was used instead of Compound J1 in the section (1) of Example 1.

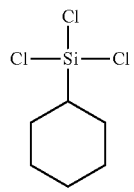

J10

(2) Synthesis of Exemplified Compound B16

Exemplified Compound C24 was synthesized by the same method as that of Example 11 except that Compound J10A was used instead of Compound J3 in Example 11.

Mass spectrometry based on MALDI confirmed 2,484 as the $M^+$ of Exemplified Compound C24.

Example 15

Synthesis of Exemplified Compound D2

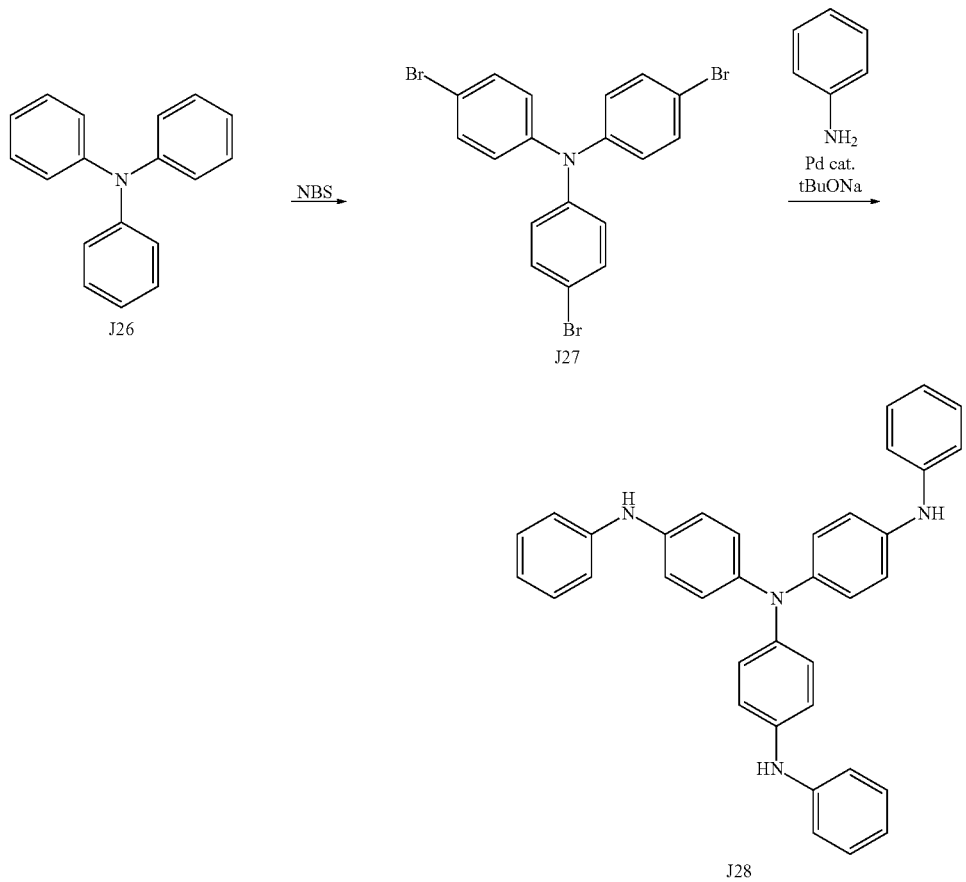

-continued

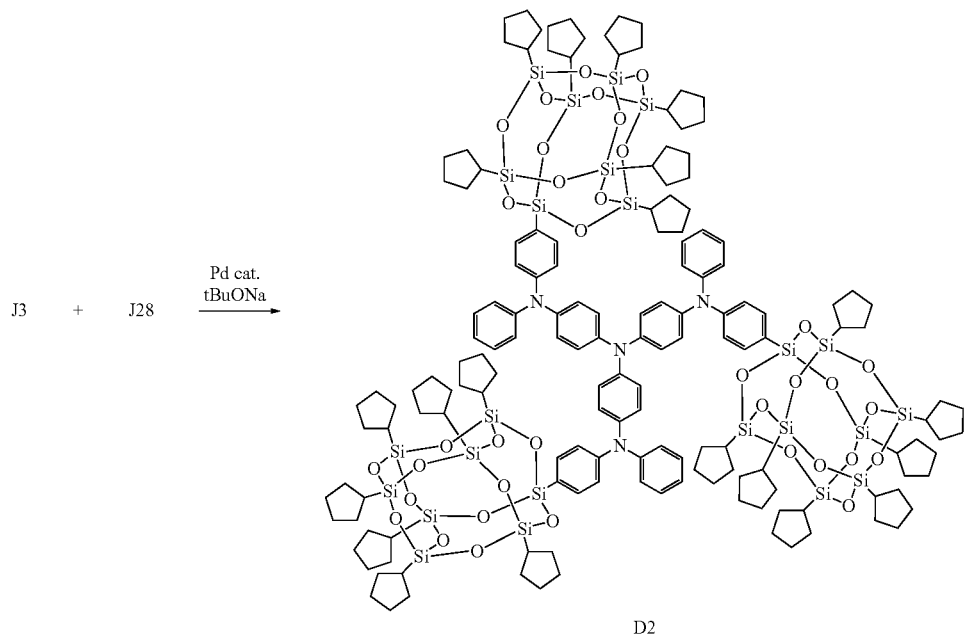

D2

(1) Synthesis of Compound J27

The following reagent and solvent were charged into a reaction vessel.

Compound J26: 0.50 g (2.0 mmol)
Dichloromethane: 20 ml

Next, NBS (1.2 g, 6.7 mmol) was added to the reaction vessel and then the reaction solution was stirred at room temperature for 12 hours. Next, a coarse product obtained by concentrating the reaction solution under reduced pressure was purified by silica gel column chromatography (mobile phase; toluene) and then subjected to dispersion washing with methanol, followed by recrystallization with a mixed solvent of heptane and methanol. Thus, 470 mg (yield: 48%) of Compound J27 were obtained.

(2) Synthesis of Compound J28

The following reagents and solvent were charged into a reaction vessel.

Tris(dibenzylideneacetone)dipalladium(0): 48 mg (0.052 mmol)
Tri(t-butyl)phosphine: 42 mg (0.21 mmol)
Toluene: 5 ml Next, the reaction solution was stirred at room temperature for 15 minutes. After that, the following reagents and a solvent were charged into the reaction solution.

Compound J27: 250 mg (0.52 mmol)
Aniline: 580 mg (6.2 mmol)
t-Butoxysodium: 600 mg (6.2 mmol)

Next, the reaction solution was heated to 100° C. and then stirred at the temperature (100° C.) for 3 hours. After the completion of the reaction, the reaction solution was cooled and then the reaction solution was concentrated under reduced pressure to provide a coarse product. Next, the coarse product was purified by silica gel column chromatography (developing solvent; toluene) to provide 150 mg (yield: 54%) of Compound J28.

(3) Synthesis of Exemplified Compound D2

The following reagents and solvent were charged into a reaction vessel.

Tris(dibenzylideneacetone)dipalladium(0): 29 mg (0.032 mmol)
x-Phos: 45 mg (0.095 mmol)
Toluene: 3 ml Next, the reaction solution was stirred at room temperature for 15 minutes. After that, the following reagents and a solvent were charged into the reaction solution.

Compound J3: 320 mg (0.32 mmol)
Compound J28: 50 mg (0.096 mmol)
t-Butoxysodium: 55 mg (0.58 mmol)

Next, the reaction solution was heated to 95° C. and then stirred at the temperature (95° C.) for 7 hours. After the completion of the reaction, the resultant was subjected to hot filtration with toluene and then purified by alumina column chromatography (developing solvent; toluene). Next, the purified product was recrystallized with a mixed solvent of toluene and ethanol to provide 100 mg (yield: 31%) of Exemplified Compound D2 as a white solid.

Mass spectrometry based on MALDI confirmed 3,446 as the $M^+$ of Exemplified Compound D2.

Comparative Example 1

Compound J29 shown below was used instead of Compound J4 in the section (3) of Example 1.

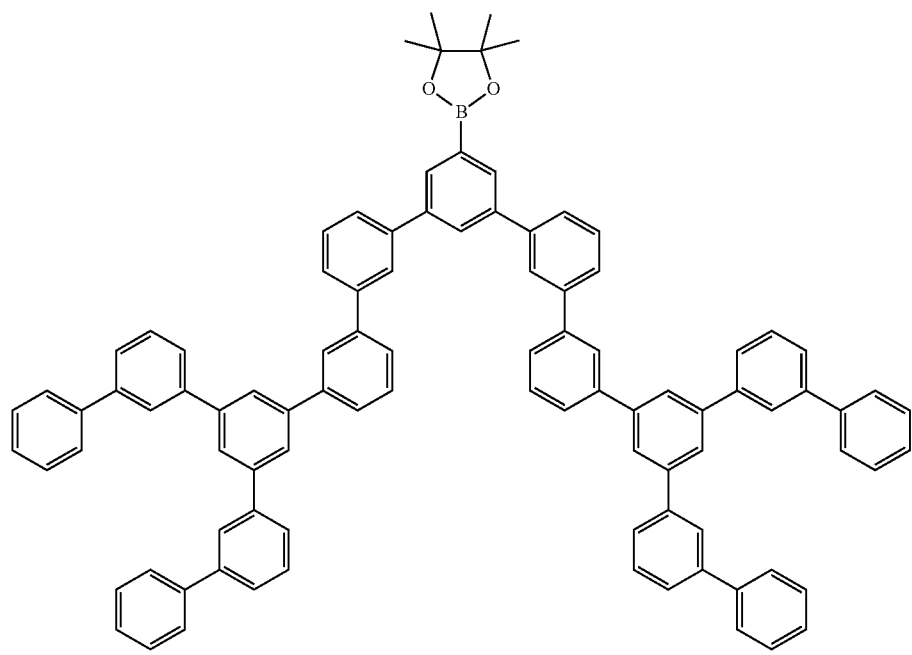
J29
Comparative Compound c-1 shown below was synthesized by the same method as that of Example 1 except the foregoing.
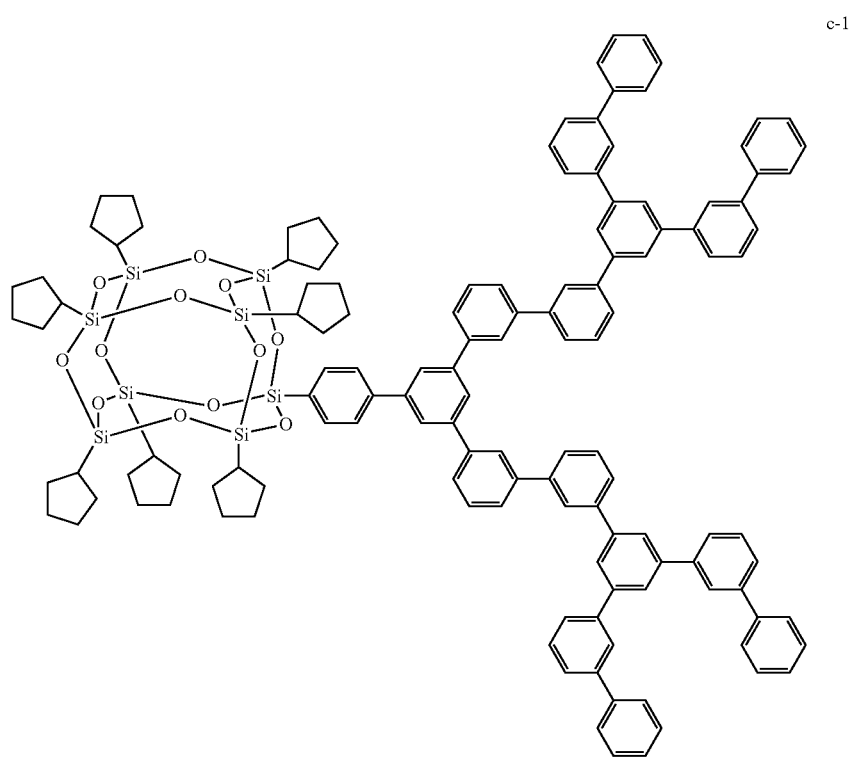 [SMILES: c1ccc(-c2cccc(-c3cc(-c4cccc(-c5ccccc5)c4)cc(-c4cccc(-c5cccc(-c6cc(-c7ccc([Si]89O[Si]%10(C%11CCCC%11)O[Si]%11(C%12CCCC%12)O[Si](C%12CCCC%12)(O8)O[Si]8(C%12CCCC%12)O[Si](C%12CCCC%12)(O9)O[Si](C9CCCC9)(O%10)O[Si](C9CCCC9)(O%11)O8)cc7)cc(-c7cccc(-c8cccc(-c9cc(-c%10cccc(-c%11ccccc%11)c%10)cc(-c%10cccc(-c%11ccccc%11)c%10)c9)c8)c7)c6)c5)c4)c3)c2)cc1]
c-1
Mass spectrometry based on MALDI confirmed 2,119 as the $M^+$ of Exemplified Compound c-1.

Example 16

In this example, an organic light emitting element in which an anode, a hole transport layer, an emission layer, a hole blocking layer, an electron transport layer, and a cathode were formed in the stated order on a substrate was produced by a method described below. In addition, part of the materials used in this example are listed below.

K1

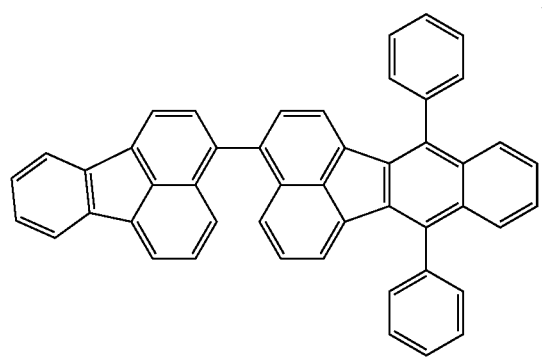

K2

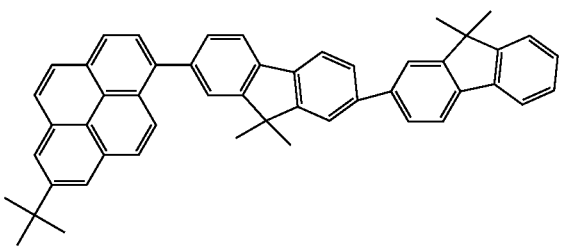

K3

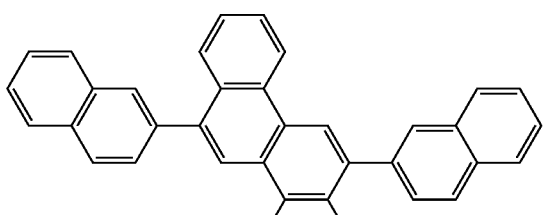

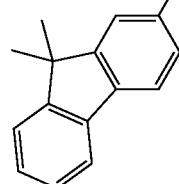

-continued

K4

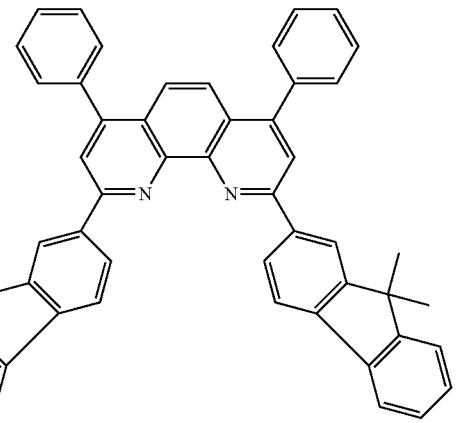

Indium tin oxide (ITO) was formed into a film on a glass substrate by a sputtering method. Thus, the anode was formed. At this time, the thickness of the anode was set to 120 nm. Next, the substrate with the anode was sequentially subjected to ultrasonic washing with acetone and isopropyl alcohol (IPA), and was then subjected to boil washing with IPA, followed by drying. Further, the dried product was subjected to UV/ozone washing. The substrate treated by the foregoing method was used as a transparent conductive supporting substrate in the following steps.

Next, a chloroform solution containing Exemplified Compound A6 (weight concentration: 75%) and the tertiary arylamine compound F-3 (weight concentration: 25%) was prepared. Next, the prepared chloroform solution was applied and formed into a film on the transparent conductive supporting substrate by a spin coating method to form the hole transport layer. At this time, the thickness of the hole transport layer was 30 nm. Next, organic compound layers and electrode layers shown in Table 3 below were continuously formed by vacuum deposition involving using resistance heating in a vacuum chamber at $1 \times 10^{-5}$ Pa to produce the organic light emitting element.

TABLE 3

|  | Constituent material | Thickness [nm] |
| --- | --- | --- |
| Emission layer | K1 (guest, weight concentration: 5%) K2 (host, weight concentration: 95%) | 20 |
| Hole blocking layer | K3 | 30 |
| Electron transport layer | K4 | 20 |
| First metal electrode layer (cathode) | Al | 150 |
| Second metal electrode layer (cathode) | LiF | 0.5 |

The resultant organic light emitting element had a light emitting efficiency at a luminance of 1,000 cd/m² of 9.0 cd/A and was observed to emit blue light having CIE chromaticity coordinates of (0.15, 0.26).

Examples 17 to 24 and Comparative Examples 2 to 6

An organic light emitting element was produced by the same method as that of Example 16 except that in Example 16, the constituent material for the hole transport layer was changed as shown in Table 4 below. The resultant organic light emitting element was evaluated for its element characteristics by the same method as that of Example 16. Table 4 shows the results.

TABLE 4

| | Hole transport layer | | | Light | |
|---|---|---|---|---|---|
| | Silses-quioxane compound (%) | Hole transport material (%) | Ratio of formula [1-1] (%)(Note 2) | emitting effi-ciency (cd/A) | CIE chromaticity coordinates |
| Example 16 | A6 (75) | YB-3 (25) | 25 | 9.0 | (0.15, 0.25) |
| Example 17 | C3 (67) | YB-3 (33) | 24 | 8.7 | (0.15, 0.25) |
| Example 18 | D2 (50) | YF-2 (50) | 22 | 8.3 | (0.15, 0.25) |
| Example 19 | A9 (75) | YB-3 (25) | 21 | 9.4 | (0.15, 0.25) |
| Example 20 | A15 (67) | YF-2 (33) | 15 | 9.4 | (0.15, 0.25) |
| Example 21 | B5 (75) | YB-4 (25) | 13 | 6.8 | (0.15, 0.25) |
| Example 22 | C6 (50) | YF-2 (50) | 12 | 5.5 | (0.15, 0.25) |
| Example 23 | X4 (75) | YB-1 (25) | 11 | 5.3 | (0.15, 0.25) |
| Example 24 | A3 (50) | YF-2 (50) | 10 | 5.3 | (0.15, 0.25) |
| Comparative Example 2 | b-1 (67) | YF-2 (33) | 7 | 3.8 | (0.16, 0.26) |
| Comparative Example 3 | c-1 (67) | YF-2 (33) | 6 | 3.6 | (0.16, 0.27) |
| Comparative Example 4 | a-1 (50) | YF-2 (50) | 3 | 3.3 | (0.16, 0.27) |
| Comparative Example 5 | — | YB-4 (100) | 0 | 3.2 | (0.15, 0.26) |
| Comparative Example 6 | — | YF-2 (100) | 0 | 2.2 | (0.16, 0.27) |

(Note 2)The term "ratio of formula [1-1]" refers to a molar ratio between the silsesquioxane compound and hole transport material in the hole transport layer. For example, in Example 16, the value is obtained by calculating a ratio among a total of four molecules, i.e., three molecules of Exemplified Compound A6 and one molecule of the hole transport material YB-3.

Example 25

In this example, an organic light emitting element in which an anode, a hole transport layer, an emission layer, a hole blocking layer, an electron transport layer, and a cathode were formed in the stated order on a substrate was produced by a method described below. In addition, part of the materials used in this example are listed below.

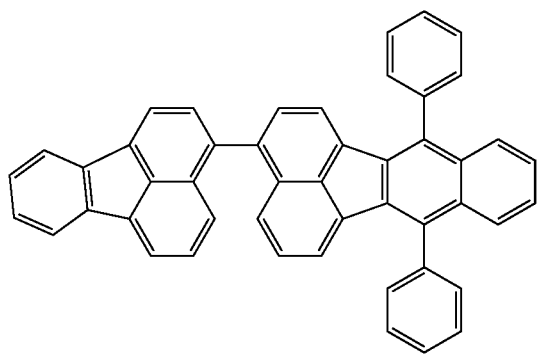

K1

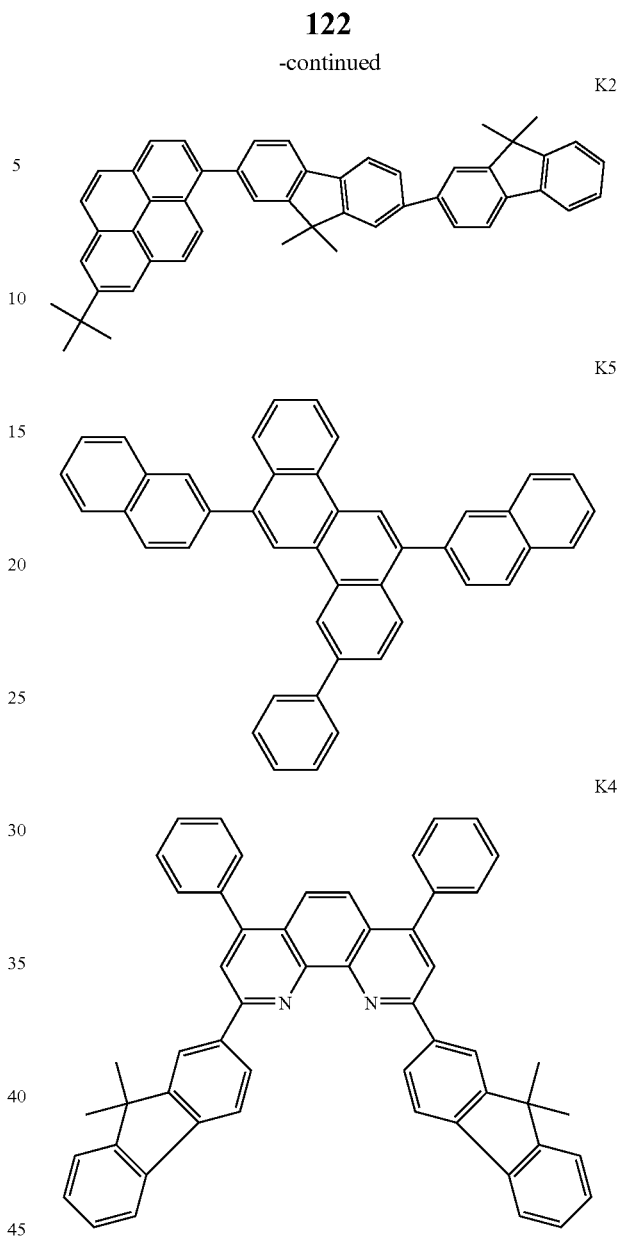

Indium tin oxide (ITO) was formed into a film on a glass substrate by a sputtering method. Thus, the anode was formed. At this time, the thickness of the anode was set to 120 nm. Next, the substrate with the anode was sequentially subjected to ultrasonic washing with acetone and isopropyl alcohol (IPA), and was then subjected to boil washing with IPA, followed by drying. Further, the dried product was subjected to UV/ozone washing. The substrate treated by the foregoing method was used as a transparent conductive supporting substrate in the following steps.

Next, a chloroform solution having a concentration of 0.25% by weight was prepared by mixing Exemplified Compound B5 and chloroform. Next, the chloroform solution was dropped onto the ITO electrode and then a film was formed by spin coating at 500 RPM for 10 seconds and then at 1,000 RPM for one minute. After that, the solvent in the thin film was completely removed by drying in a vacuum oven at 80° C. for 10 minutes. Thus, the hole transport layer was formed. At this time, the thickness of the hole transport layer was 30 nm.

Next, organic compound layers and electrode layers shown in Table 5 below were continuously formed by vacuum deposition involving using resistance heating in a vacuum chamber at $1\times10^{-5}$ Pa to produce the organic light emitting element.

TABLE 5

|  | Constituent material | Thickness [nm] |
|---|---|---|
| Emission layer | K1 (guest, weight concentration: 5%) K2 (host, weight concentration: 95%) | 20 |
| Hole blocking layer | K5 | 30 |
| Electron transport layer | K4 | 20 |
| First metal electrode layer (cathode) | Al | 150 |

The resultant organic light emitting element had a light emitting efficiency at a luminance of 1,000 cd/m$^2$ of 8.2 cd/A and good blue light emission was observed.

Example 26

An organic light emitting element was obtained by the same method as that of Example 25 except that in Example 25, Exemplified Compound B16 was used instead of Exemplified Compound B5 as the constituent material for the hole transport layer.

The resultant organic light emitting element had a light emitting efficiency at a luminance of 1,000 cd/m$^2$ of 8.4 cd/A and good blue light emission was observed.

Example 27

An organic light emitting element was obtained by the same method as that of Example 25 except that in Example 25, Exemplified Compound C3 was used instead of Exemplified Compound B5 as the constituent material for the hole transport layer.

The resultant organic light emitting element had a light emitting efficiency at a luminance of 1,000 cd/m$^2$ of 8.7 cd/A and good blue light emission was observed.

Example 28

An organic light emitting element was obtained by the same method as that of Example 25 except that in Example 25, Exemplified Compound C6 was used instead of Exemplified Compound B5 as the constituent material for the hole transport layer.

The resultant organic light emitting element had a light emitting efficiency at a luminance of 1,000 cd/m$^2$ of 8.4 cd/A and good blue light emission was observed.

Example 29

An organic light emitting element was obtained by the same method as that of Example 25 except that in Example 25, Exemplified Compound C24 was used instead of Exemplified Compound B5 as the constituent material for the hole transport layer.

The resultant organic light emitting element had a light emitting efficiency at a luminance of 1,000 cd/m$^2$ of 8.9 cd/A and good blue light emission was observed.

Example 30

An organic light emitting element was obtained by the same method as that of Example 25 except that in Example 25, Exemplified Compound D2 was used instead of Exemplified Compound B5 as the constituent material for the hole transport layer.

The resultant organic light emitting element had a light emitting efficiency at a luminance of 1,000 cd/m$^2$ of 8.9 cd/A and good blue light emission was observed.

Comparative Example 7

An organic light emitting element was obtained by the same method as that of Example 25 except that in Example 25, Compound a-1 was used instead of Exemplified Compound B5 as the constituent material for the hole transport layer.

The resultant organic light emitting element had a light emitting efficiency at a luminance of 1,000 cd/m$^2$ of 3.6 cd/A and blue light emission was observed.

Result and Discussion

As described above, the silsesquioxane compound of the present invention can provide an organic light emitting element that drives while showing high light emitting efficiency because the compound has a low absorbance and a wide band gap in a thin-film state. In addition, the use of a mixed thin-film layer characterized by containing the silsesquioxane compound and a tertiary arylamine compound, and having a low absorbance and a wide band gap can provide an organic light emitting element that drives while showing high light emitting efficiency.

REFERENCE SIGNS LIST

18: TFT element, 21: anode, 22: organic compound layer, 23: cathode.

ADVANTAGEOUS EFFECTS OF INVENTION

The organic light emitting element of the present invention contains, as a constituent material, a silsesquioxane compound that has a low absorbance and a wide band gap in a thin-film state. In addition, the organic light emitting element of the present invention includes a mixed thin-film layer containing the siloxane compound and a tertiary arylamine compound, and having a low absorbance and a wide band gap. Accordingly, according to the present invention, there can be provided an organic light emitting element having high light emitting efficiency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-077440, filed Apr. 3, 2013, which is hereby incorporated by reference herein in its entirety.

The invention claimed is:

1. An organic light emitting element comprising:
an anode;
a cathode;
an emission layer placed between the anode and the cathode; and
a hole transport layer disposed between the anode and the emission layer, wherein the hole transport layer comprises a siloxane compound and another compound having a tertiary arylamine structure; and wherein a number of SP$^2$ carbon atoms in the hole transport layer is ten times or less a number of silicon atoms in the hole transport layer.

2. The organic light emitting element according to claim 1, wherein the siloxane compound comprises a silsesquioxane compound having any one of general formulae [1] to [3]:

[4A]

in the formula [4A], each of $Ar_{1a}$ to $Ar_{3a}$ is a substituted or unsubstituted aryl group, * is a bonding hand with a silsesquioxane skeleton, and m and n each is 0 or 1, provided that n is 0 when m is 0;

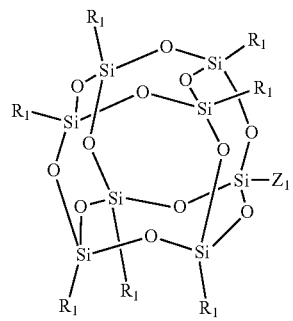
[1]

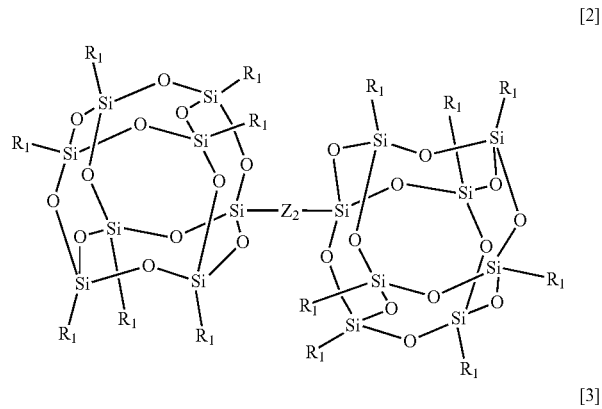
[2]

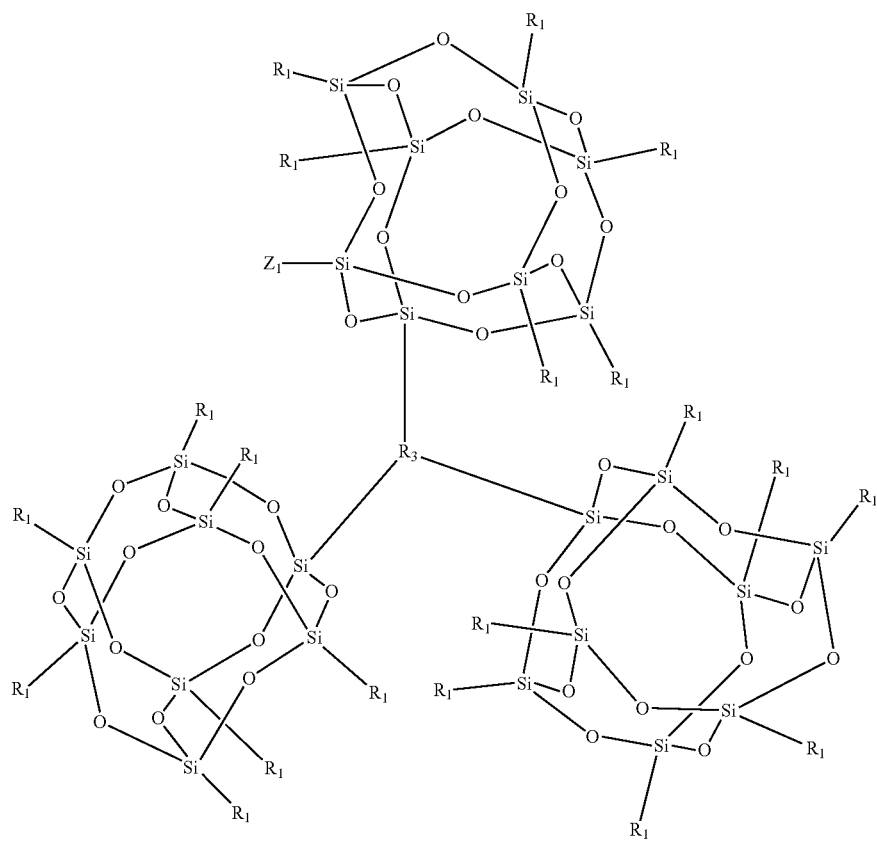
[3]

in the formulae [1] to [3], $R_1$ is an alkyl group having 1 or more and 8 or less carbon atoms, and multiple $R_1$'s in each of the formulae [1] to [3] may be identical to or different from each other;

in the formula [1], $Z_1$ is a monovalent alkyl group having 1 to 8 carbon atoms, a unit having general formula [4A], or an aromatic amino group selected from the following general formulae [5] to [9]:

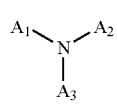
[5]

[6]

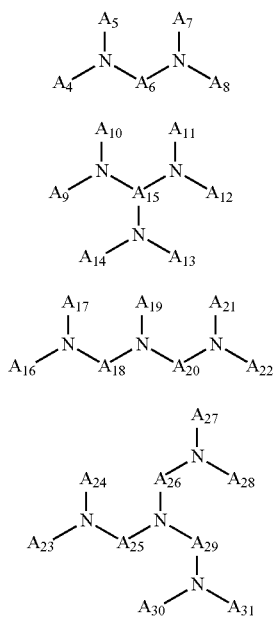

[7]

[8]

[9]

in the formula [5], $A_1$ to $A_3$ each is a bonding hand with a silsesquioxane skeleton or a unit having general formula [10A];

in the formula [6], $A_4$, $A_5$, $A_7$, and $A_8$ each is a bonding hand with a silsesquioxane skeleton or a unit having general formula [10A], and $A_6$ is a bonding hand with a silsesquioxane skeleton or a unit having any one of general formulae [10B] to [10D];

in the formula [7], $A_9$ to $A_{14}$ each is a bonding hand with a silsesquioxane skeleton or a unit having general formula [10A], and $A_{15}$ is a bonding hand with a silsesquioxane skeleton or a unit having any one of general formulae [10E] to [10G];

in the formula [8], $A_{16}$, $A_{17}$, $A_{19}$, $A_{21}$, and $A_{22}$ each is a bonding hand with a silsesquioxane skeleton or a unit having general formula [10A], and $A_{18}$ and $A_{20}$ each is a bonding hand with a silsesquioxane skeleton or a unit having any one of general formulae [10B] to [10D]; and in the formula [9], $A_{23}$, $A_{24}$, $A_{27}$, $A_{28}$, $A_{30}$, and $A_{31}$ each is a bonding hand with a silsesquioxane skeleton or a unit having general formula [10A], and $A_{25}$, $A_{26}$, and $A_{29}$ each is a bonding hand with a silsesquioxane skeleton or a unit having any one of general formulae [10B] to [10D]:

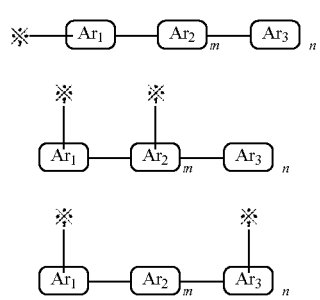

[10A]

[10B]

[10C]

[10D]

[10E]

[10F]

[10G]

in the formulae [10A] to [10G], $Ar_1$ to $Ar_3$ each is an alkyl group having 1 to 8 carbon atoms, a phenoxy group that may have an alkyl group having 1 or more and 8 or less carbon atoms, or an aryl group that may have an alkoxy group, ※ is a bonding hand with an N atom, and m and n each is 0 or 1, provided that n is 0 when m is 0;

in the formula [2], $Z_2$ is a divalent alkyl group having 1 to 8 carbon atoms, a unit having any one of general formulae [4B] to [4D], or an aromatic amino group selected from the following general formulae [5] to [9]:

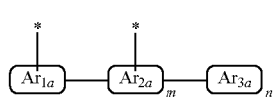

[4B]

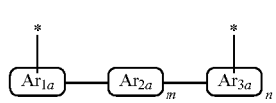

[4C]

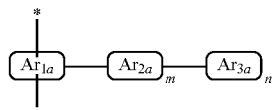

[4D]

in the formulae [4B] to [4D], $Ar_{1a}$ to $Ar_{3a}$ each is an alkyl group having 1 to 8 carbon atoms, a phenoxy group that may have an alkyl group having 1 or more and 8 or less carbon atoms, or an aryl group that may have an alkoxy group, * is a bonding hand with a silsesquioxane skeleton, and m and n each is 0 or 1, provided that n is 0 when m is 0;

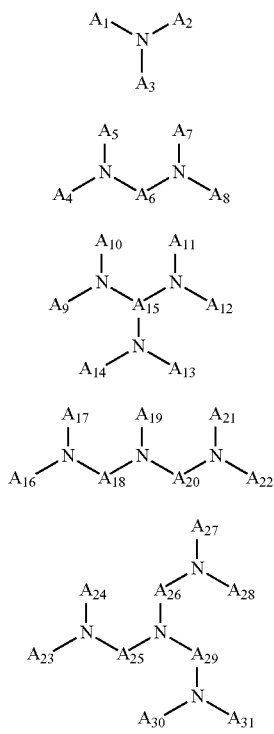

[5]

[6]

[7]

[8]

[9]

in the formula [5], $A_1$ to $A_3$ each is a bonding hand with a silsesquioxane skeleton or a unit having general formula [10A];

in the formula [6], $A_4$, $A_5$, $A_7$, and $A_8$ each is a bonding hand with a silsesquioxane skeleton or a unit having general formula [10A], and $A_6$ is a unit having any one of general formulae [10B] to [10D];

in the formula [7], $A_9$ to $A_{14}$ each is a bonding hand with a silsesquioxane skeleton or a unit having general formula [10A], and $A_{15}$ is a unit having any one of general formulae [10E] to [10G];

in the formula [8], $A_{16}$, $A_{17}$, $A_{19}$, $A_{21}$, and $A_{22}$ each is a bonding hand with a silsesquioxane skeleton or a unit having general formula [10A], and $A_{18}$ and $A_{20}$ each is a unit having any of general formulae [10B] to [10D]; and in the formula [9], $A_{23}$, $A_{24}$, $A_{27}$, $A_{28}$, $A_{30}$, and $A_{31}$ each is a bonding hand with a silsesquioxane skeleton or a unit having general formula [10A], and $A_{25}$, $A_{26}$, and $A_{29}$ each is a unit having any one of general formulae [10B] to [10D]:

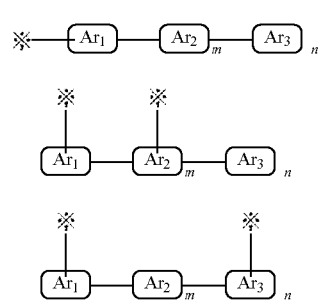

[10A]

[10B]

[10C]

[10D]

[10E]

[10F]

[10G]

in the formulae [10A] to [10G], $Ar_1$ to $Ar_3$ each is a substituted or unsubstituted aryl group, ※ is a bonding hand with an N atom, and m and n each is 0 or 1, provided that n is 0 when m is 0; and in the formula [3], $Z_3$ is a trivalent alkyl group having 1 to 8 carbon atoms, a unit having any one of general formulae [4E] to [4G], or an aromatic amino group selected from the following general formulae [5] to [9]:

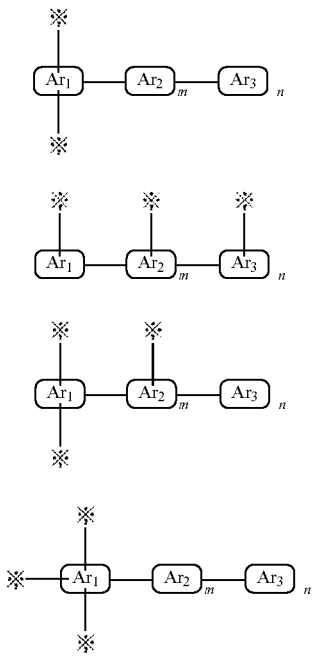

[4E]

[4F]

[4G]

in the formulae [4E] to [4G], $Ar_{1a}$ to $Ar_{3a}$ each is a substituted or unsubstituted aryl group, * is a bonding hand with a silsesquioxane skeleton, and m and n each is 0 or 1, provided that n is 0 when m is 0;

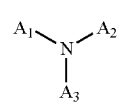

[5]

-continued

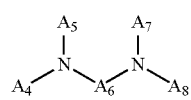
[6]

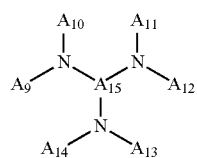
[7]

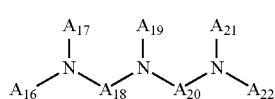
[8]

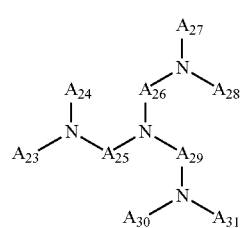
[9]

in the formula [5], $A_1$ to $A_3$ each is a bonding hand with a silsesquioxane skeleton or a unit having general formula [10A];

in the formula [6], $A_4$, $A_5$, $A_7$, and $A_8$ each is a bonding hand with a silsesquioxane skeleton or a unit having general formula [10A], and $A_6$ is a unit having any one of general formulae [10B] to [10D];

in the formula [7], $A_9$ to $A_{14}$ each is a bonding hand with a silsesquioxane skeleton or a unit having general formula [10A], and $A_{15}$ is a unit having any one of general formulae [10E] to [10G];

in the formula [8], $A_{16}$, $A_{17}$, $A_{19}$, $A_{21}$, and $A_{22}$ each is a bonding hand with a silsesquioxane skeleton or a unit having general formula [10A], and $A_{18}$ and $A_{20}$ each is a unit having any one of general formulae [10B] to [10D]; and in the formula [9], $A_{23}$, $A_{24}$, $A_{27}$, $A_{28}$, $A_{30}$, and $A_{31}$ each is a bonding hand with a silsesquioxane skeleton or a unit having general formula [10A], and $A_{25}$, $A_{26}$, and $A_{29}$ each is a unit having any one of general formulae [10B] to [10D]:

[10A]

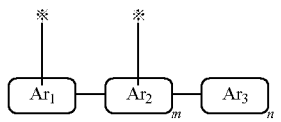
[10B]

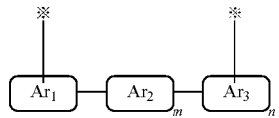
[10C]

[10D]

[10E]

[10F]

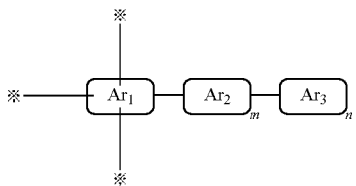
[10G]

in the formulae [10A] to [10G], $Ar_1$ to $Ar_3$ each is a substituted or unsubstituted aryl group, ※ is a bonding hand with an N atom, and m and n each is 0 or 1, provided that n is 0 when m is 0.

3. The organic light emitting element according to claim 2, wherein the siloxane compound comprises a compound having general formula [1];

$Z_1$ is an alkyl group having 1 or more and 8 or less carbon atoms, or a unit having general formula [4A]; and $Ar_{1a}$ to $Ar_{3a}$ each is a substituent selected from a phenyl group, a biphenyl group, a terphenyl group, a naphthyl group, and a fluorenyl group.

4. The organic light emitting element according to claim 2, wherein $Z_1$ in the formula [1] is an aromatic amino group selected from the general formulae [5] to [9];

$Z_2$ in the formula [2] is an aromatic amino group selected from the general formulae [5] to [9];

$Z_3$ in the formula [3] is an aromatic amino group selected from the general formulae [5] to [9]; and the aryl group comprises a substituent selected from a phenyl group, a biphenyl group, a terphenyl group, a naphthyl group, and a fluorenyl group.

5. The organic light emitting element according to claim 2, wherein the siloxane compound comprises a compound having general formula [11] or [12]:

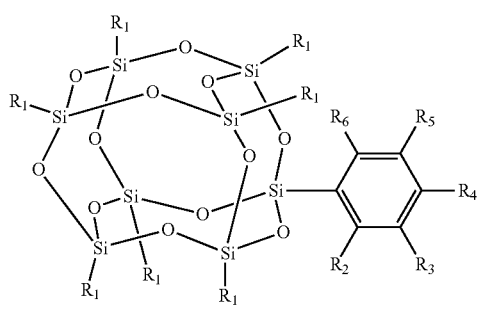

[11]

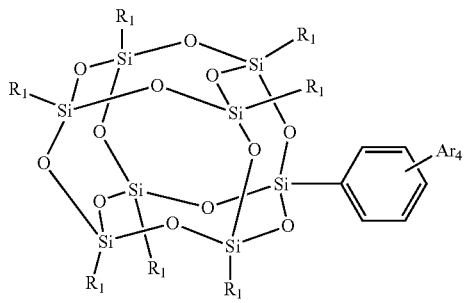

[12]

in the formulae [11] and [12], $R_1$ is an alkyl group having 1 or more and 8 or less carbon atoms, and multiple $R_1$'s in each of the formulae [11] and [12] may be identical to or different from each other;

in the formula [11], $R_2$ to $R_6$ each is a hydrogen atom, or an alkyl group or alkoxy group having 1 to 8 carbon atoms; and in the formula [12], $Ar_4$ is an aryl group selected from a phenyl group, a biphenyl group, a terphenyl group, a naphthyl group, and a fluorenyl group, and the aryl group may further have a substituent.

6. The organic light emitting element according to claim 2, wherein the siloxane compound has any one of general formulae [13] to [15]:

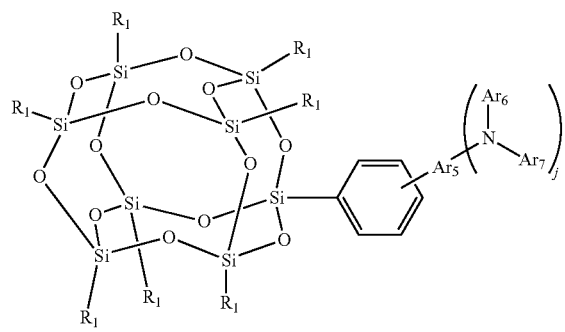

[13]

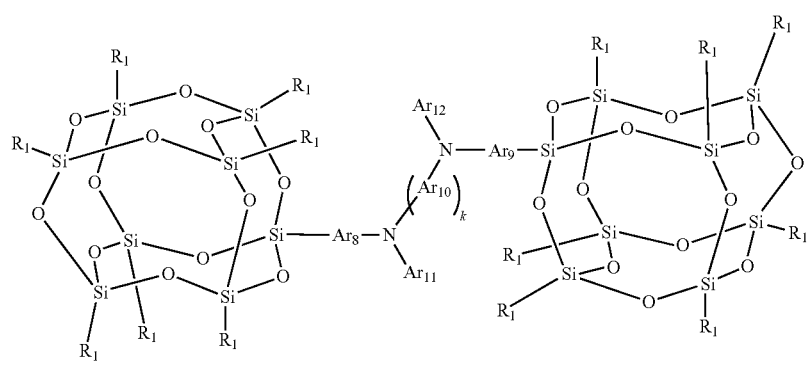

[14]

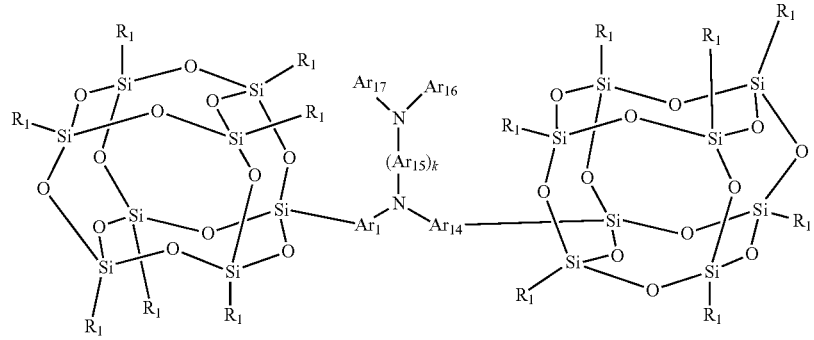
[15]

in the formulae [13] to [15], $R_1$ is an alkyl group having 1 or more and 8 or less carbon atoms, and multiple $R_1$'s in each of the formulae [13] to [15] may be identical to or different from each other;

in the formula [13], j is an integer of 1 to 3, $Ar_5$ is a (j+1)-valent arylene group selected from a phenylene group, a biphenylene group, a terphenylene group, a naphthylene group, and a fluorenylene group, $Ar_6$ and $Ar_7$ each is an aryl group selected from a phenyl group, a biphenyl group, a terphenyl group, a naphthyl group, and a fluorenyl group, and may be identical to or different from each other, and the aryl group may have an alkyl group having 1 or more and 8 or less carbon atoms, and when j is 2 or more, multiple $Ar_6$'s and $Ar_7$'s may be identical to or different from each other;

in the formula [14], k is 1 or 2, $Ar_8$ to $Ar_{10}$ each is a divalent arylene group selected from a phenylene group, a biphenylene group, a terphenylene group, a naphthylene group, and a fluorenylene group, $Ar_{11}$ and $Ar_{12}$ each is an aryl group selected from a phenyl group, a biphenyl group, a terphenyl group, a naphthyl group, and a fluorenyl group, and may be identical to or different from each other, and the aryl group may have an alkyl group having 1 or more and 8 or less carbon atoms, and when k is 2, two $Ar_{10}$'s may be identical to or different from each other; and in the formula [15], k is 1 or 2, $Ar_{13}$ to $Ar_{15}$ each is a divalent arylene group selected from a phenylene group, a biphenylene group, a terphenylene group, a naphthylene group, and a fluorenylene group, $Ar_{16}$ and $Ar_{17}$ each is an aryl group selected from a phenyl group, a biphenyl group, a terphenyl group, a naphthyl group, and a fluorenyl group, and may be identical to or different from each other, and the aryl group may have an alkyl group having 1 or more and 8 or less carbon atoms, and when k is 2, two $Ar_{15}$'s may be identical to or different from each other.

7. The organic light emitting element according to claim 1, wherein the compound having a tertiary arylamine structure has any one of general formulae [27] to [32]:

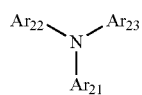
[27]

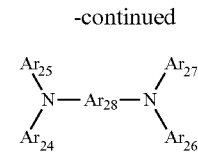
[28]

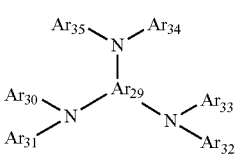
[29]

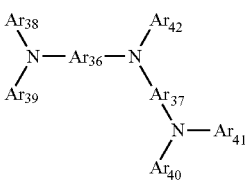
[30]

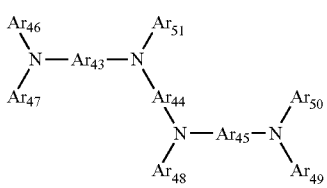
[31]

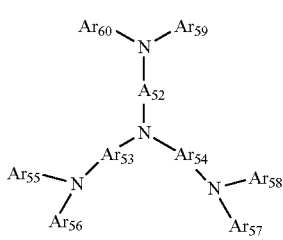
[32]

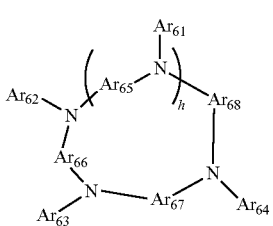
[33]

in the formula [27], $Ar_{21}$ to $Ar_{23}$ each is a monovalent substituent selected from an alkyl group, an alkoxy group, an amino group, an aryl group, and a heterocyclic group;

in the formula [28], $Ar_{24}$ to $Ar_{27}$ each is a monovalent substituent selected from an alkyl group, an alkoxy group, an amino group, an aryl group, and a heterocyclic group, and $Ar_{28}$ is a divalent substituent selected from an alkyl group, an alkoxy group, an amino group, an aryl group, and a heterocyclic group;

in the formula [29], $Ar_{30}$ to $Ar_{35}$ each is a monovalent substituent selected from an alkyl group, an alkoxy group, an amino group, an aryl group, and a heterocyclic group, and $Ar_{29}$ is a trivalent substituent selected from an alkyl group, an alkoxy group, an amino group, an aryl group, and a heterocyclic group;

in the formula [30], $Ar_{38}$ to $Ar_{42}$ each is a monovalent substituent selected from an alkyl group, an alkoxy group, an amino group, an aryl group, and a heterocyclic group, and $Ar_{36}$ and $Ar_{37}$ each is a divalent substituent selected from an alkyl group, an alkoxy group, an amino group, an aryl group, and a heterocyclic group;

in the formula [31], $Ar_{46}$ to $Ar_{51}$ each is a monovalent substituent selected from an alkyl group, an alkoxy group, an amino group, an aryl group, and a heterocyclic group, and $Ar_{43}$ to $Ar_{45}$ each is a divalent substituent selected from an alkyl group, an alkoxy group, an amino group, an aryl group, and a heterocyclic group; and in the formula [32], $Ar_{55}$ to $Ar_{60}$ each is a monovalent substituent selected from an alkyl group, an alkoxy group, an amino group, an aryl group, and a heterocyclic group, and $Ar_{52}$ to $Ar_{54}$ each is a divalent substituent selected from an alkyl group, an alkoxy group, an amino group, an aryl group, and a heterocyclic group.

8. A display apparatus comprising multiple pixels, wherein at least one of the multiple pixels includes the organic light emitting element according to claim 1 and an active element connected to the organic light emitting element.

9. An image information processing apparatus comprising:

an input portion for inputting image information; and a display portion for displaying an image, wherein the display portion comprises the display apparatus according to claim 8.

10. A lighting apparatus comprising:

the organic light emitting element according to claim 1; and an AC/DC converter circuit for supplying a driving voltage to the organic light emitting element.

11. An image forming apparatus comprising:

a photosensitive member;

a charging portion for charging a surface of the photosensitive member;

an exposure portion for exposing the photosensitive member; and a developing device for developing an electrostatic latent image formed on the surface of the photosensitive member, wherein the exposure portion includes the organic light emitting element according to claim 1.

12. An exposure machine comprising the organic light emitting elements according to claim 1, the organic light emitting elements being placed to form a line, wherein the organic light emitting elements expose a photosensitive member.

13. The organic light emitting element according to claim 1, wherein a molar ratio of the siloxane compound in the hole transport layer is 10% to 25%.

14. The organic light emitting element according to claim 2, wherein a molar ratio of the silsesquioxane compound in the hole transport layer is 10% to 25%.

15. The organic light emitting element according to claim 1, wherein the number of $SP^2$ carbon atoms in the hole transport layer is 6.67 times or less the number of silicon atoms in the hole transport layer.

* * * * *